(12) United States Patent
Calderwood et al.

(10) Patent No.: US 7,790,741 B2
(45) Date of Patent: Sep. 7, 2010

(54) IMIDAZOTHIAZOLES AND IMIDAZOXAZOLES

(75) Inventors: David J. Calderwood, Framingham, MA (US); Kristine E. Frank, Worcester, MA (US); David W. Borhani, Hartsdale, NY (US); Heather M. Davis, Oxford, MA (US); Nathan S. Josephsohn, Boston, MA (US); Barbara S. Skinner, Worcester, MA (US)

(73) Assignee: Abbott Laboratories, Abbott Park, IL (US)

( * ) Notice: Subject to any disclaimer, the term of this patent is extended or adjusted under 35 U.S.C. 154(b) by 154 days.

(21) Appl. No.: 11/973,147

(22) Filed: Oct. 5, 2007

(65) Prior Publication Data

US 2008/0161341 A1  Jul. 3, 2008

Related U.S. Application Data

(60) Provisional application No. 60/849,873, filed on Oct. 6, 2006.

(51) Int. Cl.
| | |
|---|---|
| A61K 31/437 | (2006.01) |
| A61K 31/4184 | (2006.01) |
| A61K 31/424 | (2006.01) |
| A61K 31/429 | (2006.01) |
| C07D 487/04 | (2006.01) |
| C07D 513/04 | (2006.01) |
| C07D 498/04 | (2006.01) |

(52) U.S. Cl. .................. 514/303; 514/368; 514/375; 546/121; 548/154; 548/218

(58) Field of Classification Search .......... None
See application file for complete search history.

(56) References Cited

U.S. PATENT DOCUMENTS

| 6,696,464 | B2 | 2/2004 | McClure et al. |
| 7,087,607 | B2 | 8/2006 | Gerlach et al. |
| 7,153,873 | B2 | 12/2006 | Gerlach et al. |
| 2004/0176390 | A1 | 9/2004 | Blumberg et al. |
| 2005/0074632 | A1 | 4/2005 | Lee et al. |
| 2005/0079387 | A1 | 4/2005 | Lee et al. |
| 2005/0272791 | A1 | 12/2005 | Bonjouklian et al. |
| 2006/0287324 | A1 | 12/2006 | Sun et al. |

FOREIGN PATENT DOCUMENTS

| WO | WO02/072579 | 9/2002 |
| WO | WO2008/008539 | 1/2008 |

OTHER PUBLICATIONS

Strutz, Expert Opin. Investig. Drugs., 10(11), pp. 1989-2001, section 5.2 (1994).*
Schafer et al. Drug Discovery Today 2008, 13 (21/22), 913-916.*
Horig et al. Journal of Translational Medicine 2004, 2(44).*

* cited by examiner

*Primary Examiner*—Kamal A Saeed
*Assistant Examiner*—Michael Barker
(74) *Attorney, Agent, or Firm*—Gayle B. O'Brien; Kenneth Zwicker

(57) ABSTRACT

The present invention is directed to novel compounds of formula (I)

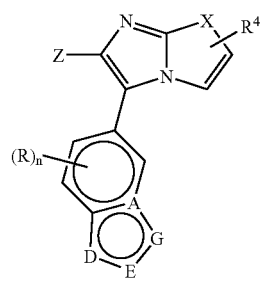

Formula (I)

wherein the variables are as defined herein. The compounds of formula (I) are useful as kinase inhibitors and as such would be useful in treating certain conditions and diseases, especially inflammatory conditions and diseases and proliferative disorders and conditions, for example, cancers.

25 Claims, No Drawings

IMIDAZOTHIAZOLES AND IMIDAZOXAZOLES

CROSS-REFERENCE TO RELATED APPLICATION

This application claims the benefit of priority to U.S. application No. 60/849,873, filed Oct. 6, 2006.

BACKGROUND OF THE INVENTION

Protein phosphorylation, at specific amino acid residues, is important for the regulation of many cellular processes including cell cycle progression and division, signal transduction, and apoptosis. The phosphorylation is usually a transfer reaction of the terminal phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine (S/T) kinases. The phosphorylation reactions, and counteracting phosphatase reactions, on the tyrosine, serine and threonine residues are involved in countless cellular processes that underlie responses to diverse intracellular signals, regulation of cellular functions, and activation or deactivation of cellular processes. A cascade of protein kinases often participate in intracellular signal transduction and are necessary for the realization of cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell. Given the importance and diversity of protein kinase function, it is not surprising that alterations in phosphorylation are associated with many diseases such as cancer, diabetes, inflammation, and hypertension.

The identification of effective small molecules that specifically inhibit protein kinases involved in abnormal or inappropriate cell proliferation, signaling, differentiation, protein production, or metabolism is therefore desirable. In particular, the identification of methods and compounds that specifically inhibit the function of kinases that are involved in immune modulation or proliferative disorders.

The present invention provides novel compounds that inhibit one or more S/T kinase or receptor or non-receptor tyrosine kinase. The compounds of the present invention display cytokine inhibitory activity.

Cytokine mediated diseases and cytokine inhibition, suppression and antagonism are used in the context of diseases or conditions in which excessive or unregulated production or activity of one or more cytokine occurs. Examples of such cytokines are tumour necrosis factor alpha (TNFα), interleukin-1 (IL-1), interleukin-6 (IL-6) and interleukin-8 (IL-8). There remains a need for compounds which are useful in treating cytokine mediated diseases, and as such, inhibit, suppress or antagonize the production or activity of cytokines such as TNF, IL-1, IL-6 and IL-8.

The p38 MAP kinase (p38, also known as CSBP or SAPK) signaling pathway has been reported to be responsible for the expression of pro-inflammatory cytokines (such as TNF, IL-1, IL-6, IL-8) that are elevated in many inflammatory and auto-immune diseases (see J. C. Lee, *Nature Reviews Drug Discovery* 2003, 2, 717-726 and references cited therein). This pathway has been shown to be activated by cellular stressors, such as osmotic shock, UV light, free radicals, bacterial toxins, viruses, cytokines, chemokines and in response, mediates the expression of several cytokines including, but not limited to, TNF, IL-1, IL-6 and IL-8. In cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of the physiological response to cellular stress, acute or chronic cellular stress leads to the excess or unregulated expression of pro-inflammatory cytokines. This, in turn, leads to tissue damage, often resulting in pain and debilitation (see G. Panayi, *N Engl J Med* 2001, 344(12), 907; J. Smolen *Nature Reviews Drug Discovery* 2003, 2, 473 and references cited therein). The four known isoforms of p38 MAP kinase (p38 α, β, γ, δ) each showing different expression levels, tissue distributions and regulation, support the concept that they are involved in the etiology of many diseases.

Many solid tumors increase in mass through proliferation of malignant cells and stromal cells, including endothelial cells. In order for a tumor to grow lager than 2-3 mm in diameter, it must form a vasculature, a process known as angiogenesis. A selective p38 inhibitor has been shown to inhibit angiogenesis (see J. R. Jackson, *J. Pharmacol Exp. Therapeutics*, 1998, 284, 687). Because angiogenesis is a critical component of the mass expansion of solid tumours, the development of new p38 kinase inhibitors for the inhibition of this process represents a promising approach for anti-tumour therapy. The compounds of the present invention are also useful in inhibiting growth of susceptible neoplasms (see R. M. Schultz, *Potential of p38 MAP kinase inhibitors in the treatment of cancer*. In: E. Jucker (editor), *Progress in Drug Research* 2003, 60, 59-92. The term "susceptible neoplasm" used in present application includes human cancers such as malignant melanoma, colorectal carcinoma, gastric carcinoma, breast carcinoma and non-small cell lung carcinoma.

Furthermore, inhibition of p38 kinase may be effective in treatment of certain viral conditions such as influenza (*J. Immunology*, 2000, 164, 3222), rhinovirus (*J. Immunology*, 2000, 165, 5211) and HIV (*Proc. Nat. Acad. Sci.*, 1998, 95, 7422).

In summary, a number of inhibitors of p38 kinase are under active investigation for the treatment of a variety of disorders (Boehm, Adams *Exp. Opin. Ther. Patents* 2000, 10(1), 25-37). There remains a need for treatment in this field for compounds that are cytokine suppressive, i.e. compounds that are capable of inhibiting p38 kinase.

SUMMARY OF THE INVENTION

The present invention provides novel compounds that inhibit one or more S/T kinase or receptor or non-receptor tyrosine kinase. The compounds of the present invention display cytokine inhibitory activity.

In a first embodiment, the invention provides a compound of formula (I)

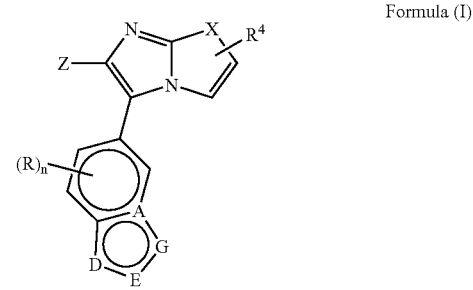

Formula (I)

pharmaceutically acceptable salts thereof, metabolites thereof, isomers thereof, or pro-drugs thereof, wherein
X is O or S;
A is C or N;
D is O, N or NR$^b$;
E is N or CR$^a$;
G is N, NR$^b$ or CR$^c$;
Z is selected from the optionally substituted group consisting of phenyl, naphthyl or heteroaryl;
R for each occurrence is independently H, F, Cl, or (C$_1$-C$_4$)alkyl;
R$^a$ is selected from the group consisting of H, NR$^2$R$^3$, pyridinyl and (C$_1$-C$_6$)alkyl;
R$^b$ is selected from the group consisting of H, —S(O)$_2$—(C$_1$-C$_4$)alkyl, optionally substituted (C$_1$-C$_6$)alkyl, optionally substituted (C$_3$-C$_6$)cycloalkyl, optionally substituted (C$_1$-C$_6$)alkyl-R$^1$, optionally substituted aryl, optionally substituted heterocyclyl and optionally substituted heteroaryl;
R$^c$ is H or R$^c$ is selected from the group consisting of NR$^2$R$^3$, optionally substituted —C(O)—NH—(C$_1$-C$_4$)alkyl, —CO$_2$—(C$_1$-C$_3$)alkyl, optionally substituted (C$_1$-C$_6$)alkyl, optionally substituted (C$_3$-C$_6$)cycloalkyl, optionally substituted (C$_3$-C$_6$)cycloalkenyl, —(C$_1$-C$_6$)alkyl-R$^1$, optionally substituted phenyl, optionally substituted heterocyclyl and optionally substituted heteroaryl; wherein R$^c$ is optionally substituted by one or more substituents selected from the group consisting of CF$_3$, CN, halo, optionally substituted (C$_1$-C$_3$)alkyl, optionally substituted (C$_1$-C$_3$)alkoxy, —C(O)—NH-optionally substituted (C$_1$-C$_3$)alkyl, —C(O)—NH-optionally substituted (C$_1$-C$_6$)alkyl-optionally substituted amino, —C(O)—OCH$_3$, —NH—C(O)-optionally substituted (C$_1$-C$_3$)alkyl, OH, COOH, NR$^2$R$^3$, —C(O)—NH-optionally substituted (C$_1$-C$_5$)alkyl; —C(O)—NH-optionally substituted (C$_3$-C$_6$)cycloalkyl, —C(O)—NH-optionally substituted (C$_1$-C$_6$)alkyl-optionally substituted (C$_3$-C$_6$)cycloalkyl, —NH—C(O)—O-optionally substituted (C$_1$-C$_4$)alkyl, NH$_2$, N(H)CH3, N(CH$_3$)$_2$ and —O—C(O)-optionally substituted (C$_1$-C$_3$)alkyl;
R$^1$ is selected from the optionally substituted group consisting of amino, phenyl, heteroaryl, heterocyclyl and (C$_3$-C$_6$) cycloalkyl;
R$^2$ and R$^3$ are independently selected from H and (C$_1$-C$_4$) alkyl;
R$^4$ is H, halo, CN, SO$_2$, CONH—(C$_1$-C$_6$)alkyl, —CO—N(CH$_3$)$_2$, —CO—N(H)-optionally substituted (C$_1$-C$_6$)alkyl, —CO—N(H)-optionally substituted (C$_1$-C$_6$)alkyl-NR$^2$R$^3$, —NHCO—(C$_1$-C$_6$)alkyl, SO$_2$—(C$_1$-C$_6$)alkyl, CO—(C$_1$-C$_6$)alkyl, CO$_2$—(C$_1$-C$_3$)alkyl or optionally substituted (C$_1$-C$_6$) alkyl; and
n is 1, 2 or 3;
provided that the compound is not
1-methyl-6-[6-(6-methyl-pyridin-2-yl)]-imidazo[2,1-b]thiazol-5-yl-1H-benzotriazole;
2-methyl-5-[6-(6-methyl-pyridin-2-yl)]-imidazo[2,1-b]thiazol-5-yl-1H-benzotriazole;
2-methyl-5-[3-methyl-6-(6-methyl-pyridin-2-yl)]-imidazo[2,1-b]thiazol-5-yl-1H-benzotriazole; or
2-methyl-5-[2-methyl-6-(6-methyl-pyridin-2-yl)]-imidazo[2,1-b]thiazol-5-yl-1H-benzotriazole.

In a second embodiment, the compound provides a compound according to the foregoing embodiment wherein
X is O or S;
A is C or N;
D is N or NR$^b$;
E is N or CR$^a$;
G is N, NR$^b$ or CR$^c$;
Z is selected from the optionally substituted group consisting of phenyl, naphthyl or heteroaryl;
R for each occurrence is independently selected from the group consisting of H, F, Cl, or (C$_1$-C$_4$)alkyl;
R$^a$ is selected from the group consisting of H, NR$^2$R$^3$, pyridinyl and (C$_1$-C$_6$)alkyl;
R$^b$ is selected from the group consisting of H, —S(O)$_2$—(C$_1$-C$_4$)alkyl, optionally substituted (C$_1$-C$_6$)alkyl, optionally substituted (C$_3$-C$_6$)Cycloalkyl, optionally substituted (C$_1$-C$_6$)alkyl-R$^1$, optionally substituted aryl, optionally substituted heterocyclyl and optionally substituted heteroaryl;
R$^c$ is selected from the group consisting of H, NR$^2$R$^3$, optionally substituted —C(O)—NH—(C$_1$-C$_4$)alkyl, —CO$_2$—(C$_1$-C$_3$)alkyl, optionally substituted (C$_1$-C$_6$)alkyl, optionally substituted (C$_3$-C$_6$)cycloalkyl, —(C$_1$-C$_6$)alkyl-R$^1$, optionally substituted phenyl, optionally substituted heterocyclyl and optionally substituted heteroaryl;
R$^1$ is selected from the optionally substituted group consisting of amino, phenyl, heteroaryl, heterocyclyl and (C$_3$-C$_6$) cycloalkyl;
R$^2$ and R$^3$ are independently selected from H and (C$_1$-C$_4$) alkyl;
R$^4$ is H, halo, CN, SO$_2$NH$_2$, CONH—(C$_1$-C$_6$)alkyl, NHCO—(C$_1$-C$_6$)alkyl, SO$_2$—(C$_1$-C$_6$)alkyl, CO—(C$_1$-C$_6$) alkyl, CO$_2$—(C$_1$-C$_3$)alkyl or optionally substituted (C$_1$-C$_6$) alkyl; and
n is 1, 2 or 3.

In a third embodiment the invention provides a compound according to any of the foregoing embodiments wherein Z is optionally substituted phenyl.

In a fourth embodiment the invention provides a compound according to any of the foregoing embodiments wherein D is N.

In a fifth embodiment the invention provides a compound according to any of the foregoing embodiments wherein E is N.

In a sixth embodiment the invention provides a compound according to any of the foregoing embodiments wherein A is N.

In a seventh embodiment the invention provides a compound according to any of the foregoing embodiments wherein
G is CR$^c$; and
R$^c$ is NH$_2$ or is selected from the optionally substituted group consisting of —C(O)—NH—(C$_1$-C$_4$)alkyl, phenyl, heteroaryl, heterocyclyl, (C$_1$-C$_4$)alkyl, (C$_3$-C$_4$)cycloalkyl, —(C$_3$-C$_4$)alkylamino and —CO$_2$—(C$_1$-C$_4$) alkyl.

In an eighth embodiment the invention provides a compound according to any of the foregoing embodiments wherein Z is phenyl substituted with one or more substituents each independently selected from CF$_3$ and halogen.

In a ninth embodiment the invention provides a compound according to any of the foregoing embodiments wherein Z is phenyl substituted with one or more F;
R$^c$ is selected from the optionally substituted group consisting of phenyl, imidazolyl, (C$_1$-C$_4$)alkyl, (C$_3$-C$_4$)cycloalkyl and heterocyclyl;
n is 1; and
R is H.

In a tenth embodiment the invention provides a compound according to any of the foregoing embodiments wherein X is O and R$^c$ is selected from the optionally substituted group consisting of phenyl, (C$_1$-C$_4$)alkyl and (C$_3$-C$_4$)cycloalkyl.

In an eleventh embodiment the invention provides a compound according to any of the foregoing embodiments wherein R$^c$ is optionally substituted by one or more substituents selected from the group consisting of $CF_3$, CN, halo, optionally substituted $(C_1-C_3)$alkyl, optionally substituted $(C_1-C_3)$alkoxy, —C(O)—NH-optionally substituted $(C_1-C_3)$alkyl, —C(O)—NH-optionally substituted $(C_1-C_6)$alkyl-optionally substituted amino, —C(O)—$OCH_3$ and —NH—C(O)Optionally substituted $(C_1-C_3)$alkyl.

In a twelfth embodiment the invention provides a compound according to any of the foregoing embodiments wherein the compound is

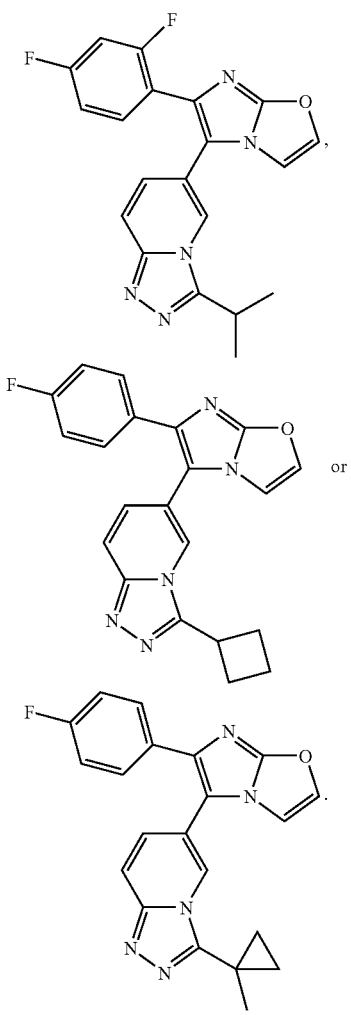

In a thirteenth embodiment the invention provides a compound according to any of embodiments one through five wherein A is C.

In a fourteenth embodiment the invention provides a compound according to any of embodiments one through five and thirteen wherein G is $NR^b$; and $R^b$ is H or is selected from the optionally substituted group consisting of phenyl, $(C_1-C_6)$alkyl, $(C_3-C_6)$cycloalkyl and $(C_1-C_6)$alkyl-$R^1$.

In a fifteenth embodiment the invention provides a compound according to any of embodiments one through five and thirteen through fourteen wherein $R^1$ is $(C_3-C_6)$cycloalkyl or phenyl.

In a sixteenth embodiment the invention provides a compound according to any of embodiments one through five and thirteen through fifteen wherein $R^1$ is $(C_3-C_6)$cycloalkyl or phenyl wherein Z is phenyl substituted with one or more F;

$R^b$ is selected from the optionally substituted group consisting of phenyl, $(C_1-C_6)$alkyl, —$CH_2$-cyclopropyl;

X is O;

n is 1; and

R is H.

In a seventeenth embodiment the invention provides a compound according to any of embodiments one through five and thirteen through sixteen wherein the compound is

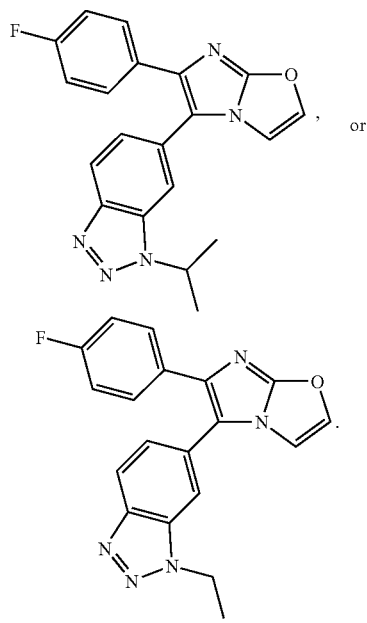

In an eighteenth embodiment the invention provides a compound according to any of embodiments one through five and thirteen through seventeen wherein E is $CR^a$ In an eighteenth embodiment the invention provides a compound according to any of embodiments one through five and thirteen through eighteen wherein G is $NR^b$.

In a nineteenth embodiment the invention provides a compound according to any of embodiments one through five and thirteen through eighteen wherein $R^a$ is $NH_2$, $(C_1-C_4)$alkyl, heteroaryl or —NH—$S(O)_2$-phenyl;

$R^b$ is H or a bond or is selected from the optionally substituted group consisting of $(C_1-C_5)$alkyl, —$(C_1-C_5)$alkyl-$R^1$, $(C_3-C_6)$cycloalkyl and aryl; and A is C.

In a twentieth embodiment the invention provides a compound according to any of embodiments one through five and thirteen through nineteen wherein $R^a$ is $NH_2$, $CH_3$, pyridinyl or —NH—$S(O)_2$-phenyl;

$R^b$ is a bond or is selected from the optionally substituted group consisting of $(C_1-C_5)$alkyl, —$CH_2$-azetidinyl, —$CH_2$-cyclohexyl, —$CH_2$-cyclopropyl, —$CH_2$-pyridinyl, —$CH_2$-tetrahydropyranyl, —$CH_2$-pyrrolidinyl, —$CH_2$-pyrrolyl, benzyl, cyclopropyl, cyclohexyl, and phenyl;

R is H or —$S(O)_2$—$(C_1-C_4)$alkyl;

n is 1; and

Z is phenyl substituted with F.

In a twenty-first embodiment the invention provides a compound according to any of embodiments rough five and thirteen through twenty wherein the compound is

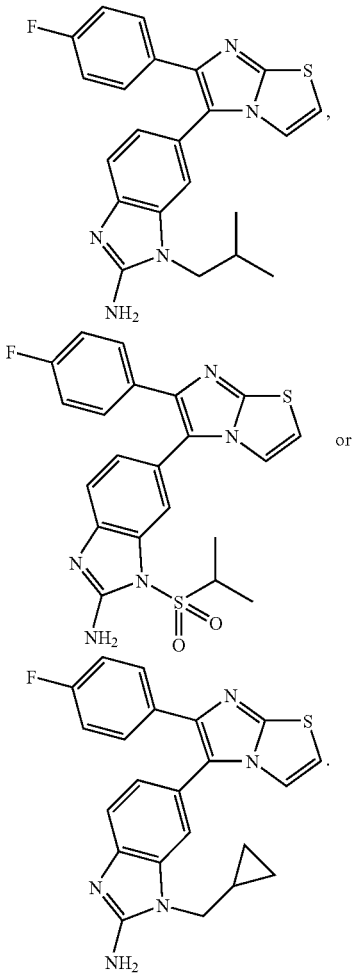

In a twenty-third embodiment the invention provides a compound according to any of embodiments one through three wherein D is O, E is N, A is C and G is $CR^c$;

$R^c$ is $NH_2$ or $R^c$ is selected from the optionally substituted group consisting of —C(O)—NH—($C_1$-$C_4$)alkyl, phenyl, heteroaryl, heterocyclyl, ($C_1$-$C_4$)alkyl, ($C_3$-$C_4$)cycloalkyl, —($C_3$-$C_4$)alkylamino and —$CO_2$—($C_1$-$C_4$)alkyl;

n is 1;

R is H; and

Z is phenyl substituted with one or more F.

In a twenty-fourth embodiment the invention provides a method of treating a condition in a patient comprising administering a therapeutically effective amount of a compound according to any of the foregoing embodiments or a physiologically acceptable salt thereof to said patient, wherein said condition is selected from the group consisting of rheumatoid arthritis, osteoarthritis, asthma, chronic obstructive pulmonary disease, sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy, systemic lupus erythematosus, an ocular condition, a cancer, a solid tumor, fibrosarcoma, osteoma, melanoma, retinoblastoma, a rhabdomyosarcoma, glioblastoma, neuroblastoma, teratocarcinoma, an cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, alpha-1 antitrypsin deficiency, amyotrophic lateral sclerosis, anemia, angina pectoris, anterior horn cell degeneration, anti cd3 therapy, antiphospholipid syndrome, anti-receptor hypersensitivity reactions, hypersensitivity reactions, hyperkinetic movement disorders, hypersensitivity pneumonitis, hypertension, hypokinetic movement disorders, aortic and peripheral aneurysms, hypothalamic-pituitary-adrenal axis evaluation, aortic dissection, arterial hypertension, arteriosclerosis, arteriovenous fistula, ataxia, spinocerebellar degenerations, streptococcal myositis, structural lesions of the cerebellum, Subacute sclerosing panencephalitis, Syncope, syphilis of the cardiovascular system, systemic anaphylaxis, systemic inflammatory response syndrome, systemic onset juvenile rheumatoid arthritis, T-cell or FAB ALL, Telangiectasia, thromboangitis obliterans, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue, atrial fibrillation (sustained or paroxysmal), atrial flutter, atrioventricular block, B cell lymphoma, bone graft rejection, bone marrow transplant (BMT) rejection, small bowel transplant rejection, spinal ataxia, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia, chronic alcoholism, chronic inflammatory pathologies, chronic lymphocytic leukemia, chronic salicylate intoxication, colorectal carcinoma, congestive heart failure, conjunctivitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetic ateriosclerotic disease, Diffuses Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, Epstein Barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, gram negative sepsis, gram positive sepsis, granulomas due to intracellular organisms, hairy cell leukemia, Hallerrorden-Spatz disease, hay fever, heart transplant rejection, hemachromatosis, hemodialysis, hemolytic uremic syndrome/thrombolytic thrombocytopenic purpura, hemorrhage, idiopathic pulmonary fibrosis, antibody mediated cytotoxicity, Asthenia, infantile spinal muscular atrophy, inflammation of the aorta, influenza A, ionizing radiation exposure, iridocyclitis/uveitis/optic neuritis, juvenile rheumatoid arthritis, juvenile spinal muscular atrophy, kidney transplant rejection, legionella, leishmaniasis, lipedema, liver transplant rejection, lymphederma, malaria, malignant Lymphoma, malignant histiocytosis, malignant melanoma, meningococcemia, metabolic/idiopathic, migraine headache, mitochondrial multi-system disorder, monoclonal gammopathy, multiple myeloma, multiple systems degenerations (Mencel Dejerine-Thomas Shi-Drager and Machado-Joseph), myasthenia gravis, mycobacterium avium intracellulare, mycobacterium tuberculosis, myelodysplastic syndrome, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occulsive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, Kaposi's sarcoma, Hodgkin's disease, lymphoma, myeloma, leukaemia, malignant ascites, hematopoietic cancers, Crow-Fukase (POEMS) syndrome (polyneuropathy, organomegaly, endocrinopathy, monoclonal gammopathy, and skin changes syndrome), a diabetic condition such as insulin-dependent diabetes mellitus glaucoma, diabetic retinopathy or microangiopathy, sickle cell anaemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, post perfusion syndrome, post pump syndrome, post-MI cardiotomy syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, Progressive supranucleo Palsy, primary pulmonary hypertension, radiation therapy, Raynaud's phenomenon and disease, Refsum's disease, regular narrow QRS tachycardia, renovascular hypertension, restrictive cardiomyopathy, sarcoma, senile chorea, Senile Dementia of Lewy body type, shock, skin allograft, skin changes syndrome, ocular or macular edema, ocular neovascular disease, scleritis, radial keratotomy, uveitis, vitritis, myopia, optic pits, chronic retinal detachment, postlaser treatment complications, conjunctivitis, Stargardt's disease, Eales disease, retinopathy, macular degeneration, restenosis, ischemia/reperfusion injury, ischemic stroke, vascular occlusion, carotid obstructive disease, ulcerative colitis, inflammatory bowel disease, diabetes, diabetes mellitus, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, idiopathic Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, peripheral vascular disorders, peritonitis, pernicious anemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis A, Hepatitis B, Hepatitis C, His bundle arrythmias, HIV infection/HIV neuropathy, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, pneumocystis carinii pneumonia, pneumonia, connective tissue disease associated interstitial lung disease, mixed connective tissue disease, associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, toxicity, transplants, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci infection, mental disorders (e.g., depression and schizophrenia), Th2 Type and Th1 Type mediated diseases, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome, proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, age-related macular degeneration, acute idiopathic polyneuritis, acuter or chronic immune disease associated with organ transplantation, acute inflammatory demyelinating polyradiculoneuropathy, acute ischemia, adult Still's disease, allergy, anaphylaxis, anti-phospholipid antibody syndrome, aplastic anemia, atopic eczema, atopic dermatitis, autoimmune dermatitis, autoimmune diabetes, autoimmune disorder associated with *streptococcus* infection, autoimmune enteropathy, autoimmune hepatitis, autoimmune hearing loss, autoimmune lymphoproliferative syndrome, autoimmune myocarditis, autoimmune neutropenia, autoimmune premature ovarian failure, autoimmune thrombocytopenia, autoimmune uveitis, Behcet's disease, blepharitis, bronchiectasis, bullous pemphigoid, catastrophic antiphospholipid syndrome, celiac disease, cervical spondylosis, chronic ischemia, cicatricial pemphigoid, clinical isolated syndrome with risk for multiple sclerosis, childhood onset psychiatric disorder, dacrocystitis, dermatomyositis, disc herniation, disc prolapse, drug induced immune hemolytic anemia, endophthalmitis, episcleritis, erythema multiforme, erythema multiforme major, gestational pemphigoid, Guillain-Barre syndrome, heart failure, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojuntivitis sicca, Kussmaul disease or Kussmaul-Meier disease, Landry's paralysis, Langerhan's cell hisiocytosis, livedo reticularis, microscopic polyangiitis, morbus bechterev, motor neuron disorders, mucous membrane pemphigoid, primary progressive multiple sclerosis, secondary progressive multiple sclerosis, relapsing remitting multiple sclerosis, multiple organ failure, myelodysplastic syndrome, nerve root disorder, neuropathy, Non-A Non-B hepatitis, osteolysis, ovarian cancer, pauciarticular JRA, peripheral artery occlusive disease (PAOD), peripheral vascular disease (PVD), peripheral artery disease, phlebitis, polychondritis, polymyalgia rheumatica, poliosis, polyarticular JRA, polyendocrine deficiency syndrome, polymyositis, post-pump syndrome, primary parkinsonism, prostatitis, psoratic arthropathy, pure red cell aplasia, primary adrenal insufficiency, Reiter's disease, recurrent neuromyelitis optica, rheumatic heart disease, SAPHO (synovitis, acne, pustulosis, hyperostosis, and osteitis), scleroderma, secondary amyloidosis, shock lung, sciatica, secondary adrenal insufficiency, septic arthritis, seronegative arthopathy, silicone associated connective tissue disease, Sneddon-Wilkinson Dermatosis, spondilitis ankylosans, Stevens-Johnson Syndrome, systemic inflammatory response syndrome, temporal arteritis, toxoplasmic retinitis, toxic epidermal necrolysis, TRAPS (Tumor Necrosis factor receptor), type I allergic reaction, type II diabetes, urticaria, usual interstitial pneumonia, vernal conjunctivitis, viral retinitis, Vogt-Koyanagi-Harada syndrome (VKH syndrome) and wet macular degeneration.

In a twenty-fifth embodiment the invention provides a pharmaceutical composition comprising a compound of Formula (I)

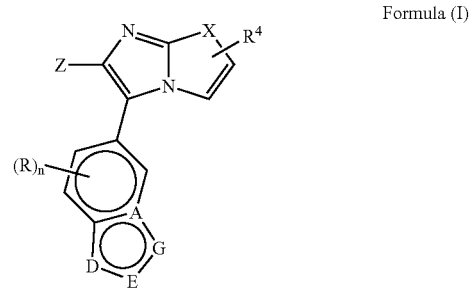

Formula (I)

and a pharmaceutically acceptable carrier or excipient, wherein

X is O or S;

A is C or N;

D is O, N or $NR^b$;

E is N or $CR^a$;

G is N, $NR^b$ or $CR^c$;

Z is selected from the optionally substituted group consisting of phenyl, naphthyl or heteroaryl;

R for each occurrence is independently H, F, Cl, or $(C_1\text{-}C_4)$alkyl;

$R^a$ is selected from the group consisting of H, $NR^2R^3$, pyridinyl and $(C_1\text{-}C_6)$alkyl;

$R^b$ is selected from the group consisting of H, —S(O)$_2$—$(C_1\text{-}C_4)$alkyl, optionally substituted $(C_1\text{-}C_6)$alkyl, optionally substituted $(C_3\text{-}C_6)$cycloalkyl, optionally substituted $(C_1\text{-}C_6)$alkyl-$R^1$, optionally substituted aryl, optionally substituted heterocyclyl and optionally substituted heteroaryl;

$R^c$ is selected from the group consisting of H, $NR^2R^3$, optionally substituted —C(O)—NH—$(C_1\text{-}C_4)$alkyl, —CO$_2$—$(C_1\text{-}C_3)$alkyl, optionally substituted $(C_1\text{-}C_6)$alkyl, optionally substituted $(C_3\text{-}C_6)$cycloalkyl, optionally substituted $(C_3\text{-}C_6)$cycloalkenyl, —$(C_1\text{-}C_6)$alkyl-$R^1$, optionally substituted phenyl, optionally substituted heterocyclyl and optionally substituted heteroaryl;

$R^1$ is selected from the optionally substituted group consisting of amino, phenyl, heteroaryl, heterocyclyl and $(C_3\text{-}C_6)$cycloalkyl;

$R^2$ and $R^3$ are independently selected from H and $(C_1\text{-}C_4)$alkyl;

$R^4$ is H, halo, CN, SO$_2$, CONH—$(C_1\text{-}C_6)$alkyl, —CO—N(CH$_3$)$_2$, —CO—N(H)-optionally substituted $(C_1\text{-}C_6)$alkyl, —CO—N(H)-optionally substituted $(C_1\text{-}C_6)$alkyl-$NR^2R^3$, —NHCO—$(C_1\text{-}C_6)$alkyl, SO$_2$—$(C_1\text{-}C_6)$alkyl, CO—$(C_1\text{-}C_6)$alkyl, CO$_2$—$(C_1\text{-}C_3)$alkyl or optionally substituted $(C_1\text{-}C_6)$ alkyl; and n is 1, 2 or 3.

DETAILED DESCRIPTION OF THE INVENTION

Protein kinases are a broad and diverse class, of over 500 enzymes, that include oncogenes, growth factors receptors, signal transduction intermediates, apoptosis related kinases and cyclin dependent kinases. They are responsible for the transfer of a phosphate group to specific tyrosine, serine or threonine amino acid residues, and are broadly classified as tyrosine and Serine/Threonine kinases as a result of their substrate specificity. Serine/Threonine Kinases (S/T kinases) are a large sub-family of protein kinases that specifically transfer a phosphate group to a terminal hydroxyl moiety of specific serine or threonine residues (Hanks et al., (1988) Science, 241: 42-52). A number of S/T kinase family members are involved in inflammatory signaling, tumor growth or cellular transformation. For example, the mitogen-activated protein kinases (MAPKs) are S/T kinases that act as intermediates within the signaling cascades of Toll like receptors (TLRs), such as TLR4, growth/survival factors, such as EGF, and death receptors, such as the TNF receptor. Activation of MAPKs, such as extracellular signal-regulated kinases (ERK1-2), p38α, c-Jun N-terminal kinase (JNK) or MAP-KAP-K2 (MK2) have been shown to transduce signaling in cells, such as monocytes/macrophages, resulting in the extra-cellular production of pro-inflammatory cytokines, such as TNF.

The p38 MAP kinase (p38, also known as CSBP or SAPK) signaling pathway has been reported to be responsible for the expression of pro-inflammatory cytokines (such as TNF, IL-1, IL-6, IL-8) that are elevated in many inflammatory and auto-immune diseases (see J. C. Lee, Nature Reviews Drug Discovery 2003, 2, 717-726 and references cited therein). This pathway has been shown to be activated by cellular stressors, such as osmotic shock, UV light, free radicals, bacterial toxins, viruses, cytokines, chemokines and in response, mediates the expression of several cytokines including, but not limited to, TNF, IL-1, IL-6 and IL-8. In cells of myeloid lineage, such as macrophages and monocytes, both IL-1 and TNFα are transcribed in response to p38 activation. Subsequent translation and secretion of these and other cytokines initiates a local or systemic inflammatory response in adjacent tissue and through infiltration of leukocytes. While this response is a normal part of the physiological response to cellular stress, acute or chronic cellular stress leads to the excess or unregulated expression of pro-inflammatory cytokines. This, in turn, leads to tissue damage, often resulting in pain and debilitation. (see G. Panayi, N Engl J Med 2001, 344(12), 907; J. Smolen Nature Reviews Drug Discovery 2003, 2, 473 and references cited therein). The four known isoforms of p38 MAP kinase (p38 α, β, γ, δ) each showing different expression levels, tissue distributions and regulation, support the concept that they are involved in the etiology of inflammatory, auto-immune and other diseases.

In summary, a number of inhibitors of p38 kinase are under active investigation for the treatment of a variety of disorders (Boehm, Adams Exp. Opin. Ther. Patents 2000, 10(1), 25-37). There remains a need for treatment in this field for compounds that are cytokine suppressive, i.e compounds that are capable of inhibiting p38 kinase.

Protein tyrosine kinases (PTKs) are enzymes that catalyse the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, Neuron 9:383-391). Aberrant or excessive PTK activity has been observed in many disease states including benign and malignant proliferative disorders as well as diseases resulting from inappropriate activation of the immune system (e.g. autoimmune disorders), allograft rejection, and graft vs. host disease. In addition, endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

Tyrosine kinases can be of the receptor-type (having extracellular, transmembrane and intracellular domains) or the non-receptor type (being wholly intracellular).

Receptor Tyrosine Kinases (RTKs) comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, Ann. Rev. Biochem. 57:433-478, 1988; Ullrich and Schlessinger, Cell 61:243-254, 1990). The intrinsic function of RTKs is activated upon ligand binding, which results in phosphorylation of the receptor and multiple cellular substrates, and subsequently in a variety of cellular responses (Ullrich & Schlessinger, 1990, Cell 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response (e.g., cell division, differentiation, metabolic effects, and changes in the extracellular microenvironment; see Schlessinger and Ullrich, 1992, Neuron 9:1-20).

Non-receptor tyrosine kinases represent a collection of cellular enzymes which lack extracellular and transmembrane sequences. Over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. The Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bohlen, 1993, Oncogene 8:2025-2031, which is incorporated herein by reference.

Many of the kinases, whether a receptor or non-receptor tyrosine kinase or a S/T kinase have been found to be involved in cellular signaling pathways involved in numerous pathogenic conditions, including immunomodulation, inflammation, or proliferative disorders such as cancer.

In a related aspect the invention provides a method for inhibiting p38 in a human subject suffering from a disorder in which p38 activity is detrimental, comprising administering to the human subject a compound of Formula (I) such that p38 activity in the human subject is inhibited and treatment is achieved.

Many autoimmune diseases and disease associated with chronic inflammation, as well as acute responses, have been linked to activation of p38 MAP kinase and overexpression or dysregulation of inflammatory cytokines. The present compounds are useful in the treatment of inflammatory disorders including, but not limited to rheumatoid arthritis, osteoarthritis, asthma, chronic obstructive pulmonary disease (COPD), sepsis, psoriasis, psoriatic arthritis, inflammatory bowel disease, Crohn's disease, lupus, multiple sclerosis, juvenile chronic arthritis, Lyme arthritis, reactive arthritis, septic arthritis, spondyloarthropathy and systemic lupus erythematosus.

The compounds of the invention are also useful in the treatment of cardiovascular disorders, such as acute myocardial infarction, acute coronary syndrome, chronic heart failure, atherosclerosis, viral myocarditis, cardiac allograft rejection, and sepsis-associated cardiac dysfunction. Furthermore, the compounds of the present invention are also useful for the treatment of central nervous system disorders such as meningococcal meningitis, Alzheimer's disease and Parkinson's disease.

The compounds of the invention are also useful in the treatment of an ocular condition, a cancer, a solid tumor, a sarcoma, fibrosarcoma, osteoma, melanoma, retinoblastoma, a rhabdomyosarcoma, glioblastoma, neuroblastoma, teratocarcinoma, an cancers such as lung, breast, stomach, bladder, colon, pancreas, ovarian, prostate and rectal cancer and hematopoietic malignancies (leukemia and lymphoma), Kaposi's sarcoma, Hodgkin's disease, lymphoma, myeloma, leukaemia, malignant ascites, hematopoietic cancers Crow-Fukase (POEMS) syndrome, a diabetic condition such as insulin-dependent diabetes mellitus glaucoma, diabetic retinopathy or microangiopathy, sickle cell anemia, chronic inflammation, synovitis, glomerulonephritis, graft rejection, Lyme disease, von Hippel Lindau disease, pemphigoid, Paget's disease, fibrosis, sarcoidosis, cirrhosis, thyroiditis, hyperviscosity syndrome, Osler-Weber-Rendu disease, chronic occlusive pulmonary disease, asthma or edema following burns, trauma, radiation, stroke, hypoxia, ischemia, ovarian hyperstimulation syndrome, preeclampsia, menometrorrhagia, endometriosis, pulmonary hypertension, infantile hemangioma, or infection by Herpes simplex, Herpes Zoster, human immunodeficiency virus, parapoxvirus, protozoa or toxoplasmosis, ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy, macular degeneration, restenosis, ischemia/reperfusion injury, vascular occlusion, carotid obstructive disease, ulcerative colitis, inflammatory bowel disease, insulin dependent diabetes mellitus, allergic diseases, dermatitis scleroderma, graft versus host disease, organ transplant rejection (including but not limited to bone marrow and solid organ rejection), acute or chronic immune disease associated with organ transplantation, sarcoidosis, disseminated intravascular coagulation, Kawasaki's disease, nephrotic syndrome, chronic fatigue syndrome, Wegener's granulomatosis, Henoch-Schoenlein purpurea, microscopic vasculitis of the kidneys, chronic active hepatitis, septic shock, toxic shock syndrome, sepsis syndrome, cachexia, infectious diseases, parasitic diseases, acquired immunodeficiency syndrome, acute transverse myelitis, Huntington's chorea, stroke, primary biliary cirrhosis, hemolytic anemia, malignancies, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, chlamydia, *yersinia* and *salmonella* associated arthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, chronic wound healing, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, acute and chronic pain (different forms of pain), Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, and diseases involving inappropriate vascularization for example diabetic retinopathy, retinopathy of prematurity, choroidal neovascularization due to age-related macular degeneration, and infantile hemangiomas in human beings. In addition, such compounds may be useful in the treatment of disorders such as ascites, effusions, and exudates, including for example macular edema, cerebral edema, acute lung injury, adult respiratory distress syndrome (ARDS), proliferative disorders such as restenosis, fibrotic disorders such as hepatic cirrhosis and atherosclerosis, mesangial cell proliferative disorders such as diabetic nephropathy, malignant nephrosclerosis, thrombotic microangiopathy syndromes, and glomerulopathies, myocardial angiogenesis, coronary and cerebral collaterals, ischemic limb angiogenesis, ischemia/reperfusion injury, peptic ulcer *Helicobacter* related diseases, virally-induced angiogenic disorders, preeclampsia, menometrorrhagia, cat scratch fever, rubeosis, neovascular glaucoma and retinopathies such as those associated with diabetic retinopathy, retinopathy of prematurity, or age-related macular degeneration. In addition, these compounds can be used as active agents against hyperproliferative disorders such as thyroid hyperplasia (especially Grave's disease), and cysts (such as hypervascularity of ovarian stroma characteristic of polycystic ovarian syndrome (Stein-Leventhal syndrome) and polycystic kidney disease since such diseases require a proliferation of blood vessel cells for growth and/or metastasis.

Compounds of formula (I) of the invention can be used alone or in combination with another therapeutic agent to treat such diseases. It should be understood that the compounds of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well known side-effects of steroid use can be reduced or even eliminated by tapering the steroid dose required when treating patients in combination with the p38 inhibitors of this invention. Non-limiting examples of therapeutic agents for rheumatoid arthritis with which a compound of formula (I) of the invention can be combined include the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, and PDGF. S/T kinase inhibitors of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7 (HUMIRA™), (U.S. Pat. No. 6,090,382), CA2 (REMICADE™), CDP 571, and soluble p55 or p75 TNF receptors, derivatives, thereof, (p75TNFR1gG (ENBREL™) or pSSTNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of formula (I) of the invention may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK or IKK inhibitors), IL-1β converting enzyme inhibitors, T-cell signalling inhibitors such as kinase inhibitors, metalloproteinase inhibitors, sulfasalazine, 6-mercaptopurines, angiotensin converting enzyme inhibitors, soluble cytokine receptors and derivatives thereof (e.g. soluble p55 or p75 TNF receptors and the derivatives p75TNFRIgG (Enbrel™ and p55TNFRIgG (Lenercept)), sIL-1RI, sIL-1RII, sIL-6R), antiinflammatory cytokines. (e.g. IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine and anti-TNF antibodies as noted above.

Non-limiting examples of therapeutic agents for inflammatory bowel disease with which a compound of formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; antibodies to or antagonists of other human cytokines or growth factors, for example, TNF, LT, IL-1, IL-2, IL-6, IL-7, IL-8, IL-12, IL-15, IL-16, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signalling by proinflammatory cytokines such as TNFα or IL-1 (e.g. IRAK, NIK or IKK inhibitors); IL-1β converting enzyme inhibitors; TNFα converting enzyme inhibitors; T-cell signalling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g. soluble p55 or p75 TNF receptors, sIL-IR1, sIL-1RII, sIL-6R) and antiinflammatory cytokines (e.g. IL-4, IL-10, IL-11, IL-13 and TGFβ). Preferred examples of therapeutic agents for Crohn's disease with which a compound of formula (I) can be combined include the following: TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)) inhibitors and PDE4 inhibitors. A compound of formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors 6-mercaptopurines; IL-11; mesalamine; prednisone; azathioprine; mercaptopurine; infliximab; methylprednisolone sodium succinate; diphenoxylate/atrop sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for multiple sclerosis with which a compound of formula (I) can be combined include the following: corticosteroids; prednisolone; methylprednisolone; azathioprine; cyclophosphamide; cyclosporine; methotrexate; 4-aminopyridine; tizanidine; interferon-β1a (AVONEX®; Biogen); interferon-β1b (BETASERON®; Chiron/Berlex); interferon α-n3) (Interferon Sciences/Fujimoto), interferon-α (Alfa Wassermann/J&J), interferon β1A-IF (Serono/Inhale Therapeutics), Peginterferon α 2b (Enzon/Schering-Plough), Copolymer 1 (Cop-1; COPAXONE®; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-12, IL-23, IL-15, IL-16, EMAP-II, GM-CSF, FGF, and PDGF. A compound of formula (I) can be combined with antibodies to cell surface molecules such as CD2, CD3, CD4, CD8, CD19, CD20, CD25, CD28, CD30, CD40, CD45, CD69, CD80, CD86, CD90 or their ligands. A compound of formula (I) may also be combined with agents such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signalling by proinflammatory cytokines such as TNFα or IL-1 (e.g. IRAK, NIK or IKK inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g. soluble p55 or p75 TNF receptors, sL-1RI, sIL-1RII, sIL-6R) and antiinflammatory cytokines (e.g. IL-4, IL-10, IL-13 and TGFβ).

Preferred examples of therapeutic agents for multiple sclerosis in which a compound of formula (I) can be combined to include interferon-β, for example, IFNβ1a and IFNβ1b; copaxone, corticosteroids, caspase inhibitors, for example inhibitors of caspase-1, IL-1 inhibitors, TNF inhibitors, and antibodies to CD40 ligand and CD80.

A compound of formula (I) may also be combined with agents, such as alemtuzumab, dronabinol, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist), MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists and IL-4 agonists.

Non-limiting examples of therapeutic agents for angina with which a compound of formula (I) of the invention can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril and bisoprolol fumarate.

Non-limiting examples of therapeutic agents for ankylosing spondylitis with which a compound of formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, prednisone, etanercept, and infliximab.

Non-limiting examples of therapeutic agents for asthma with which a compound of formula (I) can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone and metaproterenol sulfate.

Non-limiting examples of therapeutic agents for COPD with which a compound of formula (I) can be combined include the following: Letairis™ (ambrisentan)albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrineΛoratadine, terbutaline sulfate, tiotropium bromide, (R,R)-formoterol, TgAAT, cilomilast and roflumilast.

Non-limiting examples of therapeutic agents for HCV with which a compound of formula (I) can be combined include the following: Interferon-alpha-2a, Interferon-alpha-2b, Interferon-alpha con1, Interferon-alpha-n1, pegylated interferon-alpha-2a, pegylated interferon-alpha-2b, ribavirin, peginterferon alfa-2b+ribavirin, ursodeoxycholic acid, glycyrrhizic acid, thymalfasin, Maxamine, VX-497 and any compounds that are used to treat HCV through intervention with the following targets: HCV polymerase, HCV protease, HCV helicase, and HCV IRES (internal ribosome entry site).

Non-limiting examples of therapeutic agents for Idiopathic Pulmonary Fibrosis with which a compound of formula (I) can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone HCl, potassium chloride, triamcinolone acetonide, tacrolimus anhydrous, calcium, interferon-alpha, methotrexate, mycophenolate mofetil and interferon-gamma-1β.

Non-limiting examples of therapeutic agents for myocardial infarction with which a compound of formula (I) can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, and cariporide.

Non-limiting examples of therapeutic agents for psoriasis with which a compound of formula (I) can be combined include the following: calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, and sulfasalazine.

Non-limiting examples of therapeutic agents for psoriatic arthritis with which a compound of formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept and efalizumab.

Non-limiting examples of therapeutic agents for restenosis with which a compound of formula (I) can be combined include the following: sirolimus, paclitaxel, everolimus, tacrolimus, ABT-578, and acetaminophen.

Non-limiting examples of therapeutic agents for sciatica with which a compound of formula (I) can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol hcl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, and temazepam.

Preferred examples of therapeutic agents for SLE (Lupus) with which a compound of formula (I) can be combined include the following: NSAIDS, for example, diclofenac, naproxen, ibuprofen, piroxicam, indomethacin; COX2 inhibitors, for example, celecoxib, rofecoxib, valdecoxib; anti-malarials, for example, hydroxychloroquine; steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept®. A compound of formula (I) may also be combined with agents such as sulfasalazine, 5-aminosalicylic acid, olsalazine, Imuran® and agents which interfere with synthesis, production or action of proinflammatory cytokines such as IL-1, for example, caspase inhibitors like IL-1β converting enzyme inhibitors and IL-1ra. A compound of formula (I) may also be used with T cell signaling inhibitors, for example, tyrosine kinase inhibitors; or molecules that target T cell activation molecules, for example, CTLA-4-IgG or anti-B7 family antibodies, anti-PD-1 family antibodies. A compound of formula (I) can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. A compound of formula (I) may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, D2E7 (U.S. Pat. No. 6,090,382; HUMIRA™), CA2 (REMICADE™), CDP 571, TNFR-Ig constructs, (p75TNFRIgG (ENBREL™) and p55TNFRIgG (LENERCEPT™)).

In this invention, the following definitions are applicable:

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Physiologically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g. (+) or (−)-tartaric acid or mixtures thereof), amino acids (e.g. (+) or (−)-amino acids or mixtures thereof), and the like. These salts can be prepared by methods known to those skilled in the art.

Certain compounds of formula I which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of formula I and their salts may exist in more than one crystal form and the present invention includes each crystal form and mixtures thereof.

Certain compounds of formula I and their salts may also exist in the form of solvates, for example hydrates, and the present invention includes each solvate and mixtures thereof.

Certain compounds of formula I may contain one or more chiral centers, and exist in different optically active forms. When compounds of formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formula I contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of formula I and mixtures thereof.

Certain compounds of formula I may exist in different tautomeric forms or as different geometric isomers, and the present invention includes each tautomer and/or geometric isomer of compounds of formula I and mixtures thereof.

Certain compounds of formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of formula I and mixtures thereof.

Certain compounds of formula I may exist in zwitterionic form and the present invention includes each zwitterionic form of compounds of formula I and mixtures thereof.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents (e.g., —$(CH_2)C(O)_2H$ or a moiety that contains a carboxylic acid) wherein the free hydrogen is replaced by $(C_1-C_4)$alkyl, $(C_2-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)-alkylcarbamoyl-($C_1$-$C_2$)alkyl and piperidino-, pyrrolidino- or morpholino($C_2$-$C_3$)alkyl.

Other exemplary pro-drugs release an alcohol of Formula I wherein the free hydrogen of the hydroxyl substituent (e.g., $R^1$ contains hydroxyl) is replaced by ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylamino-methyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

The term "heterocyclic" or "heterocyclyl", as used herein, include non-aromatic ring systems, including, but not limited to, monocyclic, bicyclic and tricyclic rings, which can be completely saturated or which can contain one or more units of unsaturation, for the avoidance of doubt, the degree of unsaturation does not result in an aromatic ring system) and have 3 to 12 atoms including at least one heteroatom, such as nitrogen, oxygen, or sulfur. For purposes of exemplification, which should not be construed as limiting the scope of this invention, the following are examples of heterocyclic rings: azepines, azetidinyl, morpholinyl, oxopiperidinyl, oxopyrrolidinesyl, piperazinyl, piperidinyl, pyrrolidinyl, quinicludinyl, thiomorpholinyl, tetrahydropyranyl and tetrahydrofuranyl.

The term "heteroaryl" as used herein, include aromatic ring systems, including, but not limited to, monocyclic, bicyclic and tricyclic rings, and have 3 to 12 atoms including at least one heteroatom, such as nitrogen, oxygen, or sulfur. For purposes of exemplification, which should not be construed as limiting the scope of this invention, heteroaryls include: azaindolyls, benzo(b)thienyls, benzimidazolyls, benzofuranyls, benzoxazolyls, benzothiazolyls, benzothiadiazolyls, benzoxadiazolyls, furanyls, imidazolyls, imidazopyridinysl, indolyls, indolinyls, indazolyls, isoindolinyl, isoxazolyls, isothiazolyls, oxadiazolyls, oxazolyls, purinyls, pyranyls, pyrazinyls, pyrazolyls, pyridinyls, pyrimidinyls, pyrrolyls, pyrrolo[2,3-d]pyrimidinyls, pyrazolo[3,4-d]pyrimidinyls, quinolinyls, quinazolinyls, triazolyls, thiazolyls, thiophenyl, tetrahydroindolyl, tetrazolyls, thiadiazolyls, thienyls, thiomorpholinyls, triazolyls or tropanyl.

When the term "substituted heterocyclic" (or heterocyclyl) or "substituted heteroaryl" is used, what is meant is that the heterocyclic group is substituted with one or more substituents that can be made by one of ordinary skill in the art and results in a molecule that is a kinase inhibitor. For purposes of exemplification, which should not be construed as limiting the scope of this invention, preferred substituents for the heterocycle of this invention are each independently selected from the optionally substituted group consisting of alkenyl, alkoxy, alkoxyalkoxy, alkoxyalkyl, alkoxycarbonyl, alkoxycarbonylheterocycloalkoxy, alkyl, alkylcarbonyl, alkylester, alkyl-O—C(O)—, alkyl-heterocyclyl, alkyl-cycloalkyl, alkyl-nitrile, alkynyl, amido groups, amino, aminoalkyl, aminocarbonyl, carbonitrile, carbonylalkoxy, carboxamido, $CF_3$, CN, —C(O)OH, —C(O)H, —C(O)—C($CH_3$)$_3$, —OH, —C(O)O-alkyl, —C(O)O-cycloalkyl, —C(O)O-heterocyclyl, —C(O)-alkyl, —C(O)-cycloalkyl, —C(O)-heterocyclyl, cycloalkyl, dialkylaminoalkoxy, dialkylaminocarbonylalkoxy, dialkylaminocarbonyl, halogen, heterocyclyl, a heterocycloalkyl group, heterocyclyloxy, hydroxy, hydroxyalkyl, nitro, $OCF_3$, oxo, phenyl, —$SO_2CH_3$, —$SO_2CR_3$, tetrazolyl, thienylalkoxy, trifluoromethylcarbonylamino, trifluoromethylsulfonamido, heterocyclylalkoxy, heterocyclyl-S(O)$_p$, cycloalkyl-S(O)$_p$, alkyl-S—, heterocyclyl-S, heterocycloalkyl, cycloalkylalkyl, heterocycolthio, cycloalkylthio, —$Z^{105}$—C(O)N(R)$_2$, —$Z^{105}$—N(R)—C(O)—$Z^{200}$, —$Z^{105}$—N(R)—S(O)$_2$—$Z^{200}$, —$Z^{105}$—N(R)—C(O)—N(R)—$Z^{200}$, —N(R)—C(O)R, —N(R)—C(O)OR, OR—C(O)-heterocyclyl-OR, $R_c$ and —$CH_2OR_c$;

wherein $R_3$ is $C_1$-$C_4$ alkyl, $C_3$-$C_6$ cycloalkyl or phenyl;

wherein p is 0, 1 or 2;

where $R_c$ for each occurrence is independently hydrogen, optionally substituted alkyl, optionally substituted aryl, —($C_1$-$C_6$)—$NR_dR_e$, -E-(CH$_2$)$_t$—$NR_dR_e$, -E-(CH$_2$)$_t$—O-alkyl, -E-(CH$_2$)$_t$—S-alkyl, or -E-(CH$_2$)$_t$—OH;

wherein t is an integer from about 1 to about 6;

$Z^{105}$ for each occurrence is independently a covalent bond, alkyl, alkenyl or alkynyl; and $Z^{200}$ for each occurrence is independently selected from an optionally substituted group selected from the group consisting of alkyl, alkenyl, alkynyl, phenyl, alkyl-phenyl, alkenyl-phenyl or alkynyl-phenyl;

E is a direct bond, O, S, S(O), S(O)$_2$, or $NR_f$, wherein $R_f$ is H or alkyl and $R_d$ and $R_e$ are independently H, alkyl, alkanoyl or $SO_2$-alkyl; or $R_d$, $R_e$ and the nitrogen atom to which they are attached together to form a five- or six-membered heterocyclic ring.

An "heterocycloalkyl" group, as used herein, is a heterocyclic group that is linked to a compound by an aliphatic group having from one to about eight carbon atoms. For example, heterocycloalkyl group is a morpholinomethyl group.

As used herein, "alkyl" means $C_1$-$C_8$ and includes straight chained or branched hydrocarbons, which are completely saturated. Preferred alkyls are methyl, ethyl, propyl, butyl, pentyl, hexyl and isomers thereof. As used herein, "alkenyl" and "alkynyl" means $C_2$-$C_8$ and includes straight chained or branched hydrocarbons which contain one or more units of unsaturation, one or more double bonds for alkenyl and one or more triple bonds for alkynyl.

As used herein, aromatic groups (or aryl groups) include aromatic carbocyclic ring systems (e.g. phenyl and cyclopentyldienyl) and fused polycyclic aromatic ring systems (e.g. naphthyl, biphenylenyl and 1,2,3,4-tetrahydronaphthyl).

As used herein, cycloalkyl means $C_3$-$C_{12}$ monocyclic or multicyclic (e.g., bicyclic, tricyclic, etc.) hydrocarbons that is completely saturated or has one or more unsaturated bonds but does not amount to an aromatic group. Preferred examples of a cycloalkyl group are cyclopropyl, cyclobutyl, cyclopentyl, cyclopentenyl, cyclohexyl and cyclohexenyl.

As used herein, many moieties or substituents are termed as being either "substituted" or "optionally substituted". When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: alkenyl groups, alkoxy group (which itself can be substituted, such as —O—$C_1$-$C_6$-alkyl-OR, —O—$C_1$-$C_6$-alkyl-N(R)$_2$, and $OCF_3$), alkoxyalkoxy, alkoxycarbonyl, alkoxycarbonylpiperidinyl-alkoxy, alkyl groups (which itself can also be substituted, such as —$C_1$-$C_6$-alkyl-OR, —$C_1$-$C_6$-alkyl-N(R)$_2$, and —$CF_3$), alkylamino, alkylcarbonyl, alkylester, alkylnitrile, alkylsulfonyl, amino, aminoalkoxy, $CF_3$, COH, COOH, CN, cycloalkyl, dialkylamino, dialkylaminoalkoxy, dialkylaminocarbonyl, dialkylaminocarbonylalkoxy, dialkylaminosulfonyl, esters (—C(O)—OR, where R is groups such as alkyl, heterocycloalkyl (which can be substituted), heterocyclyl, etc., which can be substituted), halogen or halo group (F, Cl, Br, I), hydroxy, morpholinoalkoxy, morpholinoalkyl, nitro, oxo, $OCF_3$, optionally substituted phenyl, $S(O)_2CH_3$. $S(O)_2CF_3$, and sulfonyl, N-alkylamino or N,N-dialkylamino (in which the alkyl groups can also be substituted).

As used herein, the term "N-oxide" means $N^+O^-$.

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted, 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 pl). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the preceding Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

| Parts by weight | |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deletrious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

Enzyme Assays

The in vitro potency of compounds of formula (I) in inhibiting one or more of the protein kinases discussed herein or described in the art may be determined by the procedures detailed below.

The potency of compounds of formula (I) can be determined by the amount of inhibition of the phosphorylation of an exogenous substrate (e.g., a synthetic peptide (Z. Songyang et al., *Nature*. 373:536-539) by a test compound relative to control.

p38 kinase Assay

Materials: Active p38α enzyme can be purchased from Upstate Biotechnology Inc. (UBI). Anti-phospho-MBP specific antibody can be purchased from UBI and Europium (Eu)-cryptate labeled by Cis-Bio International. SAXL (streptavidine linked XL) can be obtained for Prozyme. Biotin-MBP-peptide (Biot-Ahx-VHFFKNIVTPRTP-PPSQGKGAEGQR-OH) can be made by New England Peptide. HTRF reader RUBYstar was can be acquired from BMG Labtech.

The kinase assay is performed using the homogenous time-resolved fluorescence (HTRF) method (Mabile, 1991; Mathis, 1993). The assay mixture contains 7.8 nM p38α, 0.5 µM biotin-MBP-peptide, 0.1 mM ATP and compound (to a final 5% DMSO) in a buffer containing 20 mM MOPS pH 7.2, 10 mM MgCl$_2$, 5 mM EGTA, 5 mM β-phosphoglycerol, 1 mM Na$_3$VO$_4$, 0.01% Triton-X-100, 1 mM DTT. The reaction is carried out at room temperature in 96 half-well black plates (Corning). At designated time point, EDTA (to a final 0.1 M) is added to quench the reaction. The products are detected by addition of the revelation reagents (to a final 11 ng anti-phospho-MBP-Eu antibody and 0.34 μg SAXL). The plates are incubated in dark at 4° C. overnight, and read in the HTRF reader RUBYstar. The ratio between the signal at 620 nm and 665 nm at various inhibitor concentrations is used to calculate the IC$_{50}$.

REFERENCES (1) M. Mabile, G. Mathis, E. J. P., Jolu, D. Pouyat, C. Dumont, Patent WO 92:13264, 1991
(2) G. Mathis, Clin. Chem. 39 (1993) 1953-1959

Methods

Kinase assays: The kinase assays were performed using the homogenous time-resolved fluorescence (HTRF) method (Mabile, et al.; Mathis, et al.). IKKα and IKKβ (made in house) assay contained either 6.7 nM IKKα or 1.7 nM IKKβ, 0.5 μM biotin-IκBα-peptide (Cell Signaling), 0.01 mM ATP and compound in IKK buffer (20 mM MOPS pH 7, 10 mM MgCl$_2$, 5 mM EGTA, 5 mM β-phosphoglycerol, 1 mM Na$_3$VO$_4$, 0.01% Triton-X-100, 1 mM DTT, 5% DMSO). p38α and CDK2 (UBI) assays contained either 7.8 nM p38α or 2.7 nM CDK2/cyclin A, and 0.5 μM biotin-MBP-peptide, 0.1 mM ATP and compound in the IKK Buffer. p38β assay contained 0.3 nM p38β, and 0.1 μM biotin-MBP-protein (UBI), 0.1 mM ATP and compound in the IKK Buffer. JNK1, JNK2 and JNK3 assays contained either 11.1 nM JNK1, 7.6 nM JNK2, or 2.4 nM JNK3, 1 μM biotin-ATF2-peptide (Cell Signaling), 0.01 mM ATP and compound in the IKK Buffer. KDR (make in house) assay contained 4.0 nM KDR, 2 μM biotin-FGFR-peptide, 0.1 mM ATP and compound in a buffer containing 50 mM HEPES, pH 7.1, 10 mM MgCl$_2$, 2 mM MnCl$_2$, 2.5 mM DTT, 0.01% BSA, 0.1 mM Na$_3$VO$_4$ and 5% DMSO. JAK1 (make in house) assay contained 3.6 nM JAK1, 2 μM biotin-FGFR-peptide, 0.001 mM ATP and compound in a buffer containing 50 mM MOPSO, pH 6.5, 10 mM MgCl$_2$, 2 mM MnCl$_2$, 2.5 mM DTT, 0.01% BSA, 0.1 mM Na$_3$VO$_4$ and 5% DMSO. All assays were carried out at RT for 60 min and stopped by addition of EDTA. The products were detected by addition of revelation reagents containing Europium labeled phospho-specific antibodies and SAXL. The plates were incubated in dark at 4° C. overnight, and read in the HTRF reader RUBYstar (BMG)

REFERENCES (3) M. Mabile, G. Mathis, E. J. P., Jolu, D. Pouyat, C. Dumont, Patent WO 92/13264, 1991
(4) G. Mathis, Clin. Chem. 39 (1993) 1953-1959

Cellular Assays

THP-1 cells from ATCC (TIB-202) are serum-starved and seeded at a density of 2×10$^5$/well in 100 μL of low serum RPMI media (0.5% FBS). 50 μl samples of compounds in appropriate serial dilutions are added to the wells. Compound stocks and dilutions in 100% DMSO are prepared such that final concentration of DMSO in RPMI media is 0.5%. Cells and compounds or controls are pre-incubated for 1 hour in a 37° C. incubator.

Cytokine release and P-Hsp27 induction is stimulated by LPS treatment. LPS (Sigma, L-4516) is reconstituted to a concentration of 1 mg/ml in endotoxin free dIH$_2$O, diluted in RPMI media such that 50 μl/well is added to each well for a final concentration of 1 μg/ml (excepting negative control wells). Plates with cells, compound and LPS are incubated at 37° C. for 45 minutes. This time point needs recalibration when new THP-1 cells are thawed.

For analysis of P-Hsp27 (phosphorylated Hsp27 protein), plates are vacuum filtered to remove media and compounds. Cells are washed twice with buffer (UBI, Assay Buffer #1, 43-010) using vacuum filtration. Then, 100 μl of cell lysis buffer (Biorad, 171-304011) is added per well and the plate is covered and shaken for 20 mins at 4° C. to lyse cells. Lysates are directly transferred to a flat bottom 96 well plate for analysis or stored frozen at −20° C. until analysis. Lysates are diluted 1:2 with assay buffer #1 and analysed by the Luminex method on a Bio-Plex machine following manufacturers directions (UBI, Phospho-HSP27 Beadmates kit, 46-607).

For analysis of cytokine release, plates are spun after incubation with LPS for 5 min at 1000 rpm and 100 μl of supernatant media is directly transferred to a 2$^{nd}$ 96 well plate. Test plate with cells is returned to incubator O/N to be assayed for toxicity the next day (see below). Supernatant is stored at −20° C. until analysis. Supernatant media sample plates are analyzed in a standard ELISA format following manufacturers instructions (R&D, huTNFα ELISA assay kit). Toxicity analysis is done after the overnight incubation with compound. 50 μl of a 2.5 mg/ml solution of MTT (Sigma, M 2128) is added to cells. Plate is incubated at 37° C. for 3 hrs. 50 μl of 20% SDS is then added to solubilize the formazen dye. Plates are incubated at 37° C. for an additional 3 hrs and OD570 is measured on a spectrophotometer.

Materials:

Blood donors are in-house volunteers. Tubes used for drawing blood are 3.2% Buffered Sodium Citrate from Monoject, Mansfield, Mass., Catalog Number 340486. Dilution Plates and Assay Plates were from Corning, COSTAR Catalogs Numbers 3365 and 3599, respectively. Dimethyl sulphoxide (DMSO) was from Sigma, St. Louis, Mo., Catalog Number D2650. RPMI Media 1640 and HEPES Buffer Solution (1M) are from Invitrogen GIBCO Cell Culture Systems, Carlsbad, Calif., Catalog Numbers 11875 and 15630. Lipopolysaccharides from *Escherichia coli* 0127:B8 (LPS) was from Sigma, Catalog Number L4516. Tumor Necrosis Factor Alpha (TNF-α/TNFSF1A) ELISA kits were from R&D Systems, Inc., Minneapolis, Minn., Catalog Number PDTAOOC.

Methods:

Blood is drawn from healthy donors into sodium citrate tubes within 1 hour of assay. Drugs were prepared in Dimethyl sulphoxide (DMSO) and serial dilute (1:3) with DMSO in Dilution Plate(s) to give 8 dilution points for each compound tested. Further dilution (1:100) of drug was made into RPMI Media 1640, 20 mM HEPES. Into wells of 96-well Assay Plate(s), 100 μL/well of diluted drug or control (1% DMSO in RPMI Media 1640, 20 mM HEPES) and 80 μL of blood is applied and pre-incubated for 30 minutes in an incubator set at 37 degrees centigrade. Tumor Necrosis Factor Alpha (TNF-α) is then stimulated with the addition of Lipopolysaccharides from *Escherichia coli* 0127:B8 (LPS, 50 ng/ml) for 3.5 hours at 37 degrees centigrade. Plates are spun at 183 g (1000 rpm in Beckman/Coulter Allegra 6KR centrifuge) for 10 minutes. Cell-free supernatant (75 μL/well) was collected and TNF-α is measured by commercial ELISA kit, following protocol of manufacturer. Potency of drug to inhibit TNF-α in vitro is determined the percent reduction of measured TNF-α in wells with drug compared to control wells without drug.

Results are represented as $IC_{50}$ values. Reference: Current Protocols in Immunology (2005) 7.18B-7.18B12.

LPS-Induced TNF Production In Vivo

Materials:

Lipopolysaccharide (LPS) from *Escherichia coli*, serotype 0111:B4 (Sigma, cat #L-4130, lot #095K4056)

Phosphate Buffered Saline pH 7.2 (Gibco)

PEG 200 (Sigma, cat #P3015)

Methylcellulose (Sigma, cat #M7027)

Male Lewis rats, 200-300 g (Charles River Laboratories)

Rat Tumor Necrosis Factor α (TNFα) ELISA kit (R&D Systems cat #RTA00)

Methods:

The test compound is prepared into vehicle (5% PEG 200, in 0.5% Methylcellulose) at the desired concentrations for dosing (1, 3, 10, 30, 100 mg/kg). Lewis rats are pre-dosed with the compound(s) either intraperitoneally (i.p.) or orally (p.o.) at 0.002 ml/gram body weight one-two hours prior to the LPS challenge. Negative control includes rats treated with vehicle (5% PEG 200, in 0.5% Methylcellulose) alone. LPS is dissolved in phosphate buffered saline, sonicated and the rats are injected with 1 mg/kg intravenously (i.v.) at 0.001 ml/gram body weight. One hour after the LPS challenge the rats are cardiac bled and the serum is analyzed for TNFα by ELISA. The compound concentration is also determined in the serum.

The average concentration of TNFα in the vehicle treated group is taken as a maximal (100 percent) response. The mean TNFα levels in the compound treated groups are expressed as a percent of the maximal response. The percent of maximal TNFα responses at various doses or serum concentrations of the compound(s) are further analyzed using a four parameter curve fit of logarithmically transformed data (Graphpad Prism 4 software) to generate $ED_{50}$ and $EC_{50}$.

RELEVANT REFERENCE(S)

Azab A, et al. (1998). *Life Sci.* 63: 323-327.
Martinez E F, et. al (2004) *Biochem. Phamma.* 68:1321-1329.

The teachings of all references, including journal articles, patents and published patent applications, are incorporated herein by reference in their entirety.

Compounds of the invention may be prepared using the synthetic transformations illustrated in Scheme 1. Starting materials are commercially available or may be prepared by the procedures described herein or by procedures that would be well known to one skilled in the art of organic chemistry. Methods for preparing imidazothiazole (X=S) or imidazooxazole (X=O) compounds of the invention are illustrated in Scheme I. In Scheme I, step a, a suitably substituted imidazothiazole (X=S) or imidazooxazole (X=O) 1 (prepared by methods known in the literature, such as WO2004110990A2) is halogenated using methods known to one skilled in the art (see, for example, Larock, R. C. "Comprehensive Organic Transformations: A Guide to Functional Group Preparations, $2^{nd}$ edition", 1999, Wiley-VCH or General Procedure A below). The resulting product 2 may be further reacted in a number of ways. For example, Suzuki reaction (step b) with a boronate or boronic acid 3 may directly give compounds 4. The boronate or boronic acid 3 may be commercially available, known in the literature, or prepared using transformations described herein (see, for example, General Procedure B). Conditions for the Suzuki reaction are well known to one skilled in the art (see, for example, General Procedure C). Further functionalization of compound 4 can be performed, if desired, using reactions known to one skilled in the art (see, for example, Larock, R. C. above). For example, formation of amides, ureas, or sulfonamides can be achieved by reaction of compound 4 containing a primary or secondary amine. Also, deprotection of compound 4 to yield an unprotected compound can be performed using conditions such as those described in Greene, T. W. and Wuts, P. G. M. "Protective Groups in Organic Synthesis, $3^{rd}$ Edition", 1999, Wiley-Interscience. For example, a protecting group such as a t-butoxycarbonyl group can be removed from a protected amine to yield the unprotected amine and the deprotected compound 4 may then be reacted further as described above.

Compounds of the invention may also be prepared by Suzuki reaction of compound 2 with optionally substituted 2-(3-fluoro-4-nitrophenyl)-4,4,5,5-tetramethyl-[1,3,2]dioxaborolane to give compound 5 (step c). Reaction of compound 5 with an amine in a suitable organic solvent (such as ACN, THF, n-PrOH, or IPA, preferably ACN) and optionally a base (such as TEA, DIEA) gives compound 6 (see, for example, General Procedure D). The reduction of the nitro compound 6 to diamine 7 may be accomplished via catalytic hydrogenation (see, for example, General Procedure E), reaction with tin(II) chloride (see, for example, General Procedure F) or other ways known in the literature (see, for example, Larock, R. C. above). The diamine 7 can be cyclized using cyanogen bromide (see, for example, General Procedure G), sodium nitrite (see, for example, General Procedure H) or other ways known in the literature. Further functionalization of compound 8 can be performed, if desired, using reactions known to one skilled in the art (see, for example, Larock, R. C. above). For example, formation of amides, ureas, or sulfonamides can be achieved by reaction of compound 8 containing a primary or secondary amine. Also, deprotection of compound 8 to yield an unprotected compound can be performed using conditions such as those described in Greene, T. W. and Wuts, P. G. M. (see above). For example, a protecting group such as a t-butoxycarbonyl group can be removed from a protected amine to yield the unprotected amine and the deprotected compound 8 may then be reacted further as described above.

Compounds of the invention may also be prepared by Suzuki reaction of compound 2 with optionally substituted 6-fluoropyridin-3-ylboronic acid to give compound 9 (step g). Reaction of compound 9 with optionally substituted hydrazine either neat or in a suitable organic solvent (such as ACN, THF, n-PrOH, or IPA, preferably n-PrOH) gives compound 10 (step h).

The versatile intermediate 10 may be reacted further in a variety of ways. For example in step i, the reaction of compound 10 with an acid chloride, either commercially available or prepared from a carboxylic acid (using conditions such as those described in Larock, R. C. above), to give compound 11 directly (see, for example, General Procedure I). Additionally, compound 10 may be reacted with a carboxylic acid or an acid chloride (step j) to form an amide 12 (using conditions such as those described in Larock, R. C. above). Amide 12 is then reacted with thionyl chloride (step k) to give compound 11 (see, for example, General Procedure J). Also, compound 10 may be reacted with an aldehyde (step 1) to form hydrazone 13 (using conditions such as those described in Larock, R. C. above). Hydrazone 13 is then cyclized using iodobenzene diacetate (step m) as described in General Procedure K to give compound 11. Further functionalization of compound 11 can be performed, if desired, using reactions known to one skilled in the art (see, for example, Larock, R. C. above). For example, formation of amides, ureas, or sulfonamides can be achieved by reaction of compound 11 containing a primary or secondary amine. Also, deprotection of compound 11 to yield an unprotected compound can be performed using conditions such as those described in Greene, T. W. and Wuts, P. G. M. (see above). For example, a protecting group such as a t-butoxycarbonyl group can be removed from a protected amine to yield the unprotected amine and the deprotected compound 11 may then be reacted further as described above.

If the suitably substituted imidazothiazole (X=S) or imidazooxazole (X=O) is not reported in the literature, then one skilled in the art can prepare these compounds using conditions such as those described in the literature (WO2004110990A2) for known imidazothiazoles (X=S) or imidazooxazoles (X=O) as shown in Scheme II herein. The starting ketones are commercially available or can be prepared by one skilled in the art. An α-bromoketone 15 (step n) can be prepared using conditions known in the literature (see Larock, R. C. above) from a ketone 14 and a brominating agent (see, for example, General Procedure N). The α-bromoketone 15 can subsequently be reacted (step o) with a suitably substituted 2-aminooxazole 16 to give a 2-substituted oxazol-2(3H)-imine intermediate 17 which is then treated (step p) with a dehydrating reagent (see, for example, General Procedure O) to give the desired imidazothiazole (X=S) or imidazooxazole (X=O), compound 1. In some cases there can be additional functional group modification of the $R^4$, $R^b$ and $R^c$ substituents at any stage of the synthetic sequence. These modifications may include and are not limited to amide bond formation (see, for example, General Procedure P) or the reductive amination of an amine (see, for example, General Procedure R). Conditions used for these transformations are know to those skilled in the art and can be found in the literature (Larock, R. S. above)

Scheme I:

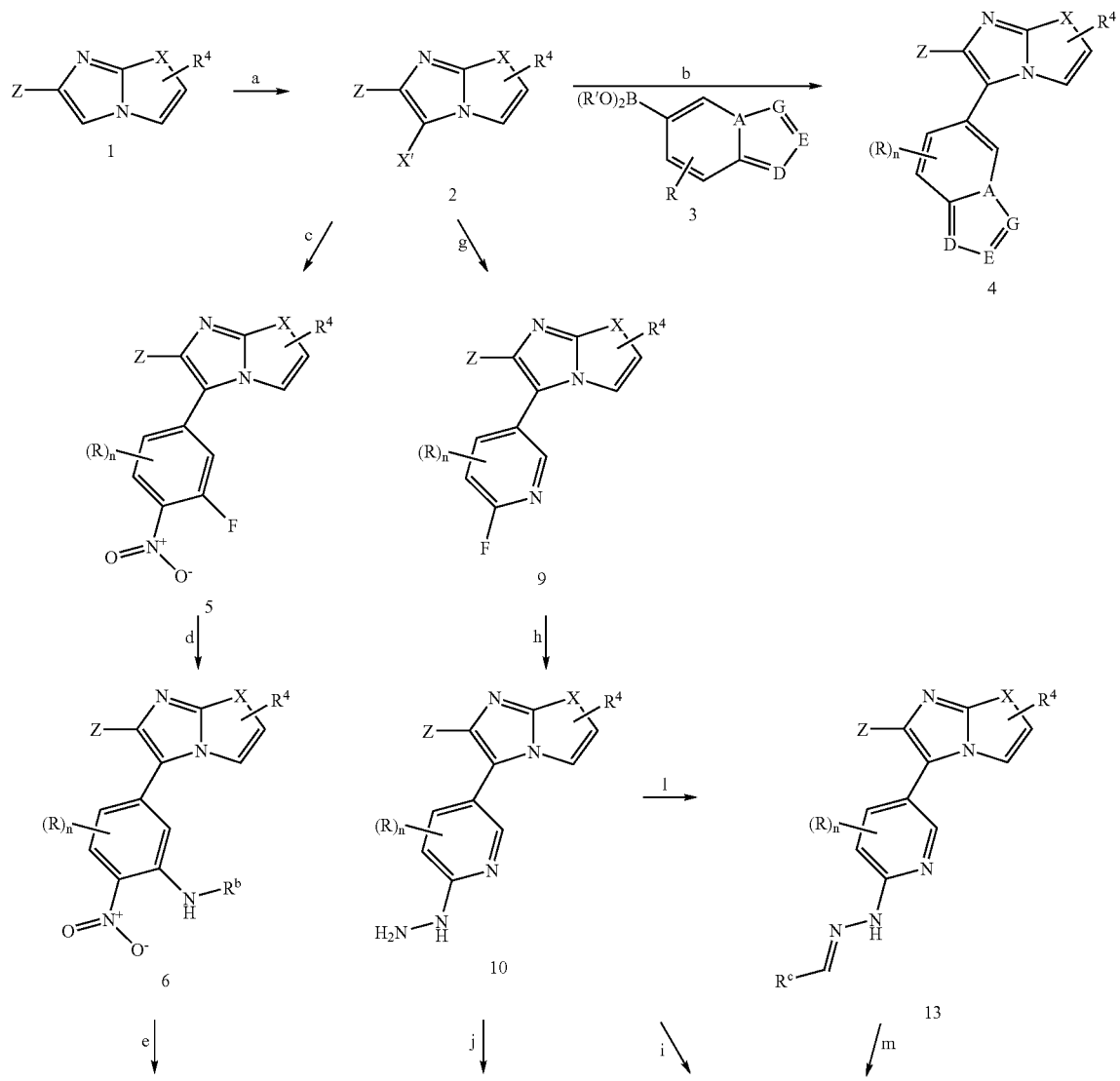

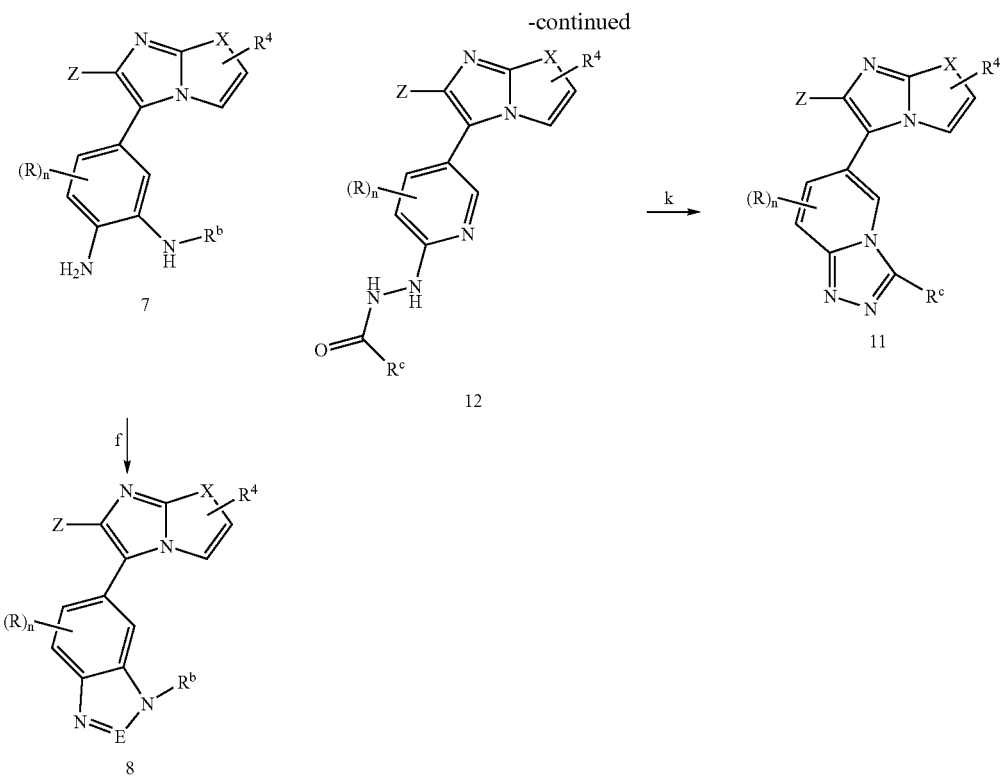

Scheme II:

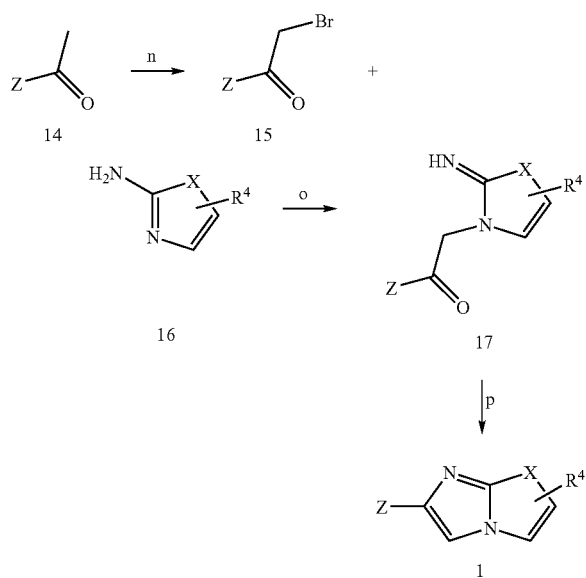

Abbreviations
ACN Acetonitrile
Boc tert-Butoxycarbonyl
Bop-Cl Bis(2-oxo-3-oxazolidinyl)phosphinic chloride
DCC N,N'-Dicyclohexylcarbodiimide
DCE 1,2-Dichloroethane
DCM Dichloromethane (methylene chloride)
DIEA N,N-Diisopropylethylamine
DME 1,2-Dimethoxyethane
DMF N,N-Dimethylformamide
DMSO Dimethyl sulfoxide
dppf 1,1'-Bis(diphenylphosphino)ferrocnene
EDCI 1-(3-Dimethylaminopropyl)-3-ethylcarbodiimide
equiv Equivalent (molar equivalent)
EtOAc Ethyl acetate
EtOH Ethyl alcohol
Et$_2$O Diethyl ether
HATU O-(7-Azabenzotriazol-1-yl)-N,N,N',N'-tetramethyluronium hexafluorophosphate
HBTU O-Benzotriazol-1-yl-N,N,N',N'-tetramethyluronium hexafluorophosphate
HOAc Acetic acid
HOAT 1-Hydroxy-7-azabenzotriazole
HOBT 1-Hydroxybenzotriazole
HPLC High-pressure liquid chromatography
IBCF Isobutyl chloroformate
IPA Isopropyl alcohol
KOAc Potassium acetate
LAH Lithium aluminum hydride
LC/MS Liquid chromatography/Mass spectroscopy
MeI Methyl iodide
MeOH Methyl alcohol
NBS N-Bromosuccinimide
NIS N-Iodosuccinimide
NMP N-Methylpyrrolidinone
NMR Nuclear magnetic resonance
PCC Pyridinium chlorochromate
PdCl$_2$(PPh$_3$)$_2$ bis(triphenylphosphine)palladium(II) chloride
n-PrOH n-Propyl alcohol
RP-HPLC Reverse-phase high-pressure liquid chromatography R*t*, Retention time
TBAF Tetrabutylammonium fluoride
TEA Triethylamine
TFA Trifluoroacetic acid
THF Tetrahydrofuran

GENERAL PROCEDURES AND EXAMPLES

The general synthetic schemes that were utilized to construct the majority of compounds disclosed in this application are described below in Schemes 1-17.

Scheme 1. Halogenation of an imidazo
[2,1-b]thiazole or an imidazol[2,1-b] oxazole (General Procedure A)

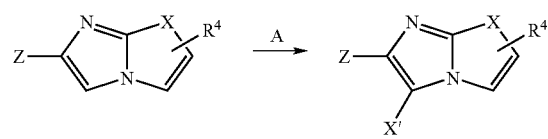

Scheme 2. Formation of a boronate
from an aryl or heteroaryl halide (General Procedure B)

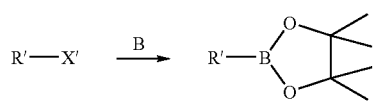

Scheme 3. Suzuki coupling of a boronate or
boronic acid with an aryl or heteroaryl halide (General Procedure C)

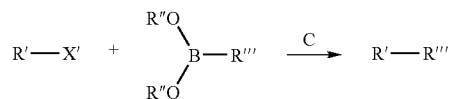

Scheme 4. Displacement of an aryl or heteroaryl
halide with an amine or hydrazine (General Procedure D)

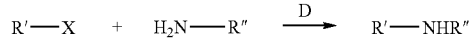

Scheme 5. Reduction of a nitro group to an
aniline via hydrogenation (General Procedure E)

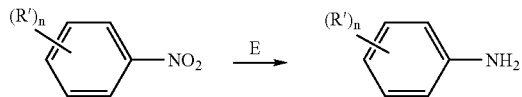

Scheme 6. Reduction of a nitro group to an
aniline using tin(II) chloride (General Procedure F)

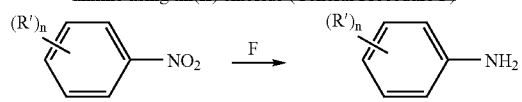

Scheme 7. Cyclization of a diamine with
cyanogen bromide (General Procedure G)

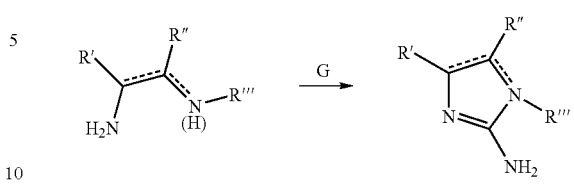

Scheme 8. Cyclization of a diamine
with sodium nitrite (General Procedure H)

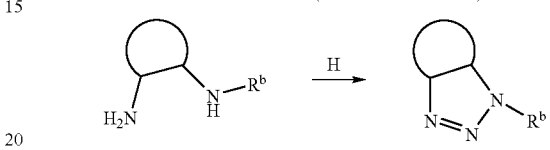

Scheme 9. Cyclization of a pyridin-2-ylhydrazine
with an acid chloride (General Procedure I and I.1)

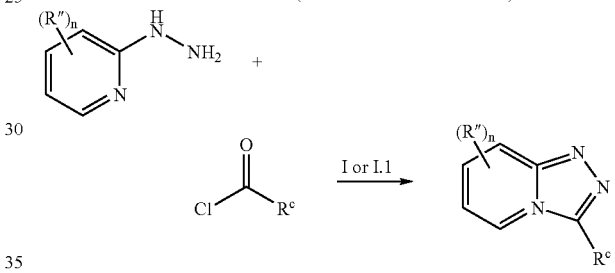

Scheme 10. Amide formation followed by
cyclization with thionyl chloride (General Procedure J and J.1)

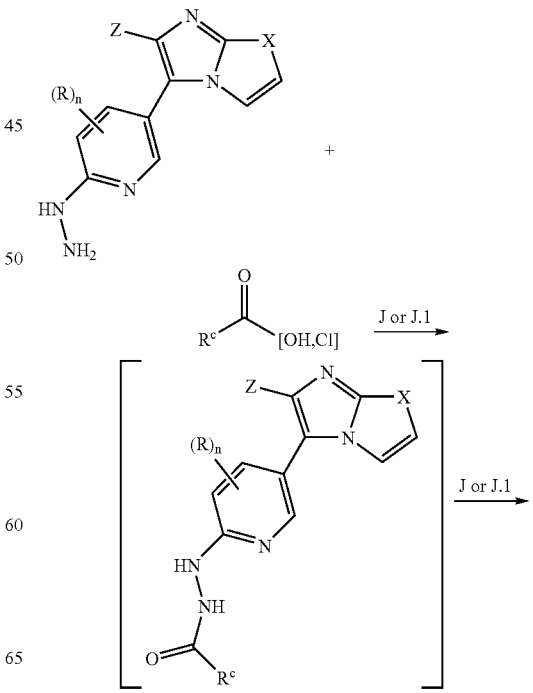

-continued

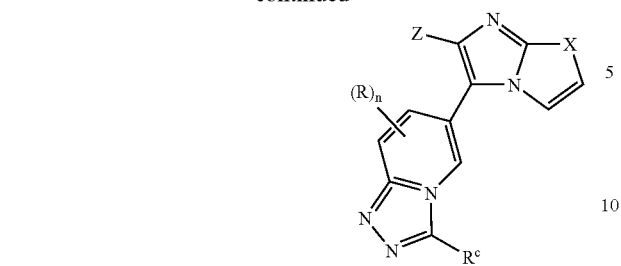

Scheme 11. Hydrazone formation followed by
cyclization with iodobenzene diacetate (General Procedure K and K.1)

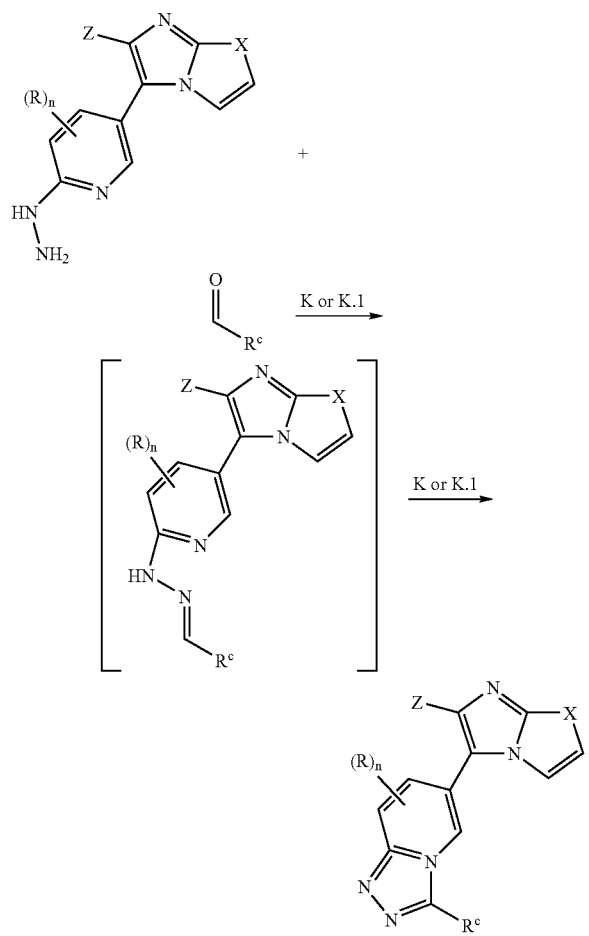

Scheme 12. Carbonylation of an aromatic halide (General Procedure L)

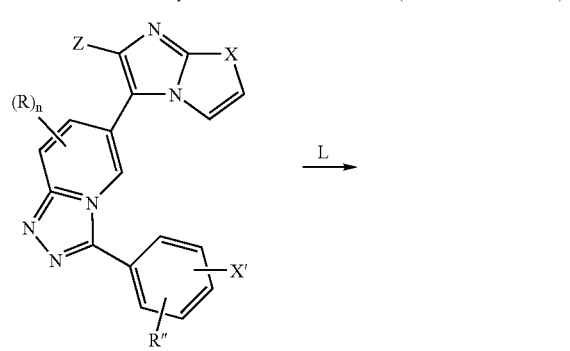

-continued

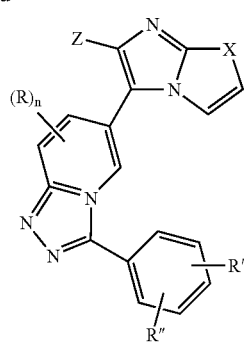

Scheme 13. Acidic cleavage of a
Boc-protected amine (General Procedure M and M.1)

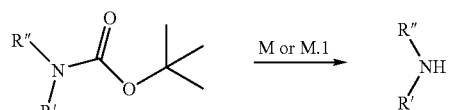

Scheme 14. Halogenation of a ketone with bromine (General Procedure N)

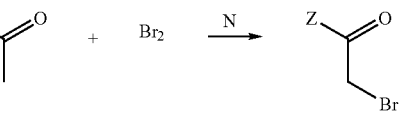

Scheme 15. Cyclization to form an
imidazo[1,2-b]oxazole (General Procedure O)

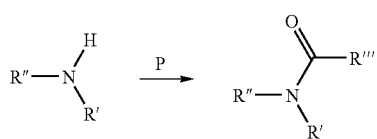

Scheme 16. Amide bond formation (General Procedure P)

Scheme 17. Reductive amination with formaldehyde (General Procedure Q)

-continued

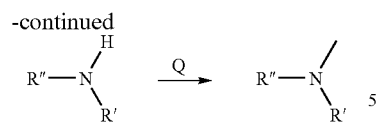

List of General Procedures

General Procedure A Halogenation of an imidazo[2,1-b]thiazole or an imidazo[2,1-b]oxazole
General Procedure B Formation of a boronate from an aryl or heteroaryl halide
General Procedure C Suzuki coupling of a boronate or boronic acid with an aryl or heteroaryl halide
General Procedure D Displacement of an aryl or heteroaryl halide with an amine or hydrazine
General Procedure E Reduction of a nitro group to an aniline via hydrogenation General Procedure F Reduction of a nitro group to an aniline using tin(II) chloride
General Procedure G Cyclization of a diamine with cyanogen bromide
General Procedure H Cyclization of a diamine with sodium nitrite
General Procedure I and I.1 Cyclization of a pyridin-2-ylhydrazine with an acid chloride
General Procedure J and J.1 Amide formation followed by cyclization with thionyl chloride
General Procedure K and K.1 Hydrazone formation followed by cyclization with iodobenzene diacetate
General Procedure L Carbonylation of an aromatic halide
General Procedure M and M.1 Acidic cleavage of a Boc-protected amine
General Procedure N Halogenation of a ketone with bromine
General Procedure O Cyclization to form an imidazo[1,2-b]oxazole
General Procedure P Amide bond formation
General Procedure Q Reductive amination with formaldehyde The following examples are ordered according to the final general procedure used in their preparation. A capital letter in bold refers to the General Procedure used. References to example or preparation numbers refer to examples and preparations described herein. The synthetic routes to any novel intermediates are detailed by sequentially listing the general procedure (letter codes) in parentheses after their name. A worked example of this protocol is given below using Example #G.1.2 as a non-limiting illustration. Example #G.1.2 (6-[6-(4-fluorophenyl)-imidazo[2,1-b]thiazol-5-yl]-1-(3-methylbutyl)-1H-benzoimidazol-2-ylamine) was prepared from 4-[6-(4-fluorophenyl)-imidazo[2,1-b]thiazol-5-yl]-N'2'-(3-methylbutyl)-benzene-1,2-diamine using general procedure G as represented in the following synthetic scheme:

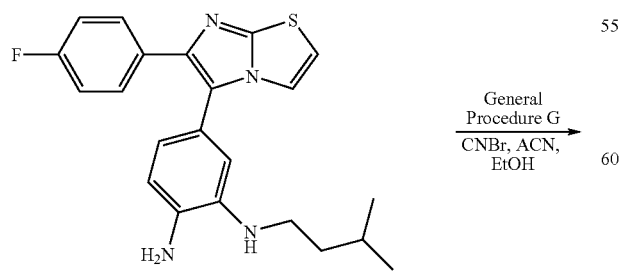

Precursor to Example #G.1.2

General Procedure G
CNBr, ACN, EtOH

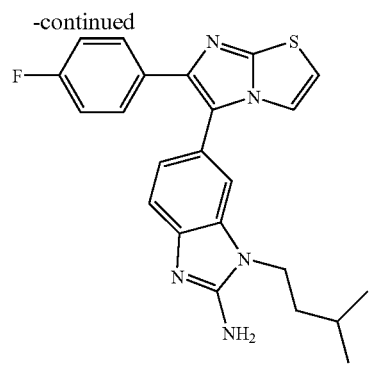

Example #G.1.2

The precursor to Example #G.1.2 (4-[6-(4-fluorophenyl)-imidazo[2,1-b]thiazol-5-yl]-N'2'-(3-methylbutyl)-benzene-1,2-diamine) was prepared by the noted reaction sequence: using A from 6-(4-fluorophenyl)-imidazo[2,1-b]thiazole [WO2004110990A2, Example 2, Step 1] and NIS, C from Preparation #B.1, D from isoamylamine, E, which translates to the following synthetic scheme:

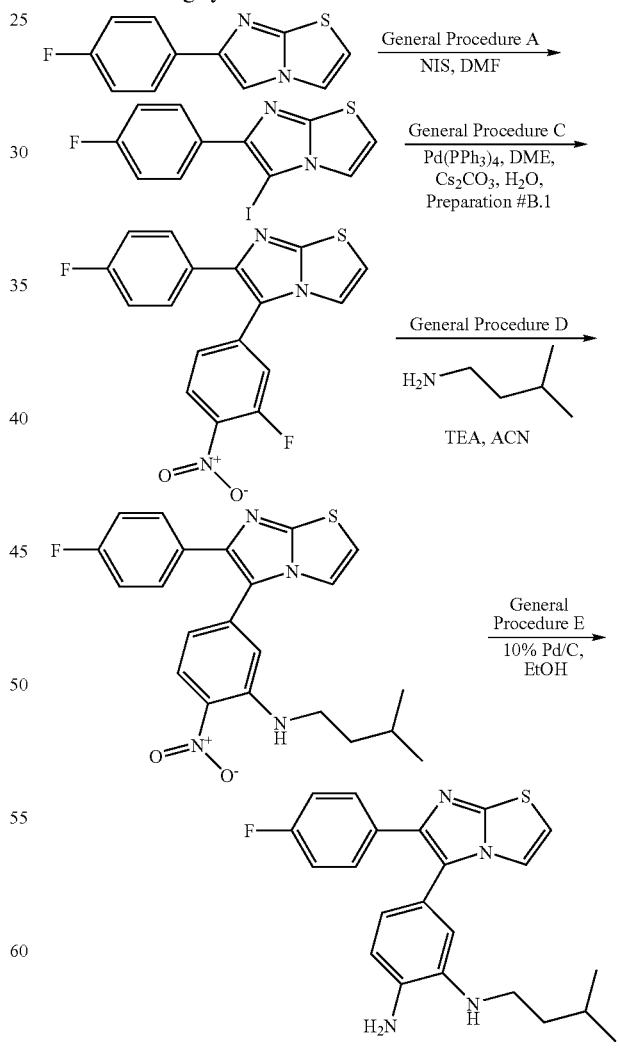

Precursor to Example #G.1.2

The general synthetic methods used in each general procedure follow and include an illustration of a compound that was synthesized using the designated general procedure. None of the specific conditions and reagents noted in the following are to be construed as limiting the scope of the invention and are provided for illustrative purposes only. All starting materials are commercially available from Sigma-Aldrich unless otherwise noted after the chemical name. Analytical data is included either in the illustrations of the general procedures or in the tables of examples. Unless otherwise stated, all $^1$H NMR data were collected on a Varian Mercury Plus 400 MHz instrument; chemical shifts are quoted in parts per million (ppm). High-pressure liquid chromatography (HPLC) analytical data referenced to the table of HPLC conditions using the lower case method letter in parentheses provided in Table 1.

about 16 h. The mixture was cooled in ice water, filtered, and washed with EtOH. Drying under vacuum at about 60° C. provided the title compound (5.84 g, 77%): LC/MS (Table 1, Method a) $R_t$, =2.68 min; MS m/z: 237.3 (M+H)$^+$.

Step B: 6-(2,4-Difluorophenyl)-5-iodoimidazo[2,1-b]thiazole

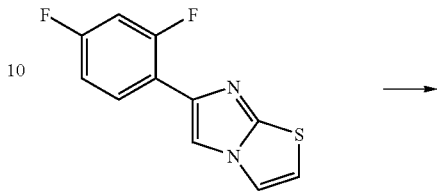

TABLE 1

LC/MS and HPLC methods

| Method | Conditions |
|---|---|
| a | LC/MS: 5% to 95% ACN/0.01M aqueous ammonium acetate over 3.7 min with a hold at 95% ACN/0.01M aqueous ammonium acetate for 1 min at 1.3 mL/min; Zorbax XDB C18, 5 µm, 50 × 4.6 mm column. Detection methods are diode array (DAD) and evaporative light scattering (ELSD) detection as well as pos/neg electrospray ionization. |
| b | LC/MS: 5% to 95% ACN/0.01M aqueous ammonium acetate over 2.0 min; 95% ACN/0.01M aqueous ammonium acetate for 1.5 min at 1.4 mL/min; UV λ = 210-360 nm; Genesis C8, 4 µm, 30 × 4.6 mm column; ESI +ve/−ve. |
| c | HPLC: The column used for the chromatography was a 21.2 × 250 mm Hypersil C18 HS column (8 µm particles). The gradient was 15-100% B over 25 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| d | The column used for the chromatography is a 4.6 × 30 mm Vydac Genesis C8 column (4 µm particles). The gradient was 5-60% B in 1.5 min then 60-95% B to 2.5 min with a hold at 95% B for 1.2 min (1.3 mL/min flow rate). Mobile phase A was 10 mM ammonium acetate, mobile phase B was HPLC grade acetonitrile. Detection methods are diode array (DAD) and evaporative light scattering (ELSD) detection as well as pos/neg electrospray ionization. |
| e | HPLC: The column used for the chromatography was a 21.2 × 250 mm Hypersil C18 HS column (8 µm particles). The gradient was 5-100% B over 25 min (21 mL/min flow rate) and then 100% B for 6 min (21 mL/min flow rate). Mobile phase A was 0.05 N aqueous ammonium acetate buffer (pH 4.5) and mobile phase B was HPLC grade acetonitrile. Detection method is UV, λ = 254 nm. |
| f | HPLC: The column used for the chromatography was a 21.2 × 250 mm Hypersil C18 HS column (8 µm particles). The gradient was 20-60% B over 40 min (21 mL/min flow rate). Mobile phase A was 0.05 N aqueous ammonium acetate buffer (pH 4.5) and mobile phase B was HPLC grade acetonitrile. Detection method is UV, λ = 254 nm. |

Preparation #1: 6-(2,4-Difluorophenyl)-5-iodoimidazo[2,1-b]thiazole

Step A:
6-(2,4-Difluorophenyl)imidazo[2,1-b]thiazole

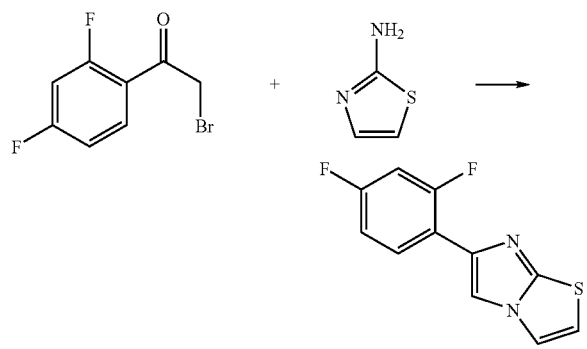

2-Bromo-2′,4′-difluoroacetophenone (7.50 g, 31.9 mmol) and thiazol-2-amine (3.20 g, 31.9 mmol) were added to EtOH (85 mL) and then heated to about 85° C. in an oil bath for -continued NIS (5.56 g, 24.7 mmol) was added to 6-(2,4-difluorophenyl)imidazo[2,1-b]thiazole (5.84 g, 24.7 mmol) in DMF (60 mL) then stirred at ambient temperature for about 30 min. The mixture was diluted with water (about 500 mL), filtered, and washed with Et$_2$O to give the title compound (5.17 g, 57.8%): LC/MS (Table 1, Method a) $R_t$=2.13 min; MS m/z: 363.0 (M+H)$^+$.

Preparation #2: 5-Methyloxazol-2-amine

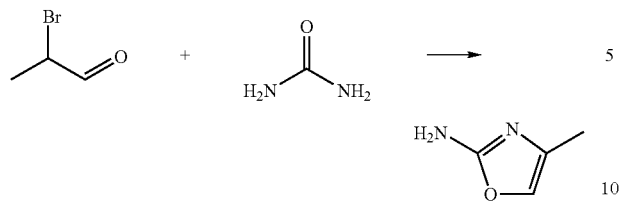

2-Bromopropanal (62.8 g, 458 mmol) and urea (30.3 g, 504 mmol) were heated at about 100° C. for about 16 h, then cooled and extracted with DCM (3×50 mL). The aqueous solution was basified with 50% aqueous NaOH then extracted with DCM (3×50 mL). The combined extracts from the basic solution were dried over MgSO$_4$, filtered and evaporated to give the title compound (2.17 g, 4.82%) as an oil, which crystallized on standing. Further extraction gave a second crop of title compound. Total yield was 4.64 g (10.3%): $^1$H NMR (CDCl$_3$) δ 2.2 (3H, s), 4.7 (2H, bs), 6.30 (1H, s)

Preparation #3: 3-Methyloxetane-3-carbaldehyde

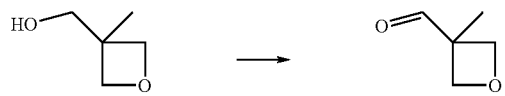

To a 100 mL round-bottomed flask charged with PCC (1.7 g, 5.9 mmol) was added DCM (25 mL) to give an orange solution. (3-Methyloxetan-3-yl)methanol (0.50 g, 4.90 mmol) was added dropwise as a solution in DCM (5 mL). About 0.5 g of Celite® was added, and the reaction was allowed to stir for about 4 h at ambient temperature. The reaction was then filtered through about 20 g of SiO$_2$ and concentrated under reduced pressure to provide the title compound as a colorless oil (0.23 g, 47%). $^1$H NMR (CDCl$_3$ δ 9.95 (s, 1H), 8.86 (s, 1H), 4.87 (d, J=3.2 Hz, 2H), 4.50 (d, J=3.2 Hz, 2H).

Preparation #4: 6-(2,4-Difluorophenyl)-5-(6-fluoropyridin-3-yl)imidazo[2,1-b]oxazole-2-carboxylic acid

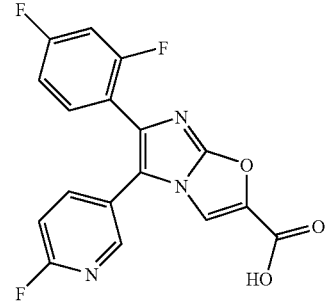

A 100 mL round-bottomed flask was charged with ethyl 6-(2,4-difluorophenyl)-5-iodoimidazo[2,1-b]oxazole-2-carboxylate (1.08 g, 2.58 mmol; prepared using O from 2-aminooxazole-5-carboxylic acid ethyl ester [Combi-blocks] with 2-bromo-2',4'-difluoroacetophenone, A with NIS), 6-fluoropyridin-3-ylboronic acid (0.437 g, 3.10 mmol; Asymchem), and Cs$_2$CO$_3$ (2.10 g, 6.46 mmol) in 1,4-dioxane (25 mL) and water (5 μL) to give a tan solution. Nitrogen was bubbled through the solution for about 5 min. PdCl$_2$(PPh$_3$)$_2$ (0.181 g, 0.258 mmol) was added followed by heating to about 100° C. After about 1 h, the reaction was cooled to ambient temperature and concentrated. The solid was suspended in DCM (10 mL) dried over MgSO$_4$, filtered through Celite®, washing the Celite® pad with DCM (10 mL), and concentrated in vacuo. The resulting solid was dissolved in 1,4-dioxane (5 mL) and LiOH (0.309 g, 12.9 mmol) was added in water (20 mL). The reaction was allowed to stir at ambient temperature for about 1 h at which time the reaction was concentrated and acidified with 1N HCl. The resulting solid was filtered off and washed with about 5 mL of water and dried in a vacuum oven to give title compound (0.835 g, 90%): LC/MS (Table 1, Method a) R$_t$=1.73 min; MS m/z: 360.1 (M+H)$^+$.

Preparation #5: (1R,2R)-2-(6-(6-(4-Fluorophenyl)imidazo[2,1-b]oxazol-5-yl)-[1,2,4]triazolo[4,3-a]pyridin-3-yl)cyclopropanecarboxylic acid

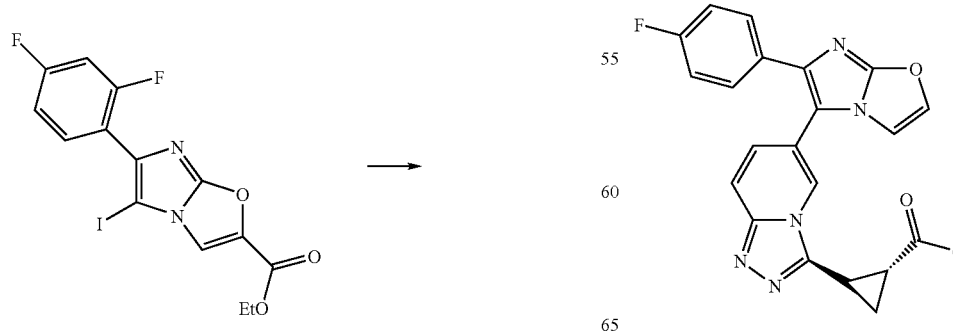

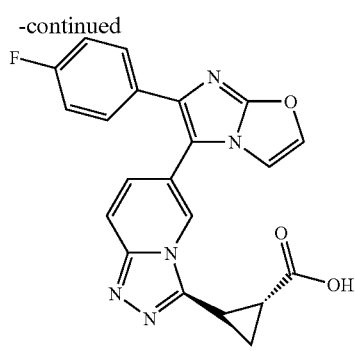

A solution of (1R,2R)-ethyl 2-(6-(6-(4-fluorophenyl)imidazo[2,1-b]oxazol-5-yl)-[1,2,4]triazolo[4,3-a]pyridin-3-yl)cyclopropanecarboxylate (0.15 g, 0.35 mmol; Example #K.1.1.17) in 1,4-dioxane (10 mL) was treated with 1N NaOH solution (6 mL, 6 mmol). The reaction mixture was stirred at about 60° C. for about 3 h. The organic solvent was removed under reduced pressure. The aqueous layer was acidified to about pH 6 using 1N HCl. The precipitate was filtered, dried in a heated vacuum oven at about 60° C., to give the title compound (0.140 g, 99%) LC/MS (Table 1, Method a) $R_t$, =1.72 min; MS m/z: 404.1 (M+H)$^+$.

General Procedure A: Halogenation of an imidazo[2,1-b]thiazole or an imidazo[2,1-b]oxazole A solution of a 6-(aryl)imidazo[2,1-b]thiazole or a 6-(aryl)imidazo[2,1-b]oxazole (preferably 1 equiv), a halogenating agent such as NBS or NIS (0.95-1.2 equiv, preferably 1.1 equiv) and a suitable solvent such as DMF is stirred at ambient temperature. After about 0.5-8 h, preferably 1-3 h, the reaction is poured into water and the resulting precipitate is filtered, washing with additional water, and dried in a vacuum oven at about 55-65° C. to give the target compound. Optionally, the material is further purified by crystallization or trituration from an appropriate solvent or solvents, or by chromatography to give the target compound.

Illustration of General Procedure A

Preparation #A.1:
6-(4-Fluorophenyl)-5-iodo-imidazo[2,1-b]oxazole)

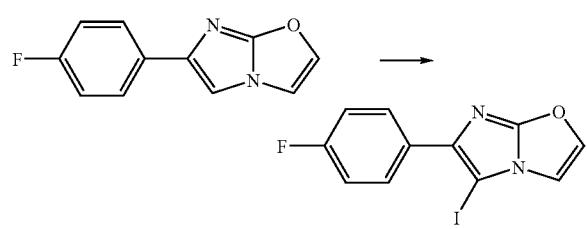

A solution of 6-(4-fluorophenyl)imidazo[2,1-b]oxazole (4.92 g, 24.3 mmol; prepared according to WO2004110990A2, Example 1, Steps 1-3), NIS (5.75 g, 25.6 mmol), and DMF (100 mL) was stirred at ambient temperature. After about 3 h, the reaction was poured into water (300 mL) and the resulting precipitate was filtered, washing with additional water, and dried in a vacuum oven at about 55-65° C. to give the title compound (7.21 g, 89%): LC/MS (Table 1, Method b) $R_t$, =2.09 min; MS m/z: 329.1 (M+H)$^+$.

General Procedure B: Formation of a Boronate from an Aryl or Heteroaryl Halide

A mixture of an aryl or heteroaryl halide (preferably 1 equiv), a suitable base (such as KOAc or TEA) (1-10 equiv, preferably 1.5-6 equiv), bis(pinacolato)diboron or pinacolborane (1-5 equiv, preferably 1-1.5 equiv), and a suitable solvent (such as 1,4-dioxane or DMF) is degassed under N$_2$/vacuum purge. Then a catalyst (for example, [1,1'-bis(diphenylphosphino)-ferrocene]dichloropalladium(II) complex with DCM (1:1)) (0.02-0.20 equiv, preferably 0.04-0.10 equiv) is added. The reaction is heated at about 80-120° C. (preferably 100° C.) for about 1-24 h (preferably 2-18 h) then is cooled to ambient temperature. The mixture is optionally concentrated under reduced pressure, diluted with or partitioned between water and an organic solvent (for example, EtOAc or DCM), and filtered to remove insoluble material, washing with additional solvent. The layers are separated and the aqueous layer is optionally extracted with additional organic solvent. The combined organic layers may be optionally washed with brine, dried over Na$_2$SO$_4$ or MgSO$_4$, then decanted or filtered prior to concentrating under reduced pressure. The crude product is purified by crystallization or trituration from an appropriate solvent or solvents, or by chromatography to give the target compound.

Illustration of General Procedure B

Preparation #B.1: 2-(3-Fluoro-4-nitrophenyl)-4,4,5,5-tetramethyl-[1,3,2]dioxaborolane

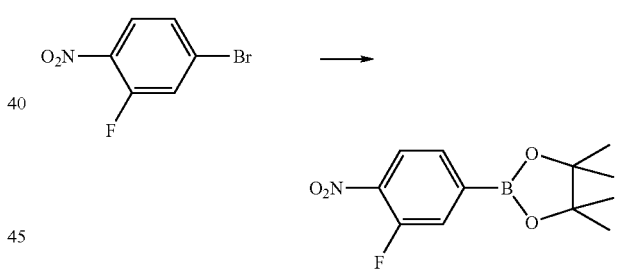

A mixture of 4-bromo-2-fluoronitrobenzene (20.0 g, 90.9 mmol; 3B Medical Systems), KOAc (26.8 g, 0.273 mol; J. T. Baker), bis(pinacolato)diboron (23.1 g, 90.9 mmol), and 1,4-dioxane (200 mL) was degassed under N$_2$/vacuum purge. Then [1,1'-bis(diphenylphosphino)-ferrocene]dichloropalladium(II) complex with DCM (1:1) (3.0 g, 3.6 mmol) was added and the reaction was heated at about 100° C. for about 18 h. The reaction was then cooled to ambient temperature and concentrated under reduced pressure. The mixture was partitioned between water (100 mL) and DCM (100 mL) then filtered to remove any solid, washing with additional DCM (200 mL). The layers were separated and the organic layer was washed with brine, dried over Na$_2$SO$_4$, filtered, and concentrated. The crude material was purified by silica gel chromatography using heptane/DCM (stepwise gradient, 9:1 to 4:1 to 2:1) to give the title compound (19.4 g, 70%): $^1$H NMR (DMSO-d$_6$, 400 MHz) δ 8.15 (m, 1H), 7.67 (m, 2H), 1.33 (s, 12H).

General Procedure C: Suzuki Coupling of a Boronate or Boronic Acid with an Aryl or Heteroaryl Halide A mixture of an aryl or heteroaryl halide (preferably 1 equiv), a boronic acid or a boronate (1-3 equiv, preferably 1.2-1.8 equiv), a suitable base (such as $Cs_2CO_3$, 2M $Na_2CO_3$, or $K_3PO_4$, preferably $Cs_2CO_3$) (1-5 equiv, preferably 2-4 equiv), a catalyst (such as tetrakis(triphenylphosphine)palladium(0) or bis[triphenylphosphine)palladium(II) chloride, preferably tetrakis(triphenylphosphine)palladium(0)) (0.02-0.20 equiv, preferably 0.10 equiv), a suitable solvent or solvent combination (such as toluene/water, dioxane/water, or DME/water, preferably dioxane/water or DME/water) is heated at about 80-120° C. (preferably 100° C.) for about 0.5-24 h (preferably 12-16 h). After cooling to ambient temperature, the mixture is optionally concentrated under reduced pressure and is diluted with or partitioned between water and an organic solvent (for example, EtOAc or DCM). then filtered to remove insoluble material, washing with additional solvent. The layers are separated and the aqueous layer is optionally extracted with additional organic solvent. The combined organic layers may be optionally washed with brine, dried over $Na_2SO_4$ or $MgSO_4$, then decanted or filtered, prior to concentrating under reduced pressure. The crude product is purified by crystallization or trituration from an appropriate solvent or solvents, or by chromatography to give the target compound.

Illustration of General Procedure C

Preparation #C.1: 5-(3-Fluoro-4-nitrophenyl)-6-(4-fluorophenyl)-imidazo[2,1-b]oxazole

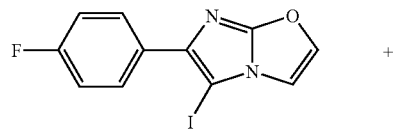

+

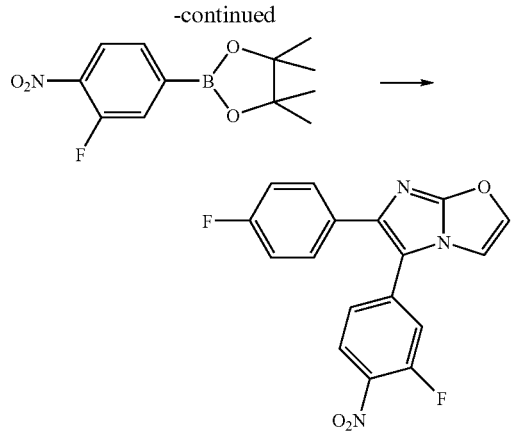

A mixture of 6-(4-fluorophenyl)-5-iodo-imidazo[2,1-b]oxazole (10.0 g, 27.4 mmol; Preparation #A.1), 2-(3-fluoro-4-nitrophenyl)-4,4,5,5-tetramethyl-[1,3,2]dioxaborolane (11.9 g, 41.1 mmol; Preparation #B.1), $Cs_2CO_3$ (28.6 g, 87.8 mmol), tetrakis(triphenylphosphine)palladium(0) (3.17 g, 2.74 mmol; Strem), DME (150 mL) and water (30.0 mL) was added to a flask with screw-thread top. The flask was sealed and heated at about 100° C. for about 16 h. After cooling to ambient temperature the reaction was concentrated under reduced pressure to remove organic solvent. The resulting mixture was diluted with water (200 mL) and EtOAc (200 mL) then filtered to remove insoluble material. The layers were separated and the aqueous layer was extracted with additional EtOAc (2×200 mL). The combined organic layers were washed with brine, dried over $Na_2SO_4$, decanted, and concentrated. The crude material was purified by silica gel chromatography using DCM to give the title compound (7.80 g, 78%): LC/MS (Table 1, Method b) $R_t$=2.19 min; MS m/z: 342.1 $(M+H)^+$.

TABLE C.1

Examples prepared from 6-(4-fluorophenyl)-5-iodo-imidazo[2,1-b]thiazole (prepared using General Procedure A from 6-(4-fluorophenyl)-imidazo[2,1-b]thiazole [WO2004110990A2, Example 2, Step 1] and NIS) using General Procedure C

| Boronate or Boronic Acid | Product | Example # | $R_t$ min (method) | m/z ESI+ $(M + H)^+$ |
|---|---|---|---|---|
| 5-(4,4,5,5-Tetramethyl-1,3,2-dioxaborolan-2-yl)-1H-indazole [NetChem] | 5-[6-(4-Fluorophenyl)imidazo[2,1-b]thiazol-5-yl]-1H-indazole | C.1.1 | 1.81 (b) | 335.4 |
| 2-(2,2,2-Trifluoroacetylamino)imidazo[1,2-a]pyridine-6-boronic acid [Tetrahedron Lett 2002, 43, 9051-9054] | 6-[6-(4-Fluorophenyl)imidazo[2,1-b]thiazol-5-yl]-imidazo[1,2-a]pyridin-2-ylamine | C.1.2 | 1.56 (b) | 350.5 |
| 4-Fluoro-1-isobutyl-6-(4,4,5,5-tetramethyl-1,3,2-dioxaborolan-2-yl)-1H-benzimidazol-2-ylamine [prepared using D from 5-bromo-1,3-difluoro-2-nitrobenzene (prepared according to US20040235886A1, Example 1) and isobutylamine, F using tin(II) chloride dihydrate, G, B using bis(pinacolato)diboron] | 4-Fluoro-6-[6-(4-fluorophenyl)-imidazo[2,1-b]thiazol-5-yl]-1-isobutyl-1H-benzoimidazol-2-ylamine | C.1.3 | 2.06 (b) | 424.3 |

TABLE C.1-continued

Examples prepared from 6-(4-fluorophenyl)-5-iodo-imidazo[2,1-b]thiazole (prepared using General Procedure A from 6-(4-fluorophenyl)-imidazo[2,1-b]thiazole [WO2004110990A2, Example 2, Step 1] and NIS) using General Procedure C

| Boronate or Boronic Acid | Product | Example # | R, min (method) | m/z ESI+ (M + H)+ |
|---|---|---|---|---|
| 2-Amino-3-(propane-2-sulfonyl)-3H-benzoimidazole-5-boronic acid [prepared according to WO2004014900, Preparation 56] | 6-[6-(4-Fluorophenyl)-imidazo[2,1-b]thiazol-5-yl]-1H-benzoimidazol-2-ylamine | C.1.4 | 1.15 (b) | 350.3 |
| 2-Amino-3-(propane-2-sulfonyl)-3H-benzoimidazole-5-boronic acid [prepared according to WO2004014900, Preparation 56] | 6-[6-(4-Fluorophenyl)-imidazo[2,1-b]thiazol-5-yl]-1-(propane-2-sulfonyl)-1H-benzoimidazol-2-ylamine | C.1.5 | 1.95 (b) | 456.4 |

TABLE C.2

Examples prepared from 6-(4-fluorophenyl)-5-iodo-imidazo[2,1-b]oxazole (Preparation #A.1) using General Procedure C

| Boronate or Boronic Acid | Product | Example # | R, min (method) | m/z ESI+ (M + H)+ |
|---|---|---|---|---|
| 3-Isopropyl-6-(4,4,5,5-tetramethyl-1,3,2-dioxaborolan-2-yl)-1,2,4-triazolo[4,3-a]pyridine [prepared using B from 6-bromo-3-isopropyl-[1,2,4]triazolo[4,3-a]pyridine (CgeneTech) and bis(pinacolato)diboron] | 6-[6-(4-Fluorophenyl)-imidazo[2,1-b]oxazol-5-yl]-3-isopropyl-1,2,4-triazolo[4,3-a]pyridine | C.2.1 | 1.91 (b) | 362.2 |
| 3-Isobutyl-6-(4,4,5,5-tetramethyl-1,3,2-dioxaborolan-2-yl)-1,2,4-triazolo[4,3-a]pyridine [prepared using B from Preparation #I.1 and bis(pinacolato)diboron] | 6-[6-(4-Fluorophenyl)-imidazo[2,1-b]oxazol-5-yl]-3-isobutyl-1,2,4-triazolo[4,3-a]pyridine | C.2.2 | 2.01 (b) | 376.1 |
| 3-Methyl-5-(4,4,5,5-tetramethyl-[1,3,2]dioxaborolan-2-yl)-1H-indazole [prepared using B from 5-bromo-3-methyl-1H-indazole (J&W PharmLab) and bis(pinacolato)diboron] | 5-[6-(4-Fluorophenyl)-imidazo[2,1-b]oxazol-5-yl]-3-methyl-1H-indazole | C.2.3 | 1.90 (b) | 333.1 |
| 4-Fluoro-1-isobutyl-6-(4,4,5,5-tetramethyl-1,3,2-dioxaborolan-2-yl)-1H-benzimidazol-2-ylamine [prepared using D from 5-bromo-1,3-difluoro-2-nitrobenzene (prepared according to US20040235886A1, Example 1) and isobutylamine, F using tin(II) chloride dihydrate, G, B using bis(pinacolato)diboron] | 4-Fluoro-6-[6-(4-fluorophenyl)-imidazo[2,1-b]oxazol-5-yl]-1-isobutyl-1H-benzoimidazol-2-ylamine | C.2.4 | 1.98 (b) | 408.3 |
| 4-Fluoro-1-isobutyl-6-(4,4,5,5-tetramethyl-[1,3,2]dioxaborolan-2-yl)-1H-benzotriazole [prepared using D from 5-bromo-1,3-difluoro-2-nitrobenzene (prepared according to US20040235886A1, | 4-Fluoro-6-[6-(4-fluorophenyl)-imidazo[2,1-b]oxazol-5-yl]-1-isobutyl-1H-benzotriazole | C.2.5 | 2.30 (b) | 394.3 |

TABLE C.2-continued

Examples prepared from 6-(4-fluorophenyl)-5-iodo-imidazo[2,1-b]oxazole (Preparation #A.1) using General Procedure C

| Boronate or Boronic Acid | Product | Example # | $R_t$ min (method) | m/z ESI+ $(M + H)^+$ |
|---|---|---|---|---|
| Example 1) and isobutylamine, F using tin(II) chloride dihydrate, H, B using bis(pinacolato)diboron] | | | | |

General Procedure D: Displacement of an Aryl or Heteroaryl Halide with an Amine or Hydrazine To a suspension of an aryl or heteroaryl halide (preferably 1 equiv) in a suitable organic solvent (such as ACN, THF, n-PrOH, or IPA, preferably ACN or n-PrOH) is added an amine or hydrazine (1-20 equiv, preferably 3-5 equiv) and optionally a base (such as TEA, DIEA) (1-5 equiv, preferably 2-3 equiv). The reaction was heated at about 50-100° C. (preferably 80° C.) for about 0.5-24 h (preferably 2-6 h). If the product precipitates during the reaction or upon cooling it is directly filtered and dried or, if necessary, is purified further as indicated below. Alternatively, the mixture is optionally concentrated under reduced pressure and is diluted with or partitioned between water and an organic solvent (for example, EtOAc or DCM) then filtered to remove insoluble material, washing with additional solvent. The layers are separated and the aqueous layer is extracted with additional organic solvent. The combined organic layers may be optionally washed with brine, dried over $Na_2SO_4$ or $MgSO_4$, then decanted or filtered, prior to concentrating under reduced pressure. The crude product is purified by crystallization or trituration from an appropriate solvent or solvents, or by chromatography to give the target compound.

Illustration of General Procedure D

Preparation #D.1: (2,2-Dimethylpropyl)-5-[6-(4-fluorophenyl)-imidazo[2,1-b]oxazol-5-yl]-2-nitrophenylamine

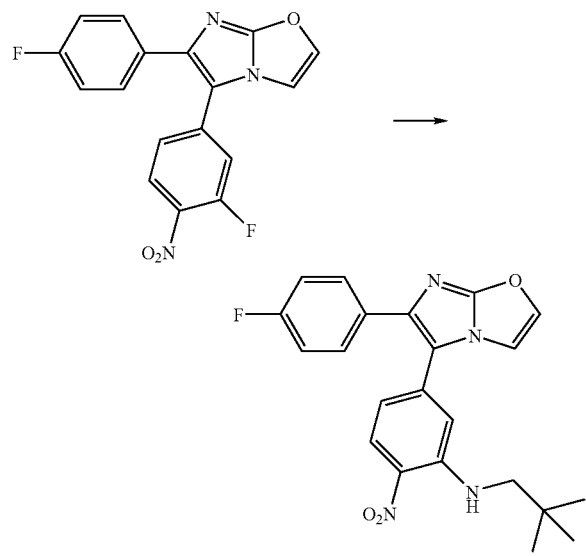

To a suspension of 5-(3-fluoro-4-nitrophenyl)-6-(4-fluorophenyl)-imidazo[2,1-b]oxazole (0.80 g, 2.2 mmol; Preparation #C.1) in ACN (6.0 mL) was added TEA (0.63 mL, 4.5 mmol) and 2,2-dimethylpropylamine (0.24 g, 2.7 mmol; TCI). The reaction was heated at about 80° C. for about 4 h then cooled to about 4° C. The resulting solid was filtered, washing with cold ACN (ca. 4° C.), and dried in a vacuum oven at about 55-65° C. to give the title compound (0.89 g, 96%): LC/MS (Table 1, Method b) $R_t$=2.62 min; MS m/z: 409.2 (M+H)$^+$.

General Procedure E: Reduction of a Nitro Group to an Aniline Via Hydrogenation To a mixture of a substituted aryl or heteroaryl nitro group (preferably 1 equiv) and an organic solvent (such as MeOH or EtOH, preferably EtOH) that had undergone a $N_2$/vacuum purge is added 10% palladium on carbon. Then an atmosphere of $H_2$ is introduced. After about 1-24 h (preferably 2-3 h) at about 20-60° C. (preferably ambient temperature), the $H_2$ atmosphere was removed via vacuum/$N_2$ purge. The reaction mixture may then be used as is in a second reaction such as general procedure G or H. Alternatively, the reaction is filtered through Celite®, washing with solvent (for example, MeOH), and concentrated under reduced pressure. The crude product is purified by crystallization or trituration from an appropriate solvent or solvents, or by chromatography to give the target compound.

Illustration of General Procedure E

Preparation #E.1: 4-[6-(4-Fluorophenyl)-imidazo[2,1-b]thiazol-5-yl]-N'2'-(3-methylbutyl)-benzene-1,2-diamine

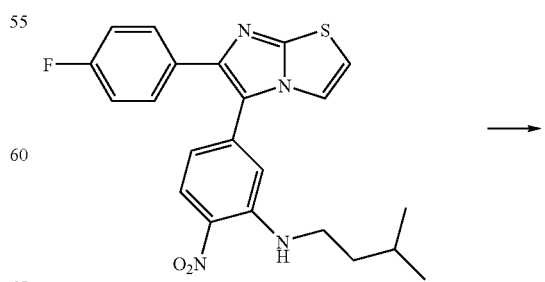

-continued

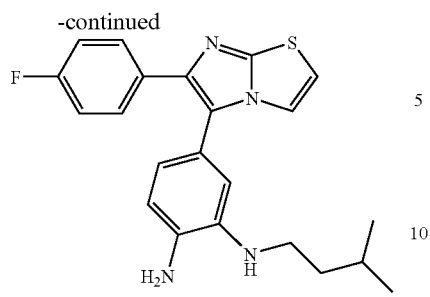

To a mixture of 5-[6-(4-fluorophenyl)-imidazo[2,1-b]thiazol-5-yl]-2-nitrophenyl-(3-methylbutyl)amine (0.075 g, 0.17 mmol; prepared using A from 6-(4-fluorophenyl)-imidazo[2,1-b]thiazole [WO2004110990A2, Example 2, Step 1] and NIS, C from Preparation #B.1, and D from isoamylamine) and EtOH (4.0 mL) that had undergone a $N_2$ vacuum purge was added 10% palladium on carbon (0.050 g; Strem). Then a $H_2$ atmosphere was introduced via balloon. After about 2.5 h, the $H_2$ atmosphere was removed via vacuum/$N_2$ purge and the reaction was filtered through Celite®, washing with MeOH, and concentrated under reduced pressure. The crude material was purified by silica gel chromatography using DCM/MeOH/$NH_4$OH (980:18:2) to give the title compound (0.043 g, 61%): LC/MS (Table 1, Method b) $R_t$=2.28 min; MS m/z: 395 (M+H)$^+$.

General Procedure F: Reduction of a Nitro Group to an Aniline Using Tin(II) Chloride A mixture of a substituted aryl or heteroaryl nitro group (preferably 1 equiv), an organic solvent (such as MeOH or EtOH, preferably EtOH), tin(II) chloride or tin(II) chloride dihydrate (2-10 equiv, preferably 5 equiv) is heated at about 40-80° C. (preferably 70° C.) for about 2-36 h (preferably 14-24 h). The reaction is cooled to ambient temperature then poured over ice. The pH is adjusted to ~8 with a base (such as 2M $Na_2CO_3$ or saturated aqueous $NaHCO_3$) and the mixture is filtered to remove tin salts. The filter cake is stirred with an organic solvent (such as EtOAc) then is filtered 1-4 times (preferably 3 times). Each organic filtrate is then used to extract the initial aqueous filtrate. The combined organic layers may be optionally washed with brine, dried over $Na_2SO_4$ or $MgSO_4$, then decanted or filtered, prior to concentrating under reduced pressure. The crude product is purified by crystallization or trituration from an appropriate solvent or solvents, or by chromatography to give the target compound.

Illustration of General Procedure F

Preparation #F.1: N'2'-(2,2-Dimethylpropyl)-4-[6-(4-fluorophenyl)-imidazo[2,1-b]oxazol-5-yl]-benzene-1,2-diamine

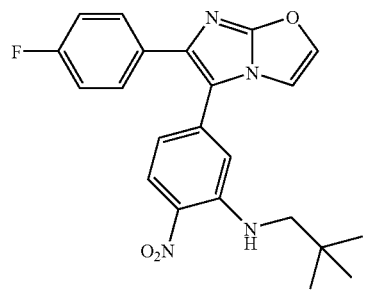

-continued

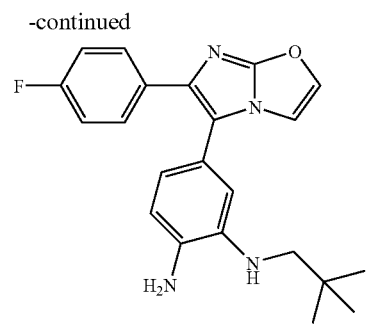

A mixture of (2,2-dimethylpropyl)-5-[6-(4-fluorophenyl)-imidazo[2,1-b]oxazol-5-yl]-2-nitrophenylamine (0.85 g, 0.0020 mol; Preparation #D.1), tin(II) chloride dihydrate (2.3 g, 10 mmol) and EtOH (20 mL) was heated at about 70° C. for about 24 h. The reaction was cooled to ambient temperature then poured over ice. The pH was adjusted to ~8 with saturated aqueous $NaHCO_3$ and the mixture was filtered to remove tin salts. The filter cake was stirred with EtOAc (3×100 mL) then filtered. Each organic filtrate was then used to extract the initial aqueous filtrate. The combined organic layers were washed with brine, dried over $Na_2SO_4$, decanted, and concentrated to give the title compound (0.85 g, 83%): LC/MS (Table 1, Method b) $R_t$, =2.30 min; MS m/z: 379.2 (M+H)$^+$.

General Procedure G: Cyclization of a Diamine with Cyanogen Bromide

To a solution of a diamine (preferably 1 equiv) in an organic solvent (for example, MeOH— or EtOH) is added cyanogen bromide or 5 M cyanogen bromide in ACN (1-10 equiv, preferably 3-5 equiv) at ambient temperature. After about 1-14 h (preferably 1-3 h), the reaction is concentrated under reduced pressure. The crude product is purified by crystallization or trituration from an appropriate solvent or solvents, or by chromatography to give the target compound.

Illustration of General Procedure G

Example #G.1.1

1-(2,2-Dimethylpropyl)-6-[6-(4-fluorophenyl)-imidazo[2,1-b]oxazol-5-yl]-1H-benzoimidazol-2-ylamine

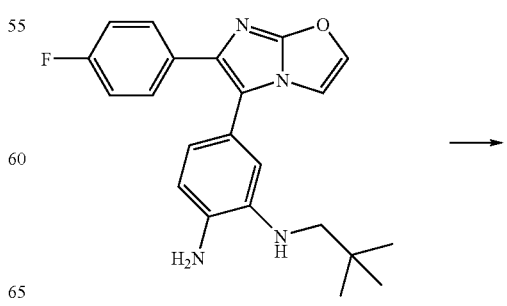

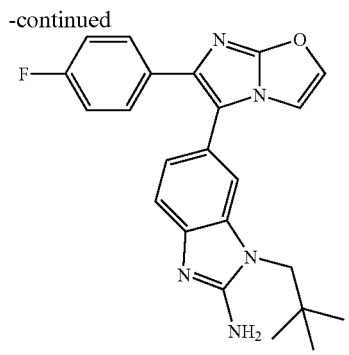

To a solution of N'2'-(2,2-dimethylpropyl)-4-[6-(4-fluorophenyl)-imidazo[2,1-b]oxazol-5-yl]-benzene-1,2-diamine (0.42 g, 0.83 mmol; Preparation #F.1) in MeOH (10 mL) was added 5M cyanogen bromide in ACN (0.82 mL; 4.1 mmol) dropwise at ambient temperature. After about 2 h, the reaction was concentrated under reduced pressure. The crude material was purified by silica gel chromatography using DCM/MeOH/NH$_4$OH (stepwise gradient, 990:9:1 to 980:18:2 to 970:27:3) to give the title compound (0.32 g, 93%): LC/MS (Table 1, Method b) R$_t$ =1.75 min; MS m/z: 404.2 (M+H)$^+$.

TABLE G.1

Examples prepared from diamines using General Procedure G

| Diamine | Product | Example # | R$_t$ min (method) | m/z ESI+ (M + H)$^+$ |
|---|---|---|---|---|
| 4-[6-(4-Fluorophenyl)-imidazo[2,1-b]thiazol-5-yl]-N'2'-(3-methylbutyl)-benzene-1,2-diamine [prepared using A from 6-(4-fluorophenyl)-imidazo[2,1-b]thiazole [WO2004110990A2, Example 2, Step 1] and NIS, C from Preparation #B.1, D from isoamylamine, E] | 6-[6-(4-Fluorophenyl)-imidazo[2,1-b]thiazol-5-yl]-1-(3-methylbutyl)-1H-benzoimidazol-2-ylamine | G.1.2 | 1.85 (b) | 420.7 |
| 4-[6-(4-Fluorophenyl)-imidazo[2,1-b]thiazol-5-yl]-N'2'-methyl-benzene-1,2-diamine [prepared using A from 6-(4-fluorophenyl)-imidazo[2,1-b]thiazole [WO2004110990A2, Example 2, Step 1] and NIS, C from Preparation #B.1, D from 2 M methylamine in THF, E] | 6-[6-(4-Fluorophenyl)-imidazo[2,1-b]thiazol-5-yl]-1-methyl-1H-benzoimidazol-2-ylamine | G.1.3 | 1.51 (b) | 364.5 |
| 4-[6-(4-Fluorophenyl)-imidazo[2,1-b]thiazol-5-yl]-N'2'-isopropyl-benzene-1,2-diamine [prepared using A from 6-(4-fluorophenyl)-imidazo[2,1-b]thiazole [WO2004110990A2, Example 2, Step 1] and NIS, C from Preparation #B.1, D from isopropylamine, E] | 6-[6-(4-Fluorophenyl)-imidazo[2,1-b]thiazol-5-yl]-1-isopropyl-1H-benzoimidazol-2-ylamine | G.1.4 | 1.59 (b) | 392.5 |
| 4-[6-(4-Fluorophenyl)-imidazo[2,1-b]thiazol-5-yl]-N'2'-isobutyl-benzene-1,2-diamine [prepared using A from 6-(4-fluorophenyl)-imidazo[2,1-b]thiazole [WO2004110990A2, Example 2, Step 1] and NIS, C from Preparation #B.1, D from isobutylamine, E] | 6-[6-(4-Fluorophenyl)-imidazo[2,1-b]thiazol-5-yl]-1-isobutyl-1H-benzoimidazol-2-ylamine | G.1.5 | 1.65 (b) | 406.6 |
| N'2'-Cyclohexyl-4-[6-(4-fluorophenyl)-imidazo[2,1-b]thiazol-5-yl]-benzene-1,2-diamine [prepared using A from 6-(4-fluorophenyl)-imidazo[2,1-b]thiazole [WO2004110990A2, Example 2, Step 1] and NIS, C from Preparation | 1-Cyclohexyl-6-[6-(4-fluorophenyl)-imidazo[2,1-b]thiazol-5-yl]-1H-benzoimidazol-2-ylamine | G.1.6 | 1.73 (b) | 432.6 |

TABLE G.1-continued

Examples prepared from diamines using General Procedure G

| Diamine | Product | Example # | R, min (method) | m/z ESI+ (M + H)+ |
|---|---|---|---|---|
| #B.1, D from cyclohexylamine, E] | | | | |
| N'2'-Benzyl-4-[6-(4-fluorophenyl)-imidazo[2,1-b]thiazol-5-yl]-benzene-1,2-diamine [prepared using A from 6-(4-fluorophenyl)-imidazo[2,1-b]thiazole [WO2004110990A2, Example 2, Step 1] and NIS, C from Preparation #B.1, D from benzylamine, E] | 1-Benzyl-6-[6-(4-fluorophenyl)-imidazo[2,1-b]thiazol-5-yl]-1H-benzoimidazol-2-ylamine | G.1.7 | 1.70 (b) | 440.6 |
| 4-[6-(4-Fluorophenyl)-imidazo[2,1-b]thiazol-5-yl]-N'2'(tetrahydropyran-4-ylmethyl)-benzene-1,2-diamine [prepared using A from 6-(4-fluorophenyl)-imidazo[2,1-b]thiazole [WO2004110990A2, Example 2, Step 1] and NIS, C from Preparation #B.1, D from 4-aminomethyl-tetrahydropyran, E] | 6-[6-(4-Fluorophenyl)-imidazo[2,1-b]thiazol-5-yl]-1-(tetrahydropyran-4-ylmethyl)-1H-benzoimidazol-2-ylamine | G.1.8 | 1.55 (b) | 448.2 |
| N'2'-Cyclohexylmethyl-4-[6-(4-fluorophenyl)-imidazo[2,1-b]thiazol-5-yl]-benzene-1,2-diamine [prepared using A from 6-(4-fluorophenyl)-imidazo[2,1-b]thiazole [WO2004110990A2, Example 2, Step 1] and NIS, C from Preparation #B.1, D from cyclohexylmethylamine, E] | 1-Cyclohexylmethyl-6-[6-(4-fluorophenyl)-imidazo[2,1-b]thiazol-5-yl]-1H-benzoimidazol-2-ylamine | G.1.9 | 1.93 (b) | 446.2 |
| N'2'-Cyclopropylmethyl-4-[6-(4-fluorophenyl)-imidazo[2,1-b]thiazol-5-yl]-benzene-1,2-diamine [prepared using A from 6-(4-fluorophenyl)-imidazo[2,1-b]thiazole [WO2004110990A2, Example 2, Step 1] and NIS, C from Preparation #B.1, D from cyclopropylmethylamine, E] | 1-Cyclopropylmethyl-6-[6-(4-fluorophenyl)-imidazo[2,1-b]thiazol-5-yl]-1H-benzoimidazol-2-ylamine | G.1.10 | 1.66 (b) | 404.1 |
| 4-[6-(4-Fluorophenyl)-imidazo[2,1-b]thiazol-5-yl]-N'2'-pyridin-2-ylmethyl-benzene-1,2-diamine [prepared using A from 6-(4-fluorophenyl)-imidazo[2,1-b]thiazole [WO2004110990A2, Example 2, Step 1] and NIS, C from Preparation #B.1, D from 1-pyridin-2-ylmethylamine, E] | 6-[6-(4-Fluorophenyl)-imidazo[2,1-b]thiazol-5-yl]-1-pyridin-2-ylmethyl-1H-benzoimidazol-2-ylamine | G.1.11 | 1.60 (b) | 441.1 |
| 4-[6-(4-Fluorophenyl)-imidazo[2,1-b]oxazol-5-yl]-N'2'-isobutyl-benzene-1,2-diamine [prepared using D from Preparation #C.1 and isobutylamine, F using tin(II) chloride dihydrate] | 6-[6-(4-Fluorophenyl)-imidazo[2,1-b]oxazol-5-yl]-1-isobutyl-1H-benzoimidazol-2-ylamine | G.1.12 | 1.86 (b) | 390.2 |

TABLE G.1-continued

Examples prepared from diamines using General Procedure G

| Diamine | Product | Example # | R, min (method) | m/z ESI+ (M + H)+ |
|---|---|---|---|---|
| N'2'-Benzyl-4-[6-(4-fluorophenyl)-imidazo[2,1-b]oxazol-5-yl]-benzene-1,2-diamine [prepared using D from Preparation #C.1 and benzylamine, F using tin(II) chloride dihydrate] | 1-Benzyl-6-[6-(4-fluorophenyl)-imidazo[2,1-b]oxazol-5-yl]-1H-benzoimidazol-2-ylamine | G.1.13 | 1.92 (b) | 390.6 |
| N'2'-Cyclopropyl-4-[6-(4-fluorophenyl)-imidazo[2,1-b]thiazol-5-yl]-benzene-1,2-diamine [prepared using A from 6-(4-fluorophenyl)-imidazo[2,1-b]thiazole [WO2004110990A2, Example 2, Step 1] and NIS, C from Preparation #B.1, D from cyclopropylamine, E] | 1-Cyclopropyl-6-[6-(4-fluorophenyl)-imidazo[2,1-b]thiazol-5-yl]-1H-benzoimidazol-2-ylamine | G.1.14 | 1.59 (b) | 390.6 |
| 3-({2-Amino-5-[6-(4-fluorophenyl)-imidazo[2,1-b]thiazol-5-yl]-phenylamino}-methyl)-pyrrolidine-1-carboxylic acid tert-butyl ester [prepared using A from 6-(4-fluorophenyl)-imidazo[2,1-b]thiazole [WO2004110990A2, Example 2, Step 1] and NIS, C from Preparation #B.1, D from (+/−)-3-(aminomethyl)-1-N-Boc-pyrrolidine (Astatech), E] | 3-{6-[6-(4-Fluorophenyl)-imidazo[2,1-b]thiazol-5-yl]-2-methyl-benzoimidazol-1-ylmethyl}-pyrrolidine-1-carboxylic acid tert-butyl ester | G.1.15 | 2.03 (b) | 532.7 |
| 2-({2-Amino-5-[6-(4-fluorophenyl)-imidazo[2,1-b]thiazol-5-yl]-phenylamino}-methyl)-pyrrolidine-1-carboxylic acid tert-butyl ester [prepared using A from 6-(4-fluorophenyl)-imidazo[2,1-b]thiazole [WO2004110990A2, Example 2, Step 1] and NIS, C from Preparation #B.1, D from (+/−)-2-(aminomethyl)-1-N-Boc-pyrrolidine (Astatech), E] | 2-{2-Amino-6-[6-(4-fluorophenyl)-imidazo[2,1-b]thiazol-5-yl]-benzoimidazol-1-ylmethyl}-pyrrolidine-1-carboxylic acid tert-butyl ester | G.1.16 | 1.78 (b) | 533.8 |
| 3-({2-Amino-5-[6-(4-fluorophenyl)-imidazo[2,1-b]thiazol-5-yl]-phenylamino}-methyl)-azetidine-1-carboxylic acid tert-butyl ester [prepared using A from 6-(4-fluorophenyl)-imidazo[2,1-b]thiazole [WO2004110990A2, Example 2, Step 1] and NIS, C from Preparation #B.1, D from 3-aminomethyl-1-N-Boc-azetidine (Astatech), E] | 3-{2-Amino-6-[6-(4-fluorophenyl)-imidazo[2,1-b]thiazol-5-yl]-benzoimidazol-1-ylmethyl}-azetidine-1-carboxylic acid tert-butyl ester | G.1.17 | 1.74 (b) | 519.8 |
| 4-[6-(4-Fluorophenyl)-imidazo[2,1-b]thiazol-5-yl]-N'2'-(1-methyl-1H-pyrrol-2-ylmethyl)-benzene-1,2-diamine [prepared using A from 6-(4-fluorophenyl)-imidazo[2,1-b]thiazole [WO2004110990A2, Example 2, Step 1] and NIS, C from Preparation #B.1, D from (1-methyl- | 6-[6-(4-Fluorophenyl)-imidazo[2,1-b]thiazol-5-yl]-1-(1-methyl-1H-pyrrol-2-ylmethyl)-1H-benzoimidazol-2-ylamine | G.1.18 | 1.92 (b) | 443.3 |

TABLE G.1-continued

Examples prepared from diamines using General Procedure G

| Diamine | Product | Example # | $R_t$ min (method) | m/z ESI+ $(M + H)^+$ |
|---|---|---|---|---|
| 1H-pyrrol-2-yl)methylamine, E] | | | | |
| N'2'-tert-Butyl-4-[6-(4-fluorophenyl)-imidazo[2,1-b]oxazol-5-yl]-benzene-1,2-diamine [prepared using D from Preparation #C.1 and tert-butylamine, F using tin(II) chloride dihydrate] | 1-tert-Butyl-6-[6-(4-fluorophenyl)-imidazo[2,1-b]oxazol-5-yl]-1H-benzoimidazol-2-ylamine | G.1.19 | 1.67 (b) | 390.2 |
| 4-[6-(4-Fluorophenyl)-imidazo[2,1-b]oxazol-5-yl]-N'2'-phenyl-benzene-1,2-diamine [prepared using D from Preparation #C.1 and aniline, F using tin(II) chloride dihydrate] | 6-[6-(4-Fluorophenyl)-imidazo[2,1-b]oxazol-5-yl]-1-phenyl-1H-benzoimidazol-2-ylamine | G.1.20 | 1.80 (b) | 410.2 |
| 2-{2-Amino-5-[6-(4-fluorophenyl)-imidazo[2,1-b]oxazol-5-yl]-phenylamino}-ethanol [prepared using D from Preparation #C.1 and ethanolamine, F using tin(II) chloride dihydrate] | 2-{2-Amino-6-[6-(4-fluorophenyl)-imidazo[2,1-b]oxazol-5-yl]-benzoimidazol-1-yl}-ethanol | G.1.21 | 1.45 (b) | 378.3 |
| N'2'-(2,2-Dimethylpropyl)-4-[6-(4-fluorophenyl)-imidazo[2,1-b]thiazol-5-yl]-benzene-1,2-diamine [prepared using A from 6-(4-fluorophenyl)-imidazo[2,1-b]thiazole [WO2004110990A2, Example 2, Step 1] and NIS, C from Preparation #B.1, D from 2,2-dimethylpropylamine, E] | 1-(2,2-Dimethylpropyl)-6-[6-(4-fluorophenyl)-imidazo[2,1-b]thiazol-5-yl]-1H-benzoimidazol-2-ylamine | G.1.22 | 1.98 (b) | 420.2 |
| N'2'-(3-Dimethylamino-2,2-dimethylpropyl)-4-[6-(4-fluorophenyl)-imidazo[2,1-b]thiazol-5-yl]-benzene-1,2-diamine [prepared using A from 6-(4-fluorophenyl)-imidazo[2,1-b]thiazole [WO2004110990A2, Example 2, Step 1] and NIS, C from Preparation #B.1, D from 2,2,N'1',N'1'-tetramethylpropane-1,3-diamine, E] | 1-(3-Dimethylamino-2,2-dimethylpropyl)-6-[6-(4-fluorophenyl)-imidazo[2,1-b]thiazol-5-yl]-1H-benzoimidazol-2-ylamine | G.1.23 | 1.49 (b) | 463.3 |
| {5-[6-(4-Fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] and NIS, C using 2-fluoropyridine-5-boronic acid (Asymchem), D using hydrazine) | 6-[6-(4-Fluorophenyl)-imidazo[2,1-b]oxazol-5-yl]-[1,2,4]triazolo[4,3-a]pyridin-3-ylamine | G.1.24 | 1.81 (a) | 335.1 |

General Procedure H: Cyclization of a Diamine with Sodium Nitrite

A mixture of a diamine (preferably 1 equiv) and an acidic aqueous solution (such as 6 M HCl in water) is cooled to about 0° C. Then a solution of sodium nitrite (1-5 equiv, preferably 1-2 equiv) in water is added and the reaction is allowed to warm slowly to ambient temperature. After about 1-18 h (preferably 1-4 h), the reaction is filtered, washing with water, and dried. If necessary, this material is purified by crystallization or trituration from an appropriate solvent or solvents, or by chromatography to give the target compound.

Illustration of General Procedure H

Example #H.1.1

1-(2,2-Dimethylpropyl)-6-[6-(4-fluorophenyl)-imidazo[2,1-b]oxazol-5-yl]-1H-benzotriazole

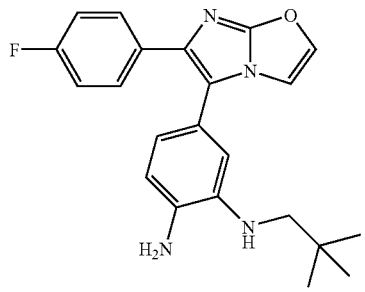
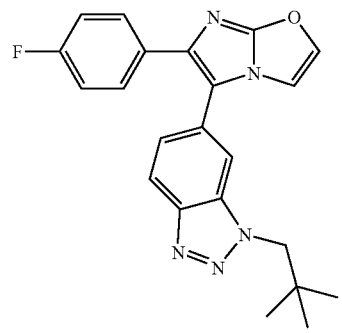

A mixture of N'2'-(2,2-dimethylpropyl)-4-[6-(4-fluorophenyl)-imidazo[2,1-b]oxazol-5-yl]-benzene-1,2-diamine (0.42 g, 0.83 mmol; Preparation #F. 1) and 6 M HCl in water (2.0 mL; VWR) was cooled to about 0° C. Then sodium nitrite (0.086 g, 1.2 mmol) in water (0.75 mL) was added dropwise. After about 2 h, the reaction was filtered, washing with water, and dried in the vacuum oven at about 55-65° C. The resulting solid was crystallized from hot ACN, filtered, washing with ACN, and dried in the vacuum oven at about 55-65° C. to give the title compound (0.19 g, 58%): LC/MS (Table 1, Method b) $R_t$=2.25 min; MS m/z: 390.2 (M+H)$^+$.

TABLE H.1

Examples prepared from diamines using General Procedure H

| Diamine | Product | Example # | $R_t$ min (method) | m/z ESI+ (M + H)$^+$ |
|---|---|---|---|---|
| 4-[6-(4-Fluorophenyl)-imidazo[2,1-b]oxazol-5-yl]-N'2'-isobutyl-benzene-1,2-diamine [prepared using D from Preparation #C.1 and isobutylamine, F using tin(II) chloride dihydrate] | 6-[6-(4-Fluorophenyl)-imidazo[2,1-b]oxazol-5-yl]-1-isobutyl-1H-benzotriazole | H.1.2 | 2.25 (b) | 376.2 |
| 4-[6-(4-Fluorophenyl)-imidazo[2,1-b]oxazol-5-yl]-N'2'-methyl-benzene-1,2-diamine [prepared using D from Preparation #C.1 and 2 M methylamine in THF, F using tin(II) chloride dihydrate] | 6-[6-(4-Fluorophenyl)-imidazo[2,1-b]oxazol-5-yl]-1-methyl-1H-benzotriazole | H.1.3 | 1.96 (b) | 334.1 |
| N'2'-Ethyl-4-[6-(4-fluorophenyl)-imidazo[2,1-b]oxazol-5-yl]-benzene-1,2-diamine [prepared using D from Preparation #C.1 and 2 M ethylamine in THF, F using tin(II) chloride dihydrate] | 1-Ethyl-6-[6-(4-fluorophenyl)-imidazo[2,1-b]oxazol-5-yl]-1H-benzotriazole | H.1.4 | 2.06 (b) | 348.1 |
| 4-[6-(4-Fluorophenyl)-imidazo[2,1-b]oxazol-5-yl]-N'2'-isopropyl-benzene-1,2-diamine [prepared using D from Preparation #C.1 and isopropylamine, F using tin(II) chloride dihydrate] | 6-[6-(4-Fluorophenyl)-imidazo[2,1-b]oxazol-5-yl]-1-isopropyl-1H-benzotriazole | H.1.5 | 2.15 (b) | 362.1 |

TABLE H.1-continued

Examples prepared from diamines using General Procedure H

| Diamine | Product | Example # | R, min (method) | m/z ESI+ (M + H)+ |
|---|---|---|---|---|
| N'2'-Cyclohexyl-4-[6-(4-fluorophenyl)-imidazo[2,1-b]oxazol-5-yl]-benzene-1,2-diamine [prepared using D from Preparation #C.1 and cyclohexylamine, F using tin(II) chloride dihydrate] | 1-Cyclohexyl-6-[6-(4-fluorophenyl)-imidazo[2,1-b]oxazol-5-yl]-1H-benzotriazole | H.1.6 | 2.42 (b) | 402.2 |
| 4-[6-(4-Fluorophenyl)-imidazo[2,1-b]oxazol-5-yl]-benzene-1,2-diamine [prepared using D from Preparation #C.1 and (1-methyl-1H-pyrrol-2-yl)methylamine, F using tin(II) chloride dihydrate] | 6-[6-(4-Fluorophenyl)-imidazo[2,1-b]oxazol-5-yl]-1H-benzotriazole | H.1.7 | 1.80 (b) | 320.1 |
| N'2'-Cyclopropylmethyl-4-[6-(4-fluorophenyl)-imidazo[2,1-b]oxazol-5-yl]-benzene-1,2-diamine [prepared using D from Preparation #C.1 and cyclopropylmethyl-amine, F using tin(II) chloride dihydrate] | 1-Cyclopropylmethyl-6-[6-(4-fluorophenyl)-imidazo[2,1-b]oxazol-5-yl]-1H-benzotriazole | H.1.8 | 2.11 (b) | 374.2 |
| N'2'-Benzyl-4-[6-(4-fluorophenyl)-imidazo[2,1-b]oxazol-5-yl]-benzene-1,2-diamine [prepared using D from Preparation #C.1 and benzylamine, F using tin(II) chloride dihydrate] | 1-Benzyl-6-[6-(4-fluorophenyl)-imidazo[2,1-b]oxazol-5-yl]-1H-benzotriazole | H.1.9 | 2.20 (b) | 410.1 |
| N'2'-tert-Butyl-4-[6-(4-fluorophenyl)-imidazo[2,1-b]oxazol-5-yl]-benzene-1,2-diamine [prepared using D from Preparation #C.1 and tert-butylamine, F using tin(II) chloride dihydrate] | 1-tert-Butyl-6-[6-(4-fluorophenyl)-imidazo[2,1-b]oxazol-5-yl]-1H-benzotriazole | H.1.10 | 2.18 (b) | 376.2 |
| 4-[6-(4-Fluorophenyl)-imidazo[2,1-b]oxazol-5-yl]-N'2'-phenyl-benzene-1,2-diamine [prepared using D from Preparation #C.1 and aniline, F using tin(II) chloride dihydrate] | 6-[6-(4-Fluorophenyl)-imidazo[2,1-b]oxazol-5-yl]-1-phenyl-1H-benzotriazole | H.1.11 | 2.26 (b) | 454.2 |

TABLE H.2

Examples prepared from diamines using General Procedure H

| Diamine | Product | Example # | R, min (method) | m/z ESI+ (M + H)+ |
|---|---|---|---|---|
| 5-(6-(2,4-Difluorophenyl)imidazo[2,1-b]oxazol-5-yl)-N1-isopropylbenzene-1,2-diamine [prepared using C from Example #2, step A with Preparation #B.1, D with isopropylamine, F using tin(II) chloride dihydrate] | 6-(2,4-Difluorophenyl)-5-(1-isopropyl-1H-benzo[d][1,2,3]triazol-6-yl)imidazo[2,1-b]oxazole | H.2.1 | 2.61 (a) | 380.2 |

TABLE H.2-continued

Examples prepared from diamines using General Procedure H

| Diamine | Product | Example # | R, min (method) | m/z ESI+ (M + H)+ |
|---|---|---|---|---|
| 5-(6-(2,4-Difluorophenyl)imidazo[2,1-b]oxazol-5-yl)-N1-(1-methylcyclobutyl)benzene-1,2-diamine [prepared using C from Example #2, step A with Preparation #B.1, D with 1-methylcyclobutylamine, F using tin(II) chloride dehydrate] | 6-(2,4-Difluorophenyl)-5-(1-(1-methylcyclobutyl)-1H-benzo[d][1,2,3]triazol-6-yl)imidazo[2,1-b]oxazole | H.2.2 | 2.81 (a) | 406.2 |
| 3-(2-Amino-5-(6-(2,4-difluorophenyl)imidazo[2,1-b]oxazol-5-yl)phenylamino)-2,2-dimethylpropan-1-ol [prepared using C from Example #2, step A with Preparation #B.1, D with 3-amino-2,2-dimethylpropan-1-ol, F using tin(II) chloride dihydrate] | 3-(6-(6-(2,4-Difluorophenyl)imidazo[2,1-b]oxazol-5-yl)-1H-benzo[d][1,2,3]triazol-1-yl)-2,2-dimethylpropan-1-ol | H.2.3 | 2.39 (a) | 424.1 |
| 1-(2-Amino-5-(6-(2,4-difluorophenyl)imidazo[2,1-b]oxazol-5-yl)phenylamino)-2-methylpropan-2-ol [prepared using C from Example #2, step A with Preparation #B.1, D with 1-amino-2-methylpropan-2-ol, F using tin(II) chloride dihydrate | 1-(6-(6-(2,4-Difluorophenyl)imidazo[2,1-b]oxazol-5-yl)-1H-benzo[d][1,2,3]triazol-1-yl)-2-methylpropan-2-ol | H.2.4 | 2.26 (a) | 410.1 |

General Procedure I: Cyclization of a Pyridin-2-ylhydrazine with an Acid Chloride A mixture of a substituted pyridin-2-ylhydrazine (preferably 1 equiv) and an acid chloride (1-10 equiv, preferably 5-10 equiv) was heated at reflux for about 1-18 h (preferably 2-6 h). The reaction is cooled to ambient temperature. A nonpolar organic solvent (such as heptane or hexane) is added and stirring is continued for about 10-30 min (preferably 15 min). The mixture is filtered, washing with additional solvent, to give the target compound as an HCl salt. Alternatively, the HCl salt is reacted with a base such as 1N NaOH to give the free base of the target compound. The crude product is purified by crystallization or trituration from an appropriate solvent or solvents, or by chromatography to give the target compound.

Illustration of General Procedure I

Preparation #I.1:
6-Bromo-3-isobutyl-1,2,4-triazolo[4,3-a]pyridine

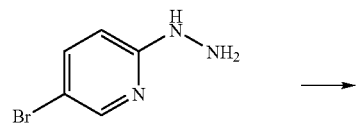

→

-continued

A mixture of 5-bromo-2-hydrazinopyridine (1.00 g, 5.00 mmol; Frontier) and isovaleryl chloride (5.50 mL, 45.1 mmol) was heated at reflux for about 3 h. The reaction was cooled to ambient temperature then heptane (5 mL) was added and the reaction was stirred for about 15 min. The mixture was filtered, washing with additional heptane, and suspended in water/DCM (1:1, 20 mL) then added 1N NaOH (3.5 mL). This mixture was stirred for about 15 min. The layers were separated and the aqueous layer was extracted with DCM (2×10 mL). The combined organic layers were washed with brine, dried over MgSO$_4$, filtered, and concentrated to give the title compound (0.86 g, 65%): LC/MS (Table 1, Method b) R$_t$ =1.87 min; MS m/z: 254.0 (M+H)$^+$.

TABLE I.1

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] and NIS, C using 2-fluoropyridine-5-boronic acid [Asymchem], D using hydrazine) using General Procedure I

| Acid chloride | Product | Example # | R, min (method) | m/z ESI+ (M + H)+ |
|---|---|---|---|---|
| Cyclopropanecarbonyl chloride | 3-Cyclopropyl-6-[6-(4-fluorophenyl)-imidazo[2,1-b]oxazol-5-yl]-[1,2,4]triazolo[4,3-a]pyridine | I.1.1 | 2.07 (a) | 369.3 |
| Cyclobutanecarbonyl chloride | 3-Cyclobutyl-6-[6-(4-fluorophenyl)-imidazo[2,1-b]oxazol-5-yl]-[1,2,4]triazolo[4,3-a]pyridine | I.1.2 | 2.19 (a) | 374.2 |

General Procedure I.1: Cyclization of a pyridin-2-ylhydrazine with an Acid Chloride A mixture of a substituted pyridin-2-ylhydrazine (preferably 1 equiv) and an acid chloride (1-20 equiv, preferably 5-10 equiv) was heated at reflux for about 1-18 h (preferably about 2-6 h). The reaction is cooled to ambient temperature. Optionally, an organic solvent (such as heptane, hexane, EtOAc or MeOH, preferably heptane or EtOAc) and/or water or an aqueous base (such as saturated aqueous $NaHCO_3$) is added and stirring is continued for about 0-30 min (preferably about 15-30 min). If a solid is present, the mixture is filtered, washing with additional solvent, to give the target compound. Alternatively, the reaction mixture is optionally concentrated under reduced pressure and partitioned between water or an aqueous base (for example, saturated aqueous $NaHCO_3$) and an organic solvent (such as DCM). The layers are separated and the aqueous layer may be extracted with additional organic solvent (such as DCM). The combined organic layers may be optionally washed with brine, dried over $Na_2SO_4$ or $MgSO_4$, then decanted or filtered prior to concentrating under reduced pressure. In either case, the crude product is optionally purified by crystallization and/or trituration from an appropriate solvent or solvents and/or by chromatography to give the target compound.

Illustration of General Procedure I.1

Example #I.1.1

5-(3-Cyclobutyl-[1,2,4]triazolo[4,3a]pyridin-6-yl)-6-(2,4,5-trifluorophenyl)imidazo[2,1-b]oxazole

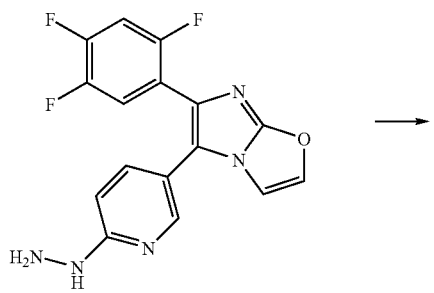

To a round bottom flask was added 5-(6-hydrazinylpyridin-3-yl)-6-(2,4,5-trifluorophenyl)imidazo[2,1-b]oxazole (0.30 g, 0.87 mmol; prepared using A from Preparation #0.1 with NIS, C with 2-fluoropyridine-5-boronic acid [Asymchem], D with hydrazine) and cyclobutanecarbonyl chloride (1.5 mL, 13 mmol). The reaction mixture was heated to about 100° C. for about 1 h. The reaction mixture was diluted with heptane and filtered. The solid was dissolved in DCM (50 mL) and the organic layer was washed with saturated aqueous $NaHCO_3$ (50 mL), dried with $MgSO_4$, filtered and concentrated under reduced pressure. The crude solid was purified by flash chromatography (silica gel; DCM/MeOH gradient from 1:0 to 19:1) to give the title compound (0.28 g, 78%): LC/MS (Table 1, Method a) $R_t$=2.26 min; MS m/z: 410.1 (M+H)+.

TABLE I.1.1

Examples prepared from 5-(6-hydrazinylpyridin-3-yl)-6-(2,4,5-trifluorophenyl)imidazo[2,1-b]oxazole (prepared using A from Preparation #O.1 with NIS, C with 2-fluoropyridine-5-boronic acid [Asymchem], D with hydrazine) using General Procedure I.1

| Acid Chloride | Product | Example # | $R_t$ min (method) | m/z ESI+ $(M + H)^+$ |
|---|---|---|---|---|
| 2-Methylbutyryl chloride | 5-(3-sec-Butyl-[1,2,4]triazolo[4,3-a]pyridin-6-yl)-6-(2,4,5-trifluorophenyl)imidazo[2,1-b]oxazole | I.1.1.2 | 2.29 (a) | 412.2 |
| 2-Methylcyclopropanecarbonyl chloride [Oakwood] | 5-(3-(2-Methylcyclopropyl)-[1,2,4]triazolo[4,3-a]pyridin-6-yl)-6-(2,4,5-trifluorophenyl)imidazo[2,1-b]oxazole | I.1.1.3 | 2.27 (a) | 410.1 |

TABLE I.1.2

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine) using General Procedure I.1

| Acid Chloride | Product | Example # | $R_t$ min (method) | m/z ESI+ $(M + H)^+$ |
|---|---|---|---|---|
| 2-Cyclohexylacetyl chloride | 5-(3-(Cyclohexylmethyl)-[1,2,4]triazolo[4,3-a]pyridin-6-yl)-6-(4-fluorophenyl)imidazo[2,1-b]oxazole | I.1.2.1 | 2.59 (a) | 416.1 |
| 2-(Tetrahydrofuran-2-yl)acetyl chloride | 6-(4-Fluorophenyl)-5-(3-((tetrahydrofuran-2-yl)methyl)-[1,2,4]triazolo[4,3-a]pyridin-6-yl)imidazo[2,1-b]oxazole | I.1.2.2 | 2.08 (a) | 404.1 |

TABLE I.1.3

Examples prepared from cyclobutanecarbonyl chloride using General Procedure I.1

| Pyridin-2-ylhydrazine | Product | Example # | $R_t$ min (method) | m/z ESI+ $(M + H)^+$ |
|---|---|---|---|---|
| 6-(2,4-Difluorophenyl)-5-(6-hydrazinylpyridin-3-yl)imidazo[2,1-b]thiazole (prepared using C from Preparation #1 with 2-fluoropyridine-5-boronic acid [Asymchem], D with hydrazine) | 5-(3-Cyclobutyl-[1,2,4]triazolo[4,3-a]pyridin-6-yl)-6-(2,4-difluorophenyl)imidazo[2,1-b]thiazole | I.1.3.1 | 2.23 (a) | 408.1 |
| 6-(2,4-Difluorophenyl)-5-(6-hydrazinylpyridin-3-yl)-2-methylimidazo[2,1-b]oxazole (prepared using O from 2-bromo-2',4'-difluoroacetophenone with Preparation #2, A with NIS, C with 2-fluoropyridine-5-boronic acid [Asymchem], D with hydrazine) | 5-(3-Cyclobutyl-[1,2,4]triazolo[4,3-a]pyridin-6-yl)-6-(2,4-difluorophenyl)-2-methylimidazo[2,1-b]oxazole | I.1.3.2 | 2.31 (a) | 406.1 |
| 6-(4-Fluoro-2-(trifluoromethyl)phenyl)-5-(6-hydrazinylpyridin-3-yl)imidazo[2,1-b]oxazole (prepared using N from 4'-fluoro-2'- | 5-(3-Cyclobutyl-[1,2,4]triazolo[4,3-a]pyridin-6-yl)-6-(4-fluoro-2-(trifluoromethyl)phenyl)imidazo[2,1-b]oxazole | I.1.3.3 | 2.29 (a) | 442.1 |

TABLE I.1.3-continued

Examples prepared from cyclobutanecarbonyl chloride using General Procedure I.1

| Pyridin-2-ylhydrazine | Product | Example # | R<sub>t</sub> min (method) | m/z ESI+ (M + H)+ |
|---|---|---|---|---|
| (trifluoromethyl)acetophenone [Alfa Aesar], O with oxazole-2-amine [GL Synthesis], A with NIS, C with 2-fluoropyridine-5-boronic acid [Asymchem], D with hydrazine) | | | | |
| {5-[6-(2-Chloro-4-fluorophenyl)-imidazo[2,1-b]oxazol-5-yl]-pyridin-2-yl}-hydrazine (prepared using N from 2'-Chloro-4'-fluoroacetophenone [Alfa Aesar], O with oxazole-2-amine [GL Synthesis], A with NIS, C with 2-fluoropyridine-5-boronic acid [Asymchem], D with hydrazine) | 6-(2-Chloro-4-fluorophenyl)-5-(3-cyclobutyl-[1,2,4]triazolo[4,3-a]pyridin-6-yl)imidazo[2,1-b]oxazole | I.1.3.4 | 2.22 (a) | 408.1 |
| {5-[6-(3,4,5-Trifluorophenyl)-imidazo[2,1-b]oxazol-5-yl]-pyridin-2-yl}-hydrazine (prepared using N from 3',4',5'-trifluoroacetophenone [Oakwood], O with oxazole-2-amine [GL Synthesis], A with NIS, C with 2-fluoropyridine-5-boronic acid [Asymchem], D with hydrazine) | 5-(3-Cyclobutyl-[1,2,4]triazolo[4,3-a]pyridin-6-yl)-6-(3,4,5-trifluorophenyl)imidazo[2,1-b]oxazole | I.1.3.5 | 2.45 (a) | 410.1 |
| {5-[6-(2,4-Dichlorophenyl)-imidazo[2,1-b]oxazol-5-yl]-pyridin-2-yl}-hydrazine (prepared using O from 2-bromo-2',4'-dichloroacetophenone with oxazole-2-amine [GL Synthesis], A with NIS, C with 2-fluoropyridine-5-boronic acid [Asymchem], D with hydrazine) | 5-(3-Cyclobutyl-[1,2,4]triazolo[4,3-a]pyridin-6-yl)-6-(2,4-dichlorophenyl)imidazo[2,1-b]oxazole | I.1.3.6 | 2.39 (a) | 424.1 |
| {5-[6-(4-Chlorophenyl)-imidazo[2,1-b]oxazol-5-yl]-pyridin-2-yl}-hydrazine (prepared using O from 2-bromo-4'-chloroacetophenone with oxazole-2-amine [GL Synthesis], A with NIS, C with 2-fluoropyridine-5-boronic acid [Asymchem], D with hydrazine) | 6-(4-Chlorophenyl)-5-(3-cyclobutyl-[1,2,4]triazolo[4,3-a]pyridin-6-yl)imidazo[2,1-b]oxazole | I.1.3.7 | 2.41 (a) | 390.1 |
| {5-[6-(4-Fluorophenyl)-imidazo[2,1-b]thiazol-5-yl]-pyridin-2-yl}-hydrazine (prepared using A from 6-(4-fluorophenyl)-imidazo[2,1-b]thiazole [prepared according to WO2004110990A2, Example 2, Steps 1] with NIS, C with 2-fluoropyridine-5-boronic | 3-Cyclobutyl-6-[6-(4-fluorophenyl)imidazo[2,1-b]thiazol-5-yl]-[1,2,4]triazolo[4,3-a]pyridine | I.1.3.8 | 1.96 (d) | 390.1 |

TABLE I.1.3-continued

Examples prepared from cyclobutanecarbonyl chloride using General Procedure I.1

| Pyridin-2-ylhydrazine | Product | Example # | R,min (method) | m/z ESI+ (M + H)+ |
|---|---|---|---|---| acid [Asymchem], D with hydrazine)

General Procedure J: Amide Formation Followed by Cyclization with Thionyl Chloride A solution of a heteroaryl hydrazine (preferably 1 equiv) in an appropriate organic solvent (such as THF, 1,4-dioxane, or DCM, preferably THF or DCM) was treated with a carboxylic acid or acid chloride (1.0 to 1.05 equiv, preferably 1 equiv) and either a peptide coupling reagent (such as HBTU/HOBT, HATU, EDCI, or DCC/HOBT, but preferably EDCI) (0.1-5 equiv, preferably 1 equiv) or a base (such as DIEA or TEA, preferably TEA) (1-4 equiv, preferably 2 equiv), respectively. The reaction mixture is stirred at about 20-60° C. (preferably ambient temperature). Upon completion as monitored by LC/MS, the reaction mixture is concentrated to dryness and the crude product is used directly in the next reaction. Alternately, the reaction mixture can be washed with water, partitioned, and dried over an appropriate drying agent (such as $MgSO_4$ or $Na_2SO_4$). The organic solution is then concentrated to dryness under reduced pressure. The crude intermediate is dissolved in an appropriate organic solvent (such as THF or 1,4-dioxane, preferably 1,4-dioxane) and is treated with thionyl chloride (1-10 equiv, preferably 2.5 equiv) and is stirred at about 80-120° C. (preferably 100° C.) for about 0.5-15 h (preferably 3 h). Upon completion, the mixture is cooled to about 0° C. and the precipitate is collected by vacuum filtration. This solid may be dissolved in an organic solvent (such as EtOAc, DCM, or EtOAc/MeOH) and washed with water. The layers are separated and the aqueous layer is optionally extracted with additional organic solvent. The combined organic layers may be optionally washed with brine, dried over $Na_2SO_4$ or $MgSO_4$, then decanted or filtered, prior to concentrating under reduced pressure. Additionally, the material is optionally further purified by crystallization or trituration from an appropriate solvent or solvents, or by chromatography to give the target compound.

Illustration of General Procedure J

Example #J.1.1

3-(2-Chlorophenyl)-6-[6-(4-fluorophenyl)-imidazo[2,1-b]oxazol-5-yl]-[1,2,4]triazolo[4,3a]pyridine

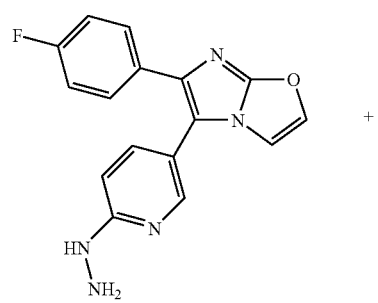

+

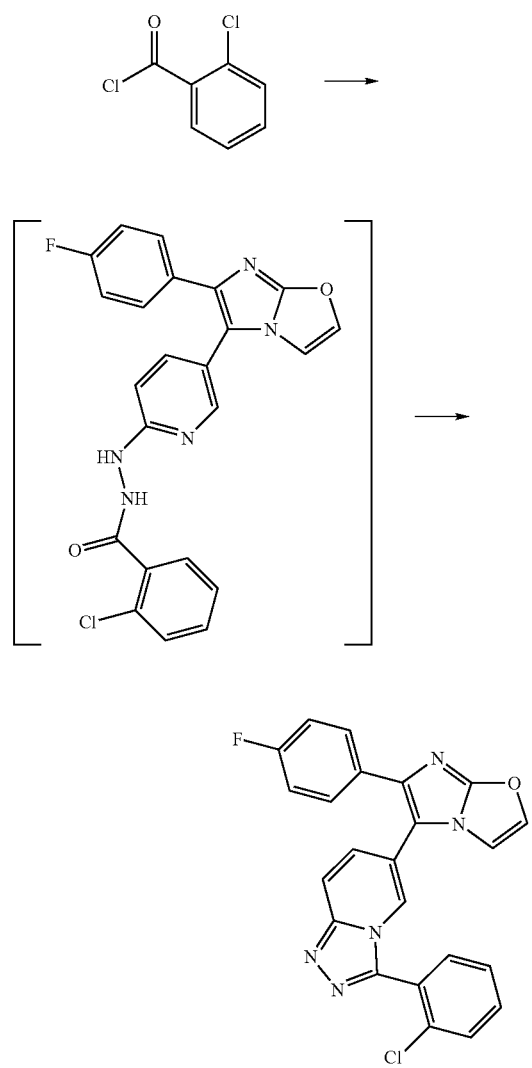

A 100 mL round-bottom flask charged with 6-(4-fluorophenyl)-5-(6-hydrazinylpyridin-3-yl)imidazo[2,1-b]oxazole (0.35 g, 1.1 mmol; prepared from A using 6-(4-fluorophenyl)-imidazo[2,1-b]oxazole [WO2004110990A2, Example 1, Steps 1-3], and NIS, C using 6-fluoropyridin-3-ylboronic acid [Asymchem], and D using 1M hydrazine in THF) in THF (10 mL) and DCM (10 mL) was treated with TEA (0.17 mL, 1.2 mmol) and 2-chlorobenzoyl chloride (0.14 mL, 1.1 mmol). The reaction mixture was stirred at ambient temperature for about 30 min. The reaction mixture was then washed with water, dried over $MgSO_4$, filtered, and evaporated under reduced pressure to give 2-chloro-N'-(5-(6-(4-fluorophenyl)imidazo[2,1-b]oxazol-5-yl)pyridin-2-yl)benzohydrazide (0.50 g, 1.1 mmol, 89%). The crude material was dissolved in 1,4-dioxane (10 mL) and treated with thionyl chloride (0.2 mL, 2.8 mmol). After about 30 min at about 100° C., the reaction mixture was cooled to about 0° C. and the precipitate was collected by filtration and washed with DCM (5 mL). The solid was dissolved in EtOAc/MeOH and washed twice with water. The organic layer was dried over MgSO$_4$, filtered, and concentrated under reduced pressure. The mixture was purified by column chromatography using EtOAc then EtOAc/MeOH (98:2) as eluent and dried in a vacuum oven at about 50° C. to give the title compound as a tan solid (0.13 g, 27%): LC/MS (Table 1, Method a) R$_t$=2.38 min; MS m/z: 430.1 (M+H)$^+$.

brine, dried over Na$_2$SO$_4$ or MgSO$_4$, then decanted or filtered, prior to concentrating under reduced pressure. Alternatively, the reaction mixture can be concentrated in vacuo. Additionally, the material is optionally further purified by crystallization or trituration from an appropriate solvent or solvents, or by chromatography to give the target compound.

Illustration of General Procedure J.1

Example #J.1.1.1

6-(4-Fluorophenyl)-5-(3-(2-methylcyclopropyl)-[1,2,4]triazolo[4,3-]pyridin-6-yl)imidazo[2,1-b]oxazole

TABLE J.1

Examples prepared from 2-chloro-N'-(5-(6-(4-fluorophenyl)-imidazo[2,1-b]oxazol-5-yl)pyridin-2-yl)benzohydrazide [prepared from A using 6-(4-fluorophenyl)-imidazo[2,1-b]oxazole [WO2004110990A2, Example 1, Steps 1-3] and NIS, C using 6-fluoropyridin-3-ylboronic acid [Asymchem], and D using 1 M hydrazine in THF] using General Procedure J.

| Carboxylic Acid or Acid Chloride | Product | Example # | R$_t$ min (method) | m/z ESI+ (M + H)$^+$ |
|---|---|---|---|---|
| Pivaloyl chloride | 3-tert-Butyl-6-[6-(4-fluorophenyl)-imidazo[2,1-b]oxazol-5-yl]-[1,2,4]triazolo[4,3-a]pyridine | J.1.2 | 2.24 (a) | 376.1 |
| 1-Methylcyclopropane-1-carboxylic acid | 6-[6-(4-Fluorophenyl)-imidazo[2,1-b]oxazol-5-yl]-3-(1-methylcyclopropyl)-[1,2,4]triazolo[4,3-a]pyridine | J.1.3 | 2.15 (a) | 374.2 |

General Procedure J.1: Amide Formation with a Carboxylic Acid Followed by Cyclization with Thionyl Chloride A solution of a heteroaryl hydrazine (preferably 1 equiv) in an appropriate organic solvent (such as THF, 1,4-dioxane, or DCM, preferably THF or DCM) is treated with a carboxylic acid (1.0 to 5.0 equiv, preferably 1.0 to 2.0 equiv) and a peptide coupling reagent (such as HBTU/HOBT, HATU, EDCI, or DCC/HOBT, preferably EDCI) (0.1-5 equiv, preferably 1 equiv). The reaction mixture is stirred at about 20-60° C. (preferably ambient temperature) for about 1-48 h (preferably about 1-18 h). The reaction mixture is concentrated to dryness and the crude product is used directly in the next reaction. Alternately, the reaction mixture can be diluted with water, partitioned with an organic solvent (such as EtOAc or DCM), optionally filtered, washed with water, and dried over an appropriate drying agent (such as MgSO$_4$ or Na$_2$SO$_4$). The organic solution is then concentrated to dryness under reduced pressure. The crude intermediate is dissolved in an appropriate organic solvent (such as THF or 1,4-dioxane, preferably 1,4-dioxane) and is treated with thionyl chloride (1-10 equiv, preferably 2.5 equiv) and is stirred at about 80-120° C. (preferably about 100° C.) for about 0.5-15 h (preferably about 3-4 h). Upon completion, the mixture is cooled to about 0° C. and the precipitate is collected by vacuum filtration. This solid may be dissolved in an organic solvent (such as EtOAc, DCM, or EtOAc/MeOH) and washed with water. The layers are separated and the aqueous layer is optionally extracted with additional organic solvent. The combined organic layers may be optionally washed with

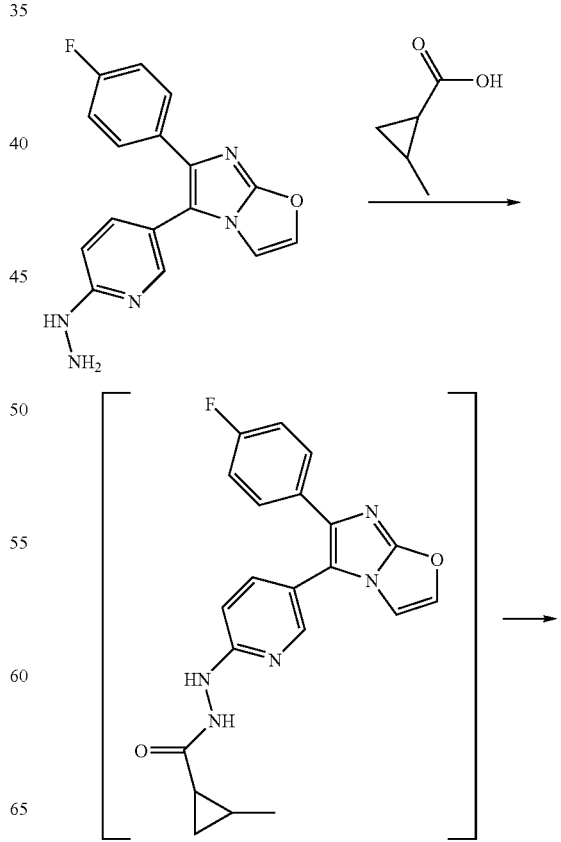

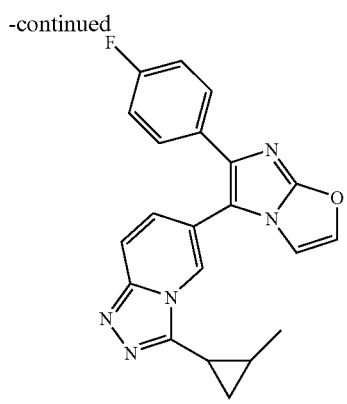

In a round bottom flask was added 6-(4-fluorophenyl)-5-(6-hydrazinylpyridin-3-yl)imidazo[2,1-b]oxazole (0.300 g, 0.970 mmol; prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine), DCM (10 mL), 2-methylcyclopropanecarboxylic acid (0.094 mL, 0.970 mmol) and EDCI (0.186 g, 0.970 mmol). The reaction mixture was stirred overnight at ambient temperature. An additional amount of 2-methylcyclopropanecarboxylic acid (0.094 mL, 0.970 mmol) and EDCI (0.186 g, 0.970 mmol) was added. The reaction was stirred for about 6 h. Water was added and the layers were partitioned. A grey solid was filtered and discarded. The organic layer was washed with water, dried over $MgSO_4$, filtered and evaporated under reduced pressure to give crude intermediate. The crude intermediate was added to a 125 mL round-bottomed flask followed by dioxane (10 mL) to give a brown suspension. Thionyl chloride (0.065 mL, 0.89 mmol) was added and the reaction mixture was stirred at about 100° C. After about 4 h, the reaction mixture was cooled to ambient temperature and the solvent removed in vacuo. The crude material was purified directly by flash chromatography (silica gel; DCM/MeOH gradient from 1:0 to 19:1) to give the title compound (0.079 g, 36%). LC/MS (Table 1, Method a) $R_t$, =2.17 min; MS 374.2 m/z $(M+H)^+$.

TABLE J.1.1

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] with NIS, C using 2-fluoropyridine-5-boronic acid [Asymchem], D using hydrazine) using General Procedure J.1

| Carboxylic Acid | Product | Example # | $R_t$ min (method) | m/z ESI+ $(M + H)^+$ |
|---|---|---|---|---|
| 1-(Trifluoromethyl)cyclopropanecarboxylic acid [Matrix] | 6-(4-Fluorophenyl)-5-(3-(1-(trifluoromethyl)cyclopropyl)-[1,2,4]triazolo[4,3-a]pyridin-6-yl)imidazo[2,1-b]oxazole | J.1.1.2 | 2.42 (a) | 428.1 |
| 1-(Trifluoromethyl)cyclobutanecarboxylic acid [Matrix] | 6-(4-Fluorophenyl)-5-(3-(1-(trifluoromethyl)cyclobutyl)-[1,2,4]triazolo[4,3-a]pyridin-6-yl)imidazo[2,1-b]oxazole | J.1.1.3 | 2.51 (a) | 442.1 |
| 1-(tert-Butoxycarbonyl)-4-methylpiperidine-4-carboxylic acid [Arch] | tert-Butyl 4-(6-(6-(4-fluorophenyl)imidazo[2,1-b]oxazol-5-yl)-[1,2,4]triazolo[4,3-a]pyridin-3-yl)-4-methylpiperidine-1-carboxylate | J.1.1.4 | 2.56 (a) | 517.2 |

TABLE J.1.2

Examples prepared from {5-[6-(4-chloro-2-fluorophenyl)-imidazo[2,1-b]oxazol-5-yl]-pyridin-2-yl}-hydrazine (prepared using N from 4'-chloro-2'-fluoroacetophenone [Oakwood], O with oxazole-2-amine [GL Synthesis], A with NIS, C with 2-fluoropyridine-5-boronic acid [Asymchem], D with hydrazine) using General Procedure J.1

| Carboxylic Acid | Product | Example # | $R_t$ min (method) | m/z ESI + $(M + H)^+$ | A# |
|---|---|---|---|---|---|
| 1-Methylcyclopropanecarboxylic acid | 6-(4-Chloro-2-fluorophenyl)-5-(3-(1-methylcyclopropyl)-[1,2,4]triazolo[4,3-a]pyridin-6-yl)imidazo[2,1-b]oxazole | J.1.2.1 | 2.26 (a) | 408.1 | A-974307.0 |
| Cyclobutanecarboxylic acid | 6-(4-Chloro-2-fluorophenyl)-5-(3-cyclobutyl-[1,2,4]triazolo[4,3-a]pyridin-6-yl)imidazo[2,1-b]oxazole | J.1.2.2 | 2.45 (a) | 408.1 | A-976300.0 |

TABLE J.1.3

Examples prepared from {5-[6-(3-trifluoromethylphenyl)-imidazo[2,1-b]oxazol-5-yl]-pyridin-2-yl}-hydrazine (prepared using N from 3'-trifluoromethylacetopheonone, O with oxazole-2-amine [GL Synthesis], A with NIS, C with 2-fluoropyridine-5-boronic acid [Asymchem], D with hydrazine) using General Procedure J.1

| Carboxylic Acid | Product | Example # | $R_t$ min (method) | m/z ESI+ $(M + H)^+$ |
|---|---|---|---|---|
| 1-Methylcyclopropanecarboxylic acid | 5-(3-(1-Methylcyclopropyl)-[1,2,4]triazolo[4,3-a]pyridin-6-yl)-6-(3-(trifluoromethyl)phenyl)imidazo[2,1-b]oxazole | J.1.3.1 | 2.43 (a) | 424.1 |

TABLE J.1.4

Examples prepared from {5-[6-(2-chloro-4-fluorophenyl)-imidazo[2,1-b]oxazol-5-yl]-pyridin-2-yl}-hydrazine (prepared using N from 2'-chloro-4'-fluorophenylacetophenone [Lancaster], O with oxazole-2-amine [GL Synthesis], A with NIS, C with 2-fluoropyridine-5-boronic acid [Asymchem], D with hydrazine) using General Procedure J.1

| Carboxylic Acid | Product | Example # | $R_t$ min (method) | m/z ESI+ $(M + H)^+$ |
|---|---|---|---|---|
| 1-Methylcyclopropanecarboxylic acid | 6-(2-Chloro-4-fluorophenyl)-5-(3-(1-methylcyclopropyl)-[1,2,4]triazolo[4,3-a]pyridin-6-yl)imidazo[2,1-b]oxazole | J.1.4.1 | 2.14 (a) | 408.1 |

TABLE J.1.5

Examples prepared from {5-[6-(2,4-dichlorophenyl)-imidazo[2,1-b]oxazol-5-yl]-pyridin-2-yl}-hydrazine (prepared using O from 2-bromo-2',4'-dichloroacetophenone with oxazole-2-amine [GL Synthesis], A with NIS, C with 2-fluoropyridine-5-boronic acid [Asymchem], D with hydrazine) using General Procedure J.1

| Carboxylic Acid | Product | Example # | $R_t$ min (method) | m/z ESI+ $(M + H)^+$ |
|---|---|---|---|---|
| 1-Methylcyclopropanecarboxylic acid | 6-(2,4-Dichlorophenyl)-5-(3-(1-methylcyclopropyl)-[1,2,4]triazolo[4,3-a]pyridin-6-yl)imidazo[2,1-b]oxazole | J.1.5.1 | 2.33 (a) | 424.1 |
| Pivalic acid | 5-(3-tert-Butyl-[1,2,4]triazolo[4,3-a]pyridin-6-yl)-6-(2,4-dichlorophenyl)imidazo[2,1-b]oxazole | J.1.5.2 | 2.46 (a) | 426.1 |

TABLE J.1.6

Examples prepared from {5-[6-(2,4-Difluorophenyl)-imidazo[2,1-b]oxazol-5-yl]-pyridin-2-yl}-hydrazine, (Example #2, step B) using General Procedure J.1

| Carboxylic Acid | Product | Example # | $R_t$ min (method) | m/z ESI+ $(M + H)^+$ |
|---|---|---|---|---|
| 2-Cyclopropylacetic acid | 5-(3-(Cyclopropylmethyl)-[1,2,4]triazolo[4,3-a]pyridin-6-yl)-6-(2,4-difluorophenyl)imidazo[2,1-b]oxazole | J.1.6.1 | 2.12 (a) | 392.2 |
| 1-Methylcyclopropanecarboxylic acid | 6-(2,4-Difluorophenyl)-5-(3-(1-methylcyclopropyl)-[1,2,4]triazolo[4,3-a]pyridin-6-yl)imidazo[2,1-b]oxazole | J.1.6.2 | 1.81 (a) | 392.1 |

TABLE J.1.7

Examples prepared from {5-[6-(2,4,5-trifluorophenyl)-imidazo[2,1-b]oxazol-5-yl]-pyridin-2-yl}-hydrazine (prepared using A from Preparation #O.1 with NIS, C with 2-fluoropyridine-5-boronic acid [Asymchem], D with hydrazine) using General Procedure J.1

| Carboxylic Acid | Product | Example # | R$_t$ min (method) | m/z ESI+ (M + H)$^+$ |
|---|---|---|---|---|
| 2-Cyclopropylacetic acid | 5-(3-(Cyclopropylmethyl)-[1,2,4]triazolo[4,3-a]pyridin-6-yl)-6-(2,4,5-trifluorophenyl)imidazo[2,1-b]oxazole | J.1.7.1 | 2.22 (a) | 410.1 |
| 1-Methylcyclopropanecarboxylic acid | 5-(3-(1-Methylcyclopropyl)-[1,2,4]triazolo[4,3-a]pyridin-6-yl)-6-(2,4,5-trifluorophenyl)imidazo[2,1-b]oxazole | J.1.7.2 | 2.20 (a) | 410.1 |

General Procedure K: Hydrazone Formation Followed by Cyclization with Iodobenzene Diacetate A mixture of a substituted pyridine-2-yl-hydrazine (preferably 1 equiv), an aldehyde (1-5 equiv, preferably 1 equiv) and a suitable organic solvent (such as MeOH and/or DCM) with or preferably without about 1-5 drops (preferably 3 drops) of a suitable acid (such as HOAc, HCl, or H$_2$SO$_4$, preferably HOAc) are heated at about 22-60° C. (preferably 50-60° C.) for about 0.5-24 h (preferably 0.5-12 h). After this time, the reaction is concentrated under reduced pressure then redissolved in a suitable organic solvent (such as DCM or MeOH) and iodobenzene diacetate (1-3 equiv, preferably 1 equiv) is added. The reaction is allowed to stir at ambient temperature for about 0.5-8 h (preferably 1 h). If the product precipitates during the reaction or upon cooling, it is directly filtered and dried. Alternatively, the mixture may be concentrated under reduced pressure and purified by chromatography, trituration with an appropriate solvent, or crystallization from one or more solvents to yield the target compound.

Illustration of General Procedure K

Example #K.1.1

3-(2-Fluorophenyl)-6-[6-(4-fluorophenyl)-imidazo[2,1-b]oxazol-5-yl]-1,2,4]triazolo[4,3-a]pyridine

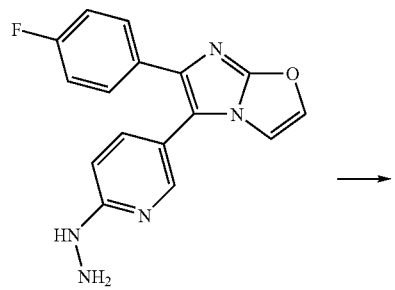

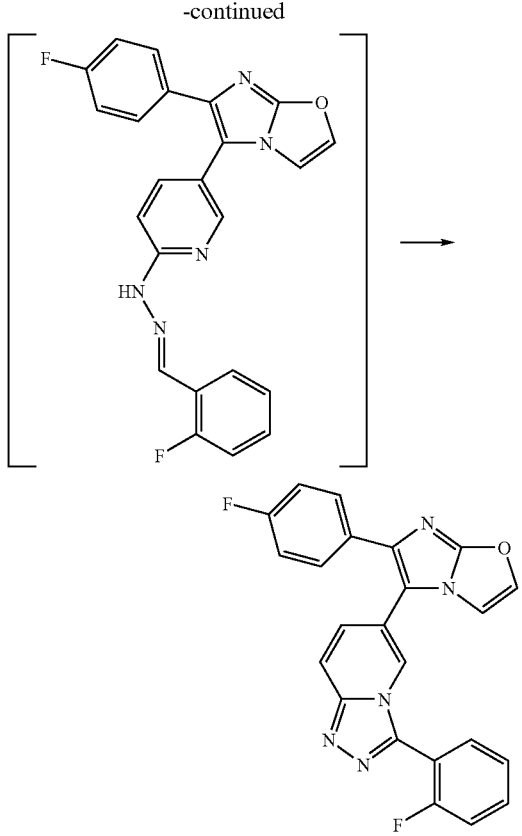

A mixture of {5-[6-(4-fluorophenyl)-imidazo[2,1-b]oxazol-5-yl]-pyridin-2-yl}-hydrazine (0.25 g, 0.81 mmol; prepared using A from 6-(4-fluorophenyl)-imidazo[2,1-b]oxazole [prepared according to WO2004110990A2, Example 1, Steps 1-3] and NIS, C using 2-fluoropyridine-5-boronic acid [Asymchem], D using hydrazine) and 2-fluorobenzaldehyde (0.08 g, 0.81 mmol) are dissolved in MeOH (3 mL) and heated at about 60° C. for about 2 h after which time the reaction was concentrated under reduced pressure. The resulting oil was dissolved in DCM (3 mL) and iodobenzene diacetate (0.28 g, 0.85 mmol) was added at about ambient temperature. The reaction was allowed to stir for about 1 h upon which time the reaction was concentrated under reduced pressure and purified by silica gel chromatography using DCM/MeOH (90:10) as eluent. After concentration of the clean fractions, the resulting oil was triturated with $Et_2O$ to give a solid that was filtered and dried to provide the title compound as a light yellow solid (0.12 g, 37%): LC/MS (Table 1, Method a) $R_t$=2.32 min; MS m/z: 214.3 $(M+H)^+$.

TABLE K.1

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] and NIS, C with 2-fluoropyridine-5-boronic acid [Asymchem], D using hydrazine) using General Procedure K

| Aldehyde | Product | Example # | $R_t$ min (method) | m/z ESI+ $(M + H)^+$ |
|---|---|---|---|---|
| 2-Methylbenzaldehyde | 6-[6-(4-Fluorophenyl)-imidazo[2,1-b]oxazol-5-yl]-3-o-tolyl-[1,2,4]triazolo[4,3-a]pyridine | K.1.2 | 2.38 (a) | 410.2 |
| 4-Bromo-2-fluoro-benzaldehyde | 3-(4-Bromo-2-fluorophenyl)-6-[6-(4-fluorophenyl)-imidazo[2,1-b]oxazol-5-yl]-[1,2,4]triazolo[4,3-a]pyridine | K.1.3 | 2.60 (a) | 494.1 |
| 2-(2-Hydroxy-ethoxy)-benzaldehyde [TCI] | 2-(2-{6-[6-(4-Fluorophenyl)-imidazo[2,1-b]oxazol-5-yl]-[1,2,4]triazolo[4,3-a]pyridin-3-yl}-phenoxy)-ethanol | K.1.4 | 2.06 (a) | 456.2 |
| 2-Trifluoromethylbenzaldehyde | 6-[6-(4-Fluorophenyl)-imidazo[2,1-b]oxazol-5-yl]-3-(2-trifluoromethylphenyl)-[1,2,4]triazolo[4,3-a]pyridine | K.1.5 | 2.44 (a) | 464.1 |
| 4-Fluoro-2-trifluoromethyl-benzaldehyde [Lancaster] | 6-[6-(4-Fluorophenyl)-imidazo[2,1-b]oxazol-5-yl]-3-(4-fluoro-2-trifluoromethyl-phenyl)-[1,2,4]triazolo[4,3-a]pyridine | K.1.6 | 2.52 (a) | 482.1 |
| 2-Formylbenzoic acid methyl ester | 2-{6-[6-(4-Fluorophenyl)-imidazo[2,1-b]oxazol-5-yl]-[1,2,4]triazolo[4,3-a]pyridin-3-yl}-benzoic acid methyl ester | K.1.7 | 2.25 (a) | 454.2 |
| 2-Methoxybenzaldehyde | 6-[6-(4-Fluorophenyl)-imidazo[2,1-b]oxazol-5-yl]-3-(2-methoxyphenyl)-[1,2,4]triazolo[4,3-a]pyridine | K.1.8 | 2.31 (a) | 426.2 |
| 3-Formylbenzonitrile | 3-{6-[6-(4-Fluorophenyl)-imidazo[2,1-b]oxazol-5-yl]-[1,2,4]triazolo[4,3-a]pyridin-3-yl}-benzonitrile | K.1.9 | 2.24 (a) | 479.2 |
| 4-Formylbenzonitrile | 4-{6-[6-(4-Fluorophenyl)-imidazo[2,1-b]oxazol-5-yl]-[1,2,4]triazolo[4,3-a]pyridin-3-yl}-benzonitrile | K.1.10 | 2.27 (a) | 479.2 |
| 4-Formylbenzoic acid methyl ester | 4-{6-[6-(4-Fluorophenyl)-imidazo[2,1-b]oxazol-5-yl]-[1,2,4]triazolo[4,3-a]pyridin-3-yl}-benzoic acid methyl ester | K.1.11 | 2.34 (a) | 454.2 |
| N-(4-Formylphenyl)-acetamide | N-(4-{6-[6-(4-Fluorophenyl)-imidazo[2,1-b]oxazol-5-yl]-[1,2,4]triazolo[4,3-a]pyridin-3-yl}-phenyl)-acetamide | K.1.12 | 1.94 (a) | 451.3 |
| Benzaldehyde | 6-[6-(4-Fluorophenyl)-imidazo[2,1-b]oxazol-5-yl]-3-phenyl-[1,2,4]triazolo[4,3-a]pyridine | K.1.13 | 2.29 (a) | 454.2 |
| 3-Methyl-3H-imidazole-4-carbaldehyde [Combi Blocks] | 6-[6-(4-Fluorophenyl)-imidazo[2,1-b]oxazol-5-yl]-3-(3-methyl-3H-imidazol-4-yl)-[1,2,4]triazolo[4,3-a]pyridine | K.1.14 | 1.57 (a) | 400.1 |
| Oxo-acetic acid ethyl ester [Lancaster] | 6-[6-(4-Fluorophenyl)-imidazo[2,1-b]oxazol-5-yl]-[1,2,4]triazolo[4,3-a]pyridine-3-carboxylic acid ethyl ester | K.1.15 | 2.26 (a) | 392.2 |
| 2,6-Difluorobenzaldehyde | 3-(2,6-Difluorophenyl)-6-[6-(4-fluorophenyl)-imidazo[2,1-b]oxazol-5-yl]-[1,2,4]triazolo[4,3-a]pyridine | K.1.16 | 2.32 (a) | 432.1 |

TABLE K.1-continued

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] and NIS, C with 2-fluoropyridine-5-boronic acid [Asymchem], D using hydrazine) using General Procedure K

| Aldehyde | Product | Example # | $R_t$ min (method) | m/z ESI+ $(M + H)^+$ |
|---|---|---|---|---|
| 2,5-Difluorobenzaldehyde | 3-(2,5-Difluorophenyl)-6-[6-(4-fluorophenyl)-imidazo[2,1-b]oxazol-5-yl]-[1,2,4]triazolo[4,3-a]pyridine | K.1.17 | 2.37 (a) | 432.1 |
| 5-Bromo-2-fluorobenzaldehyde | 3-(5-Bromo-2-fluorophenyl)-6-[6-(4-fluorophenyl)-imidazo[2,1-b]oxazol-5-yl]-[1,2,4]triazolo[4,3-a]pyridine | K.1.18 | 2.56 (a) | 492.0 |
| 5-Cyano-2-fluorobenzaldehyde | 4-Fluoro-3-{6-[6-(4-fluorophenyl)-imidazo[2,1-b]oxazol-5-yl]-[1,2,4]triazolo[4,3-a]pyridin-3-yl}-benzonitrile | K.1.19 | 2.28 (a) | 439.1 |
| 3-Dimethylamino-2,2-dimethyl-propionaldehyde [Frinton] | (2-{6-[6-(4-Fluorophenyl)-imidazo[2,1-b]oxazol-5-yl]-[1,2,4]triazolo[4,3-a]pyridin-3-yl}-2-methyl-propyl)-dimethyl-amine | K.1.20 | 1.96 (a) | 419.2 |

General Procedure K.1: Hydrazone Formation Followed by Cyclization with Iodobenzene Diacetate A mixture of a substituted pyridine-2-yl-hydrazine (preferably 1 equiv), an aldehyde (1-5 equiv, preferably 1 equiv; such as isobutyraldehyde, pivaldehyde or benzaldehyde) and a suitable organic solvent (such as MeOH and/or DCM) with or preferably without about 1-5 drops (preferably 3 drops) of a suitable acid (such as HOAc, HCl, or $H_2SO_4$, preferably HOAc) are heated at about 22-60° C. (preferably about 50-60° C.) for about 0.5-24 h (preferably about 0.5-12 h). Optionally, after this time, the reaction is concentrated under reduced pressure then redissolved in a suitable organic solvent (such as DCM or MeOH). Then iodobenzene diacetate (1-3 equiv, preferably 1 equiv) is added and the reaction is allowed to stir at ambient temperature for about 0.5-8 h (preferably about 1 h). If the product precipitates during the reaction or upon cooling, it is directly filtered and dried. Alternatively, the mixture may be optionally concentrated under reduced pressure and purified by chromatography, triturated with an appropriate solvent, or crystallized from one or more solvents to yield the target compound.

Illustration of General Procedure K.1

Example #K.1.1.1 tert-Butyl 3-(6-(6-(4-fluorophenyl)imidazo[2,1-b]oxazol-5-yl)-([1,2,4]triazolo[4,3a]pyridin-3-yl)piperidine-1-carboxylate

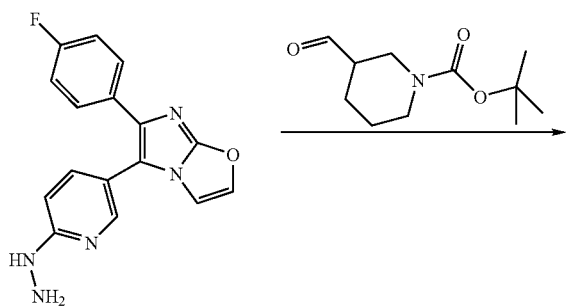

-continued

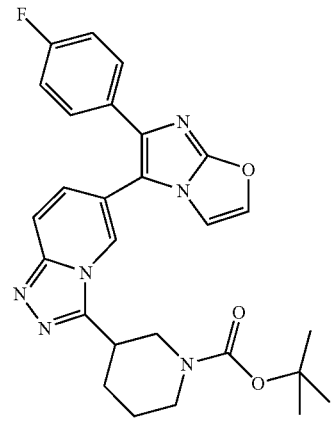

To a round bottom flask was added 6-(4-fluorophenyl)-5-(6-hydrazinylpyridin-3-yl)imidazo[2,1-b]oxazole (0.250 g, 0.808 mmol; prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine), DCM (6.0 mL) and tert-butyl 3-formylpiperidine-1-carboxylate (0.172 g, 0.808 mmol; Oakwood) followed by HOAc (0.046 mL, 0.808 mmol). The reaction mixture was stirred at ambient temperature for about 1 h. After complete formation of hydrazone, iodobenzene diacetate (0.286 g, 0.889 mmol) was added and the reaction mixture was stirred for about 2 h at ambient temperature. The reaction mixture was purified directly by flash chromatography (silica gel; DCM/MeOH gradient from 1:0 to 19:1) to give the title compound (0.374 g, 92%). LC/MS (Table 1, Method a) $R_t$=2.51 min; MS 503.3 m/z $(M+H)^+$.

TABLE K.1.1

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D using hydrazine) using General Procedure K.1

| Aldehyde | Product | Example # | R$_t$ min (method) | m/z ESI+ (M + H)+ |
|---|---|---|---|---|
| 2-Methylbutanal | 5-(3-sec-Butyl-[1,2,4]triazolo[4,3-a]pyridin-6-yl)-6-(4-fluorophenyl)imidazo[2,1-b]oxazole | K.1.1.2 | 2.26 (a) | 376.2 |
| Cyclopentanecarbaldehyde | 5-(3-Cyclopentyl-[1,2,4]triazolo[4,3-a]pyridin-6-yl)-6-(4-fluorophenyl)imidazo[2,1-b]oxazole | K.1.1.3 | 2.33 (a) | 388.1 |
| 1-Methylcyclobutanecarbaldehyde (prepared according to WO 2006064286A1 Example 5) | 6-(4-Fluorophenyl)-5-(3-(1-methylcyclobutyl)-[1,2,4]triazolo[4,3-a]pyridin-6-yl)imidazo[2,1-b]oxazole | K.1.1.4 | 2.30 (a) | 388.1 |
| 3,3,3-Trifluoropropanal [Matrix] | 6-(4-Fluorophenyl)-5-(3-(2,2,2-trifluoroethyl)-[1,2,4]triazolo[4,3-a]pyridin-6-yl)imidazo[2,1-b]oxazole | K.1.1.5 | 2.20 (a) | 402.1 |
| tert-Butyl 4-formylpiperidine-1-carboxylate [CHN Technologies] | tert-Butyl 4-(6-(6-(4-fluorophenyl)imidazo[2,1-b]oxazol-5-yl)-[1,2,4]triazolo[4,3-a]pyridin-3-yl)piperidine-1-carboxylate | K.1.1.6 | 2.43 (a) | 503.2 |
| 2-Methyl-5-oxopentan-2-yl acetate [ABChem] | 4-(6-(6-(4-Fluorophenyl)imidazo[2,1-b]oxazol-5-yl)-[1,2,4]triazolo[4,3-a]pyridin-3-yl)-2-methylbutan-2-yl acetate | K.1.1.7 | 1.58 (a) | 403.2 |
| 3,3,3-Trifluoro-2-methylpropanal [Ryan Scientific] | 6-(4-Fluorophenyl)-5-(3-(1,1,1-trifluoropropan-2-yl)-[1,2,4]triazolo[4,3-a]pyridin-6-yl)imidazo[2,1-b]oxazole | K.1.1.8 | 2.24 (a) | 448.2 |
| 3-Hydroxy-3-methylbutanal [Prepared according to Yachi et. al., J. Am. Chem. Soc., 1999, 121, 9465, Entry #14] | 1-(6-(6-(4-Fluorophenyl)imidazo[2,1-b]oxazol-5-yl)-[1,2,4]triazolo[4,3-a]pyridin-3-yl)-2-methylpropan-2-ol | K.1.1.9 | 1.63 (d) | 392.1 |
| 3-Methyl-3-morpholinobutanal [ChemBridge] | 6-(4-Fluorophenyl)-5-(3-(2-methyl-2-morpholinopropyl)-[1,2,4]triazolo[4,3-a]pyridin-6-yl)imidazo[2,1-b]oxazole | K.1.1.10 | 2.02 (a) | 461.2 |
| tert-Butyl 4-(2-oxoethyl)piperidine-1-carboxylate [PharmaCore] | tert-Butyl 4-((6-(6-(4-fluorophenyl)imidazo[2,1-b]oxazol-5-yl)-[1,2,4]triazolo[4,3-a]pyridin-3-yl)methyl)piperidine-1-carboxylate | K.1.1.11 | 2.47 (a) | 517.2 |
| 3-Hydroxy-2,2-dimethylpropanal [prepared according to Upadhya et. al., Tetrahedron: Asymmetry, 1999, 10, 2899, Compound #3] | 2-(6-(6-(4-Fluorophenyl)imidazo[2,1-b]oxazol-5-yl)-[1,2,4]triazolo[4,3-a]pyridin-3-yl)-2-methylpropan-1-ol | K.1.1.12 | 1.92 (a) | 392.2 |
| 4-Methyl-1H-imidazole-5-carbaldehyde | 6-(4-Fluorophenyl)-5-(3-(4-methyl-1H-imidazol-5-yl)-[1,2,4]triazolo[4,3-a]pyridine-6-yl)imidazo[2,1-b]oxazole | K.1.1.13 | 1.91 (a) | 400.2 |
| tert-Butyl-3-formylazetidine-1-carboxylate [Betapharma] | tert-Butyl-3-(6-(6-(4-fluorophenyl)imidazo[2,1-b]oxazole-5-yl)-[1,2,4]triazolo[4,3-a]pyridine-3-yl)azetidine-1-carboxylate | K.1.1.14 | 2.33 (a) | 475.2 |
| 2-Fluoro-5-methoxybenzaldehyde | 5-(3-(2-Fluoro-5-methoxyphenyl-[1,2,4]-triazolo[4,3-a]pyridine-6-yl)-6-(4-fluorophenyl)imidazo[2,1-b]oxazole | K.1.1.15 | 2.41 (a) | 444.1 |

TABLE K.1.1-continued

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D using hydrazine) using General Procedure K.1

| Aldehyde | Product | Example # | $R_t$ min (method) | m/z ESI+ $(M + H)^+$ |
|---|---|---|---|---|
| 2,4,6-Trifluorobenzaldehyde [Oakwood] | 6-(4-Fluorophenyl)-5-(3-(2,4,6-trifluorophenyl)-[1,2,4]triazolo[4,3-a]pyridin-6-yl)imidazo[2,1-b]oxazole | K.1.1.16 | 2.40 (a) | 450.1 |
| (1R,2R)-Ethyl-2-formylcyclopropanecarboxylate | (1R,2R)-Ethyl-2-(6-(6-(4-fluorophenyl)imidazo[2,1-b]oxazol-5-yl)-[1,2,4]-triazolo[4,3-a]pyridin-3-yl)cyclopropanecarboxylate | K.1.1.17 | 2.25 (a) | 432.2 |
| Propionaldehyde | 5-(3-Ethyl-[1,2,4]triazolo[4,3-a]pyridin-6-yl)-6-(4-fluorophenyl)imidazo[2,1-b]oxazole | K.1.1.18 | 2.01 (a) | 348.1 |
| tert-Butyl 3-formylpyrrolidine-1-carboxylate [Tyger] | tert-Butyl 3-(6-(6-(4-fluorophenyl)imidazo[2,1-b]oxazol-5-yl)-[1,2,4]triazolo[4,3-a]pyridin-3-yl)pyrrolidine-1-carboxylate | K.1.1.19 | 2.40 (a) | 489.2 |
| 2-Ethylbutanal | 6-(4-Fluorophenyl)-5-(3-(pentan-3-yl)-[1,2,4]triazolo[4,3-a]pyridin-6-yl)imidazo[2,1-b]oxazole | K.1.1.20 | 2.35 (a) | 390.2 |
| 1-((Dimethylamino)methyl)cyclopentanecarbaldehyde [Alfa Aesar] | 1-(1-(6-(6-(4-Fluorophenyl)imidazo[2,1-b]oxazol-5-yl)-[1,2,4]triazolo[4,3-a]pyridin-3-yl)cyclopentyl)-N,N-dimethylmethanamine | K.1.1.21 | 1.73 (a) | 445.2 |
| 2,2-Dimethylbutanal [Wiley] | 6-(4-Fluorophenyl)-5-(3-tert-pentyl-[1,2,4]triazolo[4,3-a]pyridin-6-yl)imidazo[2,1-b]oxazole | K.1.1.22 | 2.34 (a) | 390.2 |
| Tetrahydrofuran-3-carbaldehyde | 6-(4-Fluorophenyl)-5-(3-(tetrahydrofuran-3-yl)-[1,2,4]triazolo[4,3-a]pyridin-6-yl)imidazo[2,1-b]oxazole | K.1.1.23 | 1.93 (a) | 390.2 |
| 3,6-Dihydro-2H-pyran-4-carbaldehyde [prepared according to Spreitzer et al., Monatshefte fur chemie, 1990, 121, 963-970] | 5-(3-(3,6-Dihydro-2H-pyran-4-yl)-[1,2,4]triazolo[4,3-a]pyridin-6-yl)-6-(4-fluorophenyl)imidazo[2,1-b]oxazole | K.1.1.24 | 2.04 (a) | 460.2 |
| Tetrahydro-2H-pyran-3-carbaldehyde [J&W Pharmlab] | 6-(4-Fluorophenyl)-5-(3-(tetrahydro-2H-pyran-3-yl)-[1,2,4]triazolo[4,3-a]pyridin-6-yl)imidazo[2,1-b]oxazole | K.1.1.25 | 2.05 (a) | 404.2 |
| Tetrahydro-2H-pyran-4-carbaldehyde [J&W Pharmlab] | 6-(4-Fluorophenyl)-5-(3-(tetrahydro-2H-pyran-4-yl)-[1,2,4]triazolo[4,3-a]pyridin-6-yl)imidazo[2,1-b]oxazole | K.1.1.26 | 1.94 (a) | 404.2 |
| Cyclohex-3-enecarbaldehyde | 5-(3-(Cyclohex-3-enyl)-[1,2,4]triazolo[4,3-a]pyridin-6-yl)-6-(4-fluorophenyl)imidazo[2,1-b]oxazole | K.1.1.27 | 2.34 (a) | 400.2 |
| 2-Fluoro-4-methoxybenzaldehyde | 5-(3-(2-Fluoro-4-methoxyphenyl)-[1,2,4]triazolo[4,3-a]pyridin-6-yl)-6-(4-fluorophenyl)imidazo[2,1-b]oxazole | K.1.1.28 | 2.37 (a) | 458.2 |
| 2-Fluoro-4-hydroxybenzaldehyde [Betapharma] | 3-Fluoro-4-(6-(6-(4-fluorophenyl)imidazo[2,1-b]oxazol-5-yl)-[1,2,4]triazolo[4,3-a]pyridin-3-yl)phenol | K.1.1.29 | 2.08 (a) | 430.1 |
| 2,3-Dihydroxypropanal | 1-(6-(6-(4-Fluorophenyl)imidazo[2,1-b]oxazol-5-yl)-[1,2,4]triazolo[4,3-a]pyridin-3-yl)ethane-1,2-diol | K.1.1.30 | 1.68 (a) | 380.1 |

TABLE K.1.1-continued

Examples prepared from {5-[6-(4-fluorophenyl)-imidazo[2,1-b]oxazol-5-yl]-pyridin-2-yl}-hydrazine (prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D using hydrazine) using General Procedure K.1

| Aldehyde | Product | Example # | $R_t$ min (method) | m/z ESI+ $(M + H)^+$ |
|---|---|---|---|---|
| Cyclohexanecarbaldehyde | 5-(3-Cyclohexyl-[1,2,4]triazolo[4,3-a]pyridin-6-yl)-6-(4-fluorophenyl)imidazo[2,1-b]oxazole | K.1.1.31 | 2.44 (a) | 402.2 |
| Acetaldehyde | 6-(4-Fluorophenyl)-5-(3-methyl-[1,2,4]triazolo[4,3-a]pyridin-6-yl)imidazo[2,1-b]oxazole | K.1.1.32 | 1.67 (a) | 334.1 |
| 2,2-Dimethyltetrahydro-2H-pyran-4-carbaldehyde | 5-(3-(2,2-Dimethyltetrahydro-2H-pyran-4-yl)-[1,2,4]triazolo[4,3-a]pyridin-6-yl)-6-(4-fluorophenyl)imidazo[2,1-b]oxazole | K.1.1.33 | 2.08 (a) | 434.2 |
| tert-Butyl (cis)-4-formylcyclohexylcarbamate [Albany Molecular Research Incorporated] | tert-Butyl (cis)-4-(6-(6-(4-fluorophenyl)imidazo[2,1-b]oxazol-5-yl)-[1,2,4]triazolo[4,3-a]pyridin-3-yl)cyclohexylcarbamate | K.1.1.34 | 2.46 (a) | 517.3 |
| tert-Butyl (trans)-4-formylcyclohexylcarbamate | tert-Butyl (trans)-4-(6-(6-(4-fluorophenyl)imidazo[2,1-b]oxazol-5-yl)-[1,2,4]triazolo[4,3-a]pyridin-3-yl)cyclohexylcarbamate | K.1.1.35 | 2.42 (a) | 517.3 |

TABLE K.1.2

Examples prepared from {5-[6-(2,4-Difluorophenyl)-imidazo[2,1-b]oxazol-5-yl]-pyridin-2-yl}-hydrazine (Example #2, step B) using General Procedure K.1

| Aldehyde | Product | Example # | $R_t$ min (method) | m/z ESI+ $(M + H)^+$ |
|---|---|---|---|---|
| Propionaldehyde [Fluka] | 6-(2,4-Difluorophenyl)-5-(3-ethyl-[1,2,4]triazolo[4,3-a]pyridin-6-yl)imidazo[2,1-b]oxazole | K.1.2.1 | 1.97 (a) | 366.1 |
| 2-Methylbutanal | 5-(3-sec-Butyl-[1,2,4]triazolo[4,3-a]pyridin-6-yl)-6-(2,4-difluorophenyl)imidazo[2,1-b]oxazole | K.1.2.2 | 2.18 (a) | 394.2 |
| 1-Methylcyclobutanecarbaldehyde (prepared according to WO 2006064286A1 Example 5) | 6-(2,4-Difluorophenyl)-5-(3-(1-methylcyclobutyl)-[1,2,4]triazolo[4,3-a]pyridin-6-yl)imidazo[2,1-b]oxazole | K.1.2.3 | 2.26 (a) | 406.1 |
| 3-Hydroxy-3-methylbutanal [Prepared according to Yachi et. al., J. Am. Chem. Soc., 1999, 121, 9465, Entry 14] | 1-(6-(6-(2,4-Difluorophenyl)imidazo[2,1-b]oxazol-5-yl)-[1,2,4]triazolo[4,3-a]pyridin-3-yl)-2-methylpropan-2-ol | K.1.2.4 | 1.87 (a) | 410.1 |
| 4-Methyl-1H-imidazole-5-carbaldehyde | 6-(2,4-Difluorophenyl)-5-(3-(4-methyl-1H-imidazol-5-yl)-[1,2,4]triazolo[4,3-a]pyridin-6-yl)imidazo[2,1-b]oxazole | K.1.2.5 | 1.88 (a) | 418.2 |
| 2-Ethylbutanal | 6-(2,4-Difluorophenyl)-5-(3-(pentan-3-yl)-[1,2,4]triazolo[4,3-a]pyridin-6-yl)imidazo[2,1-b]oxazole | K.1.2.6 | 2.30 (a) | 408.2 |
| Cyclopropanecarbaldehyde | 5-(3-Cyclopropyl-[1,2,4]triazolo[4,3-a]pyridin-6-yl)-6-(2,4-difluorophenyl)imidazo[2,1-b]oxazole | K.1.2.7 | 2.01 (a) | 378.2 |

TABLE K.1.2-continued

Examples prepared from {5-[6-(2,4-Difluorophenyl)-imidazo[2,1-b]oxazol-5-yl]-pyridin-2-yl}-hydrazine (Example #2, step B) using General Procedure K.1

| Aldehyde | Product | Example # | $R_t$ min (method) | m/z ESI+ $(M + H)^+$ |
|---|---|---|---|---|
| Cyclohexanecarbaldehyde | 5-(3-Cyclohexyl-[1,2,4]triazolo[4,3-a]pyridin-6-yl)-6-(2,4-difluorophenyl)imidazo[2,1-b]oxazole | K.1.2.8 | 2.38 (a) | 420.2 |
| 3-Methyloxetane-3-carbaldehyde (Preparation #3) | 6-(2,4-Difluorophenyl)-5-(3-(3-methyloxetan-3-yl)-[1,2,4]triazolo[4,3-a]pyridin-6-yl)imidazo[2,1-b]oxazole | K.1.2.9 | 1.91 (a) | 408.2 |
| Cyclobutanecarbaldehyde | 5-(3-Cyclobutyl-[1,2,4]triazolo[4,3-a]pyridin-6-yl)-6-(2,4-difluorophenyl)imidazo[2,1-b]oxazole | K.1.2.10 | 2.14 (a) | 392.2 |
| 3,3-Dimethylbutanal | 6-(2,4-Difluorophenyl)-5-(3-neopentyl-[1,2,4]triazolo[4,3-a]pyridin-6-yl)imidazo[2,1-b]oxazole | K.1.2.11 | 2.30 (a) | 408.2 |
| 3-Methylbutanal | 6-(2,4-Difluorophenyl)-5-(3-isobutyl-[1,2,4]triazolo[4,3-a]pyridin-6-yl)imidazo[2,1-b]oxazole | K.1.2.12 | 2.20 (a) | 394.2 |
| Pivalaldehyde | 5-(3-tert-Butyl-[1,2,4]triazolo[4,3-a]pyridin-6-yl)-6-(2,4-difluorophenyl)imidazo[2,1-b]oxazole | K.1.2.13 | 2.19 (a) | 394.2 |
| Tetrahydro-2H-pyran-4-carbaldehyde [J&W Pharmlab] | 6-(2,4-Difluorophenyl)-5-(3-(tetrahydro-2H-pyran-4-yl)-[1,2,4]triazolo[4,3-a]pyridin-6-yl)imidazo[2,1-b]oxazole | K.1.2.14 | 1.89 (a) | 422.1 |

TABLE K.1.3

Examples prepared from {5-[6-(2,4,5-trifluorophenyl)-imidazo[2,1-b]oxazol-5-yl]-pyridin-2-yl}-hydrazine (prepared using A from Preparation #O.1 with NIS, C with 2-fluoropyridine-5-boronic acid [Asymchem], D with hydrazine) using General Procedure K.1

| Aldehyde | Product | Example # | $R_t$ min (method) | m/z ESI+ $(M + H)^+$ |
|---|---|---|---|---|
| Cyclopropanecarbaldehyde | 5-(3-Cyclopropyl-[1,2,4]triazolo[4,3-a]pyridin-6-yl)-6-(2,4,5-trifluorophenyl)imidazo[2,1-b]oxazole | K.1.3.1 | 2.13 (a) | 396.1 |
| Pivalaldehyde | 5-(3-tert-Butyl-[1,2,4]triazolo[4,3-a]pyridin-6-yl)-6-(2,4,5-trifluorophenyl)imidazo[2,1-b]oxazole | K.1.3.2 | 2.29 (a) | 412.2 |
| Propionaldehyde [Fluka] | 5-(3-Ethyl-[1,2,4]triazolo[4,3-a]pyridin-6-yl)-6-(2,4,5-trifluorophenyl)imidazo[2,1-b]oxazole | K.1.3.3 | 2.07 (a) | 384.1 |
| Isobutyraldehyde | 5-(3-Isopropyl-[1,2,4]triazolo[4,3-a]pyridine-6-yl)-6-(2,4,5-trifluorophenyl)imidazo[2,1-b]oxazole | K.1.3.4 | 2.17 (a) | 398.2 |
| 3,3-Dimethylbutanal | 5-(3-Neopentyl-[1,2,4]triazolo[4,3-a]pyridin-6-yl)-6-(2,4,5-trifluorophenyl)imidazo[2,1-b]oxazole | K.1.3.5 | 2.40 (a) | 426.2 |
| 3-Methylbutanal | 5-(3-Isobutyl-[1,2,4]triazolo[4,3-a]pyridin-6-yl)-6-(2,4,5-trifluorophenyl)imidazo[2,1-b]oxazole | K.1.3.6 | 2.29 (a) | 412.2 |

TABLE K.1.4

Examples prepared from {5-[6-(2-chloro-4-fluorophenyl)-imidazo[2,1-b]oxazol-5-yl]-pyridin-2-yl}-hydrazine (prepared using N from 2'-chloro-4'-fluoroacetophenone [Lancaster], O with oxazole-2-amine [GL Synthesis], A with NIS, C with 2-fluoropyridine-5-boronic acid [Asymchem], D with hydrazine) using General Procedure K.1

| Aldehyde | Product | Example # | $R_t$ min (method) | m/z ESI+ (M + H)+ |
|---|---|---|---|---|
| 2-Methylbutanal | 5-(3-sec-Butyl-[1,2,4]triazolo[4,3-a]pyridin-6-yl)-6-(2-chloro-4-fluorophenyl)imidazo[2,1-b]oxazole | K.1.4.1 | 2.26 (a) | 410.1 |
| 3-Methylbutanal | 6-(2-Chloro-4-fluorophenyl)-5-(3-isobutyl-[1,2,4]triazolo[4,3-a]pyridin-6-yl)imidazo[2,1-b]oxazole | K.1.4.2 | 2.26 (a) | 410.1 |
| Cyclopropanecarbaldehyde | 6-(2-Chloro-4-fluorophenyl)-5-(3-cyclopropyl-[1,2,4]triazolo[4,3-a]pyridin-6-yl)imidazo[2,1-b]oxazole | K.1.4.3 | 2.08 (a) | 394.1 |
| 2-Ethylbutanal | 6-(2-Chloro-4-fluorophenyl)-5-(3-(pentan-3-yl)-[1,2,4]triazolo[4,3-a]pyridin-6-yl)imidazo[2,1-b]oxazole | K.1.4.4 | 3.04 (a) | 424.4 |
| Isobutyraldehyde | 6-(2-Chloro-4-fluorophenyl)-5-(3-isopropyl-[1,2,4]triazolo[4,3-a]pyridin-6-yl)imidazo[2,1-b]oxazole | K.1.4.5 | 2.14 (a) | 396.1 |
| 1-Methylcyclobutanecarbaldehyde (prepared according to WO 2006064286A1 Example 5) | 6-(2-Chloro-4-fluorophenyl)-5-(3-(1-methylcyclobutyl)-[1,2,4]triazolo[4,3-a]pyridin-6-yl)imidazo[2,1-b]oxazole | K.1.4.6 | 2.14 (a) | 422.1 |
| Pivalaldehyde | 5-(3-tert-Butyl-[1,2,4]triazolo[4,3-a]pyridin-6-yl)-6-(2-chloro-4-fluorophenyl)imidazo[2,1-b]oxazole | K.1.4.7 | 2.27 (a) | 410.1 |

TABLE K.1.5

Examples prepared from {5-[6-(4-chloro-2-fluorophenyl)-imidazo[2,1-b]oxazol-5-yl]-pyridin-2-yl}-hydrazine (prepared using N from 4'-chloro-2'-fluoroacetophenone [Oakwood], O with oxazole-2-amine [GL Synthesis], A with NIS, C with 2-fluoropyridine-5-boronic acid [Asymchem], D with hydrazine) using General Procedure K.1

| Aldehyde | Product | Example # | $R_t$ min (method) | m/z ESI+ (M + H)+ |
|---|---|---|---|---|
| 3-Methylbutanal | 6-(4-Chloro-2-fluorophenyl)-5-(3-isobutyl-[1,2,4]triazolo[4,3-a]pyridin-6-yl)imidazo[2,1-b]oxazole | K.1.5.1 | 2.38 (a) | 410.1 |
| 2-Ethylbutanal | 6-(4-Chloro-2-fluorophenyl)-5-(3-(pentan-3-yl)-[1,2,4]triazolo[4,3-a]pyridin-6-yl)imidazo[2,1-b]oxazole | K.1.5.2 | 3.24 (a) | 424.7 |
| Isobutyraldehyde | 6-(4-Chloro-2-fluorophenyl)-5-(3-isopropyl-[1,2,4]triazolo[4,3-a]pyridin-6-yl)imidazo[2,1-b]oxazole | K.1.5.3 | 2.23 (a) | 396.1 |
| Pivalaldehyde | 5-(3-tert-Butyl-[1,2,4]triazolo[4,3-a]pyridin-6-yl)-6-(4-chloro-2-fluorophenyl)imidazo[2,1-b]oxazole | K.1.5.4 | 2.37 (a) | 410.1 |

TABLE K.1.6

Examples prepared from {5-[6-(3,4-difluorophenyl)-imidazo[2,1-b]oxazol-5-yl]-pyridin-2-yl}-hydrazine (prepared using N from 3',4'-difluoroacetophenone, O with oxazole-2-amine [GL Synthesis], A with NIS, C with 2-fluoropyridine-5-boronic acid [Asymchem], D with hydrazine) using General Procedure K.1

| Aldehyde | Product | Example # | $R_t$ min (method) | m/z ESI+ (M + H)+ |
|---|---|---|---|---|
| Isobutyraldehyde | 6-(3,4-Difluorophenyl)-5-(3-isopropyl-[1,2,4]triazolo[4,3-a]pyridin-6-yl)imidazo[2,1-b]oxazole | K.1.6.1 | 2.23 (a) | 380.2 |
| 3-Methylbutanal | 6-(3,4-Difluorophenyl)-5-(3-isobutyl-[1,2,4]triazolo[4,3-a]pyridin-6-yl)imidazo[2,1-b]oxazole | K.1.6.2 | 2.36 (a) | 394.2 |

TABLE K.1.7

Example prepared from 6-(2,4-dichlorophenyl)-5-(6-hydrazinylpyridin-3-yl)imidazo[2,1-b]oxazole (prepared using O from 2-bromo-2',4'-dichloroacetophenone and oxazole-2-amine [GL Synthesis], A with NIS, C with 2-fluoropyridine-5-boronic acid [Asymchem], D with hydrazine) using General Procedure K.1

| Aldehyde | Product | Example # | $R_t$ min (method) | m/z ESI+ (M + H)+ |
|---|---|---|---|---|
| 2-Ethylbutanal | 6-(2,4-Dichlorophenyl)-5-(3-(pentan-3-yl)-[1,2,4]triazolo[4,3-a]pyridin-6-yl)imidazo[2,1-b]oxazole | K.1.7.1 | 3.32 (a) | 440.8 |
| Isobutyraldehyde | 6-(2,4-Dichlorophenyl)-5-(3-isopropyl-[1,2,4]triazolo[4,3-a]pyridin-6-yl)imidazo[2,1-b]oxazole | K.1.7.2 | 2.30 (a) | 412.1 |
| 3-Methylbutanal | 6-(2,4-Dichlorophenyl)-5-(3-isobutyl-[1,2,4]triazolo[4,3-a]pyridin-6-yl)imidazo[2,1-b]oxazole | K.1.7.3 | 2.44 (a) | 426.1 |

TABLE K.1.8

Examples prepared from {5-[6-(3-trifluoromethylphenyl)-imidazo[2,1-b]oxazol-5-yl]-pyridin-2-yl}-hydrazine (prepared using N from 3'-(trifluoromethyl)acetophenone, O with oxazole-2-amine [GL Synthesis], A with NIS, C with 2-fluoropyridine-5-boronic acid [Asymchem], D with hydrazine) using General Procedure K.1

| Aldehyde | Product | Example # | $R_t$ min (method) | m/z ESI+ (M + H)+ |
|---|---|---|---|---|
| Isobutyraldehyde | 5-(3-Isopropyl-[1,2,4]triazolo[4,3-a]pyridin-6-yl)-6-(3-(trifluoromethyl)phenyl)imidazo[2,1-b]oxazole | K.1.8.1 | 2.39 (a) | 412.1 |
| Pivalaldehyde | 5-(3-tert-Butyl-[1,2,4]triazolo[4,3-a]pyridin-6-yl)-6-(3-(trifluoromethyl)phenyl)imidazo[2,1-b]oxazole | K.1.8.2 | 2.52 (a) | 426.2 |

TABLE K.1.9

Examples prepared from 6-(4-fluoro-2-(trifluoromethyl)phenyl)-5-(6-hydrazinylpyridin-3-yl)imidazo[2,1-b]oxazole (prepared using N from 4'-fluoro-2'-(trifluoromethyl)acetophenone [Alfa Aesar], O with oxazole-2-amine [GL Synthesis], A with NIS, C with 2-fluoropyridine-5-boronic acid [Asymchem], D with hydrazine) using General Procedure K.1

| Aldehyde | Product | Example # | $R_t$ min (method) | m/z ESI+ $(M + H)^+$ |
|---|---|---|---|---|
| 3-Methylbutanal | 6-(4-Fluoro-2-(trifluoromethyl)phenyl)-5-(3-isobutyl-[1,2,4]triazolo[4,3-a]pyridin-6-yl)imidazo[2,1-b]oxazole | K.1.9.1 | 2.33 (a) | 444.1 |
| Isobutyraldehyde | 6-(4-Fluoro-2-(trifluoromethyl)phenyl)-5-(3-isopropyl-[1,2,4]triazolo[4,3-a]pyridin-6-yl)imidazo[2,1-b]oxazole | K.1.9.2 | 2.22 (a) | 430.1 |

TABLE K.1.10

Examples prepared 6-(2,4-difluorophenyl)-5-(6-hydrazinylpyridin-3-yl)imidazo[2,1-b]thiazole (prepared using C from Preparation #1 with 2-fluoropyridine-5-boronic acid [Asymchem], D with hydrazine) using General Procedure K.1

| Aldehyde | Product | Example # | $R_t$ min (method) | m/z ESI+ $(M + H)^+$ |
|---|---|---|---|---|
| Isobutyraldehyde | 6-(2,4-Difluorophenyl)-5-(3-isopropyl-[1,2,4]triazolo[4,3-a]pyridin-6-yl)imidazo[2,1-b]thiazole | K.1.10.1 | 2.14 (a) | 396.1 |
| 3-Methylbutanal | 6-(2,4-Difluorophenyl)-5-(3-isobutyl-[1,2,4]triazolo[4,3-a]pyridin-6-yl)imidazo[2,1-b]thiazole | K.1.10.2 | 2.28 (a) | 410.1 |

TABLE K.1.11

Examples prepared from 6-(2,4-difluorophenyl)-5-(6-hydrazinylpyridin-3-yl)-2-methylimidazo[2,1-b]oxazole (prepared using O from 2-bromo-2',4'-difluoroacetophenone with from Preparation #2, A with NIS, C with 2-fluoropyridine-5-boronic acid [Asymchem], D with hydrazine) using General Procedure K.1

| Aldehyde | Product | Example # | $R_t$ min (method) | m/z ESI+ $(M + H)^+$ |
|---|---|---|---|---|
| Isobutyraldehyde | 6-(2,4-Difluorophenyl)-5-(3-isopropyl-[1,2,4]triazolo[4,3-a]pyridin-6-yl)-2-methylimidazo[2,1-b]oxazole | K.1.11.1 | 2.21 (a) | 394.1 |
| 3-Methylbutanal | 6-(2,4-Difluorophenyl)-5-(3-isobutyl-[1,2,4]triazolo[4,3-a]pyridin-6-yl)-2-methylimidazo[2,1-b]oxazole | K.1.11.2 | 2.35 (a) | 408.1 |

TABLE K.1.12

Examples prepared from {5-[6-(3,4,5-trifluorophenyl)-imidazo[2,1-b]oxazol-5-yl]-pyridin-2-yl}-hydrazine (prepared using N from 3',4',5'-trifluoroacetophenone [Oakwood], O with oxazole-2-amine [GL Synthesis], A with NIS, C with 2-fluoropyridine-5-boronic acid [Asymchem], D with hydrazine) using General Procedure K.1

| Aldehyde | Product | Example # | $R_t$ min (method) | m/z ESI+ $(M + H)^+$ |
|---|---|---|---|---|
| Isobutyraldehyde | 5-(3-Isopropyl-[1,2,4]triazolo[4,3-a]pyridin-6-yl)-6-(3,4,5-trifluorophenyl)imidazo[2,1-b]oxazole | K.1.12.1 | 2.36 (a) | 398.1 |

TABLE K.1.12-continued

Examples prepared from {5-[6-(3,4,5-trifluorophenyl)-imidazo[2,1-b]oxazol-5-yl]-pyridin-2-yl}-hydrazine (prepared using N from 3',4',5'-trifluoroacetophenone [Oakwood], O with oxazole-2-amine [GL Synthesis], A with NIS, C with 2-fluoropyridine-5-boronic acid [Asymchem], D with hydrazine) using General Procedure K.1

| Aldehyde | Product | Example # | R$_t$ min (method) | m/z ESI+ (M + H)$^+$ |
|---|---|---|---|---|
| 3-Methylbutanal | 5-(3-Isobutyl-[1,2,4]triazolo[4,3-a]pyridin-6-yl)-6-(3,4,5-trifluorophenyl)imidazo[2,1-b]oxazole | K.1.12.2 | 2.49 (a) | 412.1 |

TABLE K.1.13

Examples prepared from {5-[6-(4-chlorophenyl)-imidazo[2,1-b]oxazol-5-yl]-pyridin-2-yl}-hydrazine (prepared using O from 2-bromo-4'-chloroacetophenone using with oxazole-2-amine [GL Synthesis], A with NIS, C with 2-fluoropyridine-5-boronic acid [Asymchem], D with hydrazine) using General Procedure K.1

| Aldehyde | Product | Example # | R$_t$ min (method) | m/z ESI+ (M + H)$^+$ |
|---|---|---|---|---|
| Isobutyraldehyde | 6-(4-Chlorophenyl)-5-(3-isopropyl-[1,2,4]triazolo[4,3-a]pyridin-6-yl)imidazo[2,1-b]oxazole | K.1.13.1 | 2.32 (a) | 378.1 |
| 3-Methylbutanal | 6-(4-Chlorophenyl)-5-(3-isobutyl-[1,2,4]triazolo[4,3-a]pyridin-6-yl)imidazo[2,1-b]oxazole | K.1.13.2 | 2.45 (a) | 392.2 |
| 2-Ethylbutanal | 6-(4-Chlorophenyl)-5-(3-(pentan-3-yl)-[1,2,4]triazolo[4,3-a]pyridin-6-yl)imidazo[2,1-b]oxazole | K.1.13.3 | 2.57 (a) | 406.2 |

TABLE K.1.14

Examples prepared from isobutyraldehyde using General Procedure K

| Hydrazine | Product | Example # | R$_t$ min (method) | m/z ESI+ (M + H)$^+$ |
|---|---|---|---|---|
| 6-(2,4-Difluorophenyl)-5-(6-hydrazinylpyridin-3-yl)-N,N-dimethylimidazo[2,1-b]oxazole-2-carboxamide (prepared using P from Preparation #4 with dimethylamine, D using hydrazine) | 6-(2,4-Difluorophenyl)-5-(3-isopropyl-[1,2,4]triazolo[4,3-a]pyridin-6-yl)-N,N-dimethylimidazo[2,1-b]oxazole-2-carboxamide | K.1.14.1 | 1.99 (a) | 451.2 |
| 6-(2,4-Difluorophenyl)-5-(6-hydrazinylpyridin-3-yl)-N-(2-hydroxyethyl)imidazo[2,1-b]oxazole-2-carboxamide (prepared using P from Preparation #4 with 2-aminoethanol, D using hydrazine) | 6-(2,4-Difluorophenyl)-N-(2-hydroxyethyl)-5-(3-isopropyl-[1,2,4]triazolo[4,3-a]pyridin-6-yl)imidazo[2,1-b]oxazole-2-carboxamide | K.1.14.2 | 1.77 (a) | 467.2 |
| 6-(2,4-Difluorophenyl)-N-(3-(dimethylamino)propyl)-5-(6-hydrazinylpyridin-3-yl)imidazo[2,1-b]oxazole-2-carboxamide (prepared using P from Preparation #4 with N1,N1-dimethylpropane-1,3-diamine), D using hydrazine | 6-(2,4-Difluorophenyl)-N-(3-(dimethylamino)propyl)-5-(3-isopropyl-[1,2,4]triazolo[4,3-a]pyridin-6-yl)imidazo[2,1-b]oxazole-2-carboxamide | K.1.14.3 | 1.62 (a) | 508.2 |

TABLE K.1.14-continued

Examples prepared from isobutyraldehyde using General Procedure K

| Hydrazine | Product | Example # | R$_t$ min (method) | m/z ESI+ (M + H)+ |
|---|---|---|---|---|
| 5-[6-(2,4-difluorophenyl)-imidazo[2,1-b]oxazol-5-yl]-pyridin-2-yl}-hydrazine (prepared using C from Example #2, step A with 6-fluoro-2-methylpyridin-3-ylboronic acid [Asymchem], D with hydrazine) | 6-(2,4-Difluorophenyl)-5-(3-isopropyl-5-methyl-[1,2,4]triazolo[4,3-a]pyridin-6-yl)imidazo[2,1-b]oxazole | K.1.14.4 | 2.84 (a) | 394.3 |

TABLE K.1.15

Examples prepared from {5-[6-(4-fluorophenyl)-imidazo[2,1-b]thiazol-5-yl]-pyridin-2-yl}-hydrazine (prepared using A from 6-(4-fluorophenyl)-imidazo[2,1-b]thiazole [prepared according to WO2004110990A2, Example 2, Steps 1] with NIS, C with 2-fluoropyridine-5-boronic acid [Asymchem], D with hydrazine) using General Procedure K.1

| Aldehyde | Product | Example # | R$_t$ min (method) | m/z ESI+ (M + H)+ |
|---|---|---|---|---|
| Isobutyraldehyde | 6-[6-(4-Fluorophenyl)imidazo[2,1-b]thiazol-5-yl]-3-isopropyl-[1,2,4]triazolo[4,3-a]pyridine | K.1.15.1 | 2.21 (a) | 378.1 |
| Isovaleraldehyde | 6-[6-(4-Fluorophenyl)imidazo[2,1-b]thiazol-5-yl]-3-isobutyl-[1,2,4]triazolo[4,3-a]pyridine | K.1.15.2 | 2.35 (a) | 392.2 |

General Procedure L: Carbonylation of an Aromatic Halide

A round bottom flask is charged with an aryl halide (aryl bromide or iodide, preferably an iodide) (preferably 1 equiv) and a suitable catalyst [for example, dichlorobis(triphenylphosphine)palladium (II) or tetrakis(triphenylphosphine) palladium (0), preferably dichlorobis(triphenylphosphine)palladium (II)] (about 0.01-20 mol %, preferably 10 mol %). The reaction flask is filled and evacuated with nitrogen gas about 1-5 times (preferably 4 times), followed by the addition of an appropriate organic solvent (such as DMF, NMP, or ethylene glycol dimethyl ether, preferably DMF), an organic base (for example, TEA, N-methylmorpholine, pyridine, or DIEA, preferably TEA) (about 1-10 equiv, preferably 3 equiv) and the appropriate nucleophilic substrate (about 1-10 equiv, preferably 5.0 equiv). The flask is then filled and evacuated with carbon monoxide about 1-5 times (preferably 3 times) and the reaction mixture is heated at about 60-100° C. (preferably 80° C.) under an atmosphere of carbon monoxide for about 0.5-24 h (preferably 2 h). The reaction mixture is cooled to ambient temperature, the solvents are removed under reduced pressure, and the resulting solid is dissolved with an appropriate organic solvent (preferably DCM), and is washed with water and brine. The combined organic layers may be optionally washed with brine, dried over Na$_2$SO$_4$ or MgSO$_4$, then decanted or filtered, prior to concentrating under reduced pressure. The crude product is purified by crystallization or trituration from an appropriate solvent or solvents, or by chromatography to give the target compound.

Illustration of General Procedure L

Example #L.1.1

3-Fluoro-4-{6-[6-(4-fluorophenyl)-imidazo[2,1-b]oxazol-5-yl]-[1,2,4]triazolo[4,3-a]pyridin-3-yl}-N-(3-hydroxy-2,2-dimethylpropyl)-benzamide

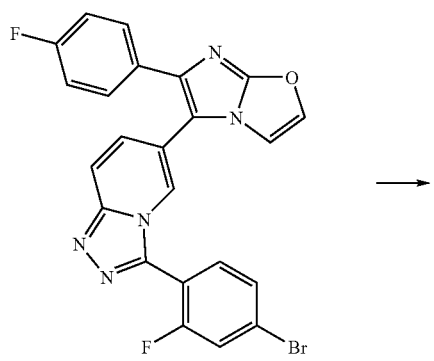

-continued

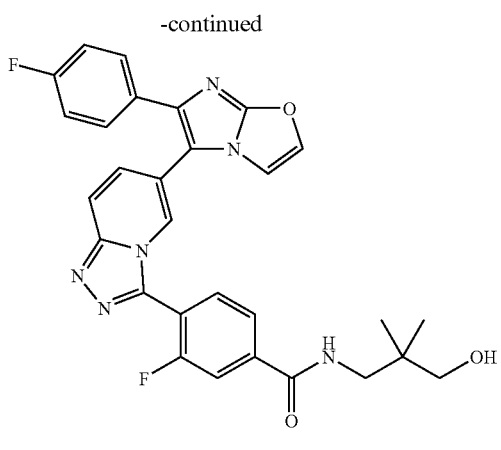

A mixture of 3-(4-bromo-2-fluorophenyl)-6-[6-(4-fluorophenyl)-imidazo[2,1-b]oxazol-5-yl]-[1,2,4]triazolo[4,3-a]pyridine (0.20 g, 0.41 mmol; Example #K.1.3), 3-amino-2,2-dimethyl-propan-1-ol (0.21 g, 2.0 mmol; Lancaster), and TEA (0.175 mL, 1.21 mmol) in DMF (5 mL) was vacuum purged with carbon monoxide three times followed by the addition of dichlorobis(triphenylphosphine)palladium (II) (0.03 g, 0.04 mmol) and subsequent vacuum purging with carbon monoxide five times. The reaction was heated at about 100° C. under an atmosphere of carbon monoxide for about 2 h after which the reaction was cooled and concentrated under reduced pressure. The crude material was dissolved in DCM and purified by flash chromatography using DCM/MeOH (90:10) as eluent. After concentration of the clean fractions, the resulting oil was triturated with $Et_2O$. The resulting solid was filtered and dried to provide the title compound as a light yellow solid (0.19 g, 85%): LC/MS (Table 1, Method a) $R_f$=2.11 min; MS m/z: 543.2 $(M+H)^+$.

TABLE L.1

Examples prepared from 3-(4-bromo-2-fluorophenyl)-6-[6-(4-fluorophenyl)-imidazo[2,1-b]oxazol-5-yl]-[1,2,4]triazolo[4,3-a]pyridine (prepared using A from 6-(4-fluorophenyl)-imidazo[2,1-b]oxazole [prepared according to WO2004110990A2, Example 1, Steps 1-3] and NIS, C using 2-fluoropyridine-5-boronic acid [Asymchem], D using hydrazine, K using 4-bromo-2-fluoro-benzaldehyde) using General Procedure L

| Nucleophile | Product | Example # | $R_t$ min (method) | m/z ESI+ $(M + H)^+$ |
|---|---|---|---|---|
| Methanol | 3-Fluoro-4-{6-[6-(4-fluorophenyl)-imidazo[2,1-b]oxazol-5-yl]-[1,2,4]triazolo[4,3-a]pyridin-3-yl}-benzoic acid methyl ester | L.1.2 | 2.40 (a) | 472.1 |
| 3-Amino-2,2-dimethyl-propan-1-ol [Lancaster] | 3-Fluoro-4-{6-[6-(4-fluorophenyl)-imidazo[2,1-b]oxazol-5-yl]-[1,2,4]triazolo[4,3-a]pyridin-3-yl}-N-(3-hydroxy-2,2-dimethyl-propyl)-benzamide | L.1.3 | 2.11 (a) | 543.2 |
| N,N-Dimethyl-propane-1,3-diamine | N-(3-Dimethylaminopropyl)-3-fluoro-4-{6-[6-(4-fluorophenyl)-imidazo[2,1-b]oxazol-5-yl]-[1,2,4]triazolo[4,3-a]pyridin-3-yl}-benzamide | L.1.4 | 1.76 (a) | 542.2 |

TABLE L.2

Examples prepared from 5-(3-(5-bromo-2-fluorophenyl)-[1,2,4]triazolo[4,3-a]pyridine-6-yl)-6-(4-fluorophenyl)imidazo[2,1-b]oxazole (prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine, K.1 with 5-bromo-2-fluorobenzaldehyde) using General Procedure L

| Nucleophile | Product | Example # | $R_t$ min (method) | m/z ESI+ $(M + H)^+$ |
|---|---|---|---|---|
| 2-Aminoethanol | 4-Fluoro-3-(6-(6-(4-fluorophenyl)imidazo[2,1-b]oxazol-5-yl)-[1,2,4]triazolo[4,3-a]pyridin-3-yl)-N-(2-hydroxyethyl)benzamide | L.2.1 | 1.86 (a) | 501.2 |

TABLE L.2-continued

Examples prepared from 5-(3-(5-bromo-2-fluorophenyl)-[1,2,4]triazolo[4,3-a]pyridine-6-yl)-6-(4-fluorophenyl)imidazo[2,1-b]oxazole (prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine, K.1 with 5-bromo-2-fluorobenzaldehyde) using General Procedure L

| Nucleophile | Product | Example # | $R_t$ min (method) | m/z ESI+ $(M + H)^+$ |
|---|---|---|---|---|
| N1,N1-Dimethylpropane-1,2-diamine | N-(3-(Dimethylamino)propyl)-4-fluoro-3-(6-(6-(4-fluorophenyl)imidazo[2,1-b]oxazol-5-yl)-[1,2,4]triazolo[4,3-a]pyridin-3-yl)benzamide | L.2.2 | 1.68 (a) | 542.2 |
| 3-Amino-2,2-dimethylpropan-1-ol [Alfa Aesar] | 4-Fluoro-3-(6-(6-(4-fluorophenyl)-imidazo[2,1-b]oxazol-5-yl)-[1,2,4]triazolo[4,3-a]pyridin-3-yl)-N-(3-hydroxy-2,2-dimethylpropyl)benzamide | L.2.3 | 2.13 (a) | 543.2 |

TABLE L.3

Examples prepared from 3-(4-bromo-2-fluorophenyl)-6-[6-(4-fluorophenyl)-imidazo[2,1-b]oxazol-5-yl]-[1,2,4]triazolo[4,3-a]pyridine (prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine, K.1 with 4-bromo-2-fluorobenzaldehyde) using General Procedure L

| Nucleophile | Product | Example # | $R_t$ min (method) | m/z ESI+ $(M + H)^+$ |
|---|---|---|---|---|
| (1-(Aminomethyl)cyclopropyl)methanol | 3-Fluoro-4-(6-(6-(4-fluorophenyl)imidazo[2,1-b]oxazol-5-yl)-[1,2,4]triazolo[4,3-a]pyridin-3-yl)-N-((1-(hydroxymethyl)cyclopropyl)methyl)benzamide | L.3.1 | 2.00 (a) | 541.2 |
| 2-Aminoethanol | 4-(6-(6-(4-Fluorophenyl)imidazo[2,1-b]oxazol-5-yl)-[1,2,4]triazolo[4,3-a]pyridin-3-yl)-3-fluoro-N-(2-hydroxyethyl)benzamide | L.3.2 | 1.84 (a) | 501.2 |

TABLE L.4

Examples prepared from 3-(4-bromo-2-fluorophenyl)-6-[6-(2,4-difluorophenyl)-imidazo[2,1-b]oxazol-5-yl]-[1,2,4]triazolo[4,3-a]pyridine (prepared using K.1 from Example #2, step B with 4-bromo-2-fluorobenzaldehyde) using General Procedure L

| Nucleophile | Product | Example # | $R_t$ min (method) | m/z ESI+ $(M + H)^+$ |
|---|---|---|---|---|
| 3-Amino-2,2-dimethylpropan-1-ol | 4-(6-(6-(2,4-Difluorophenyl)imidazo[2,1-b]oxazol-5-yl)-[1,2,4]triazolo[4,3-a]pyridin-3-yl)-3-fluoro-N-(3-hydroxy-2,2-dimethylpropyl)benzamide | L.4.1 | 2.09 (a) | 561.2 |

General Procedure M: Acidic Cleavage of a Boc-Protected Amine

To a solution of Boc-protected amine (preferably 1 equiv) in an organic solvent (such as DCM or MeOH) is added TFA or HCl (2-20 equiv, preferably 10-20 equiv). After about 1-24 h (preferably 1-4 h), the reaction was concentrated under reduced pressure then an aqueous base (such as saturated aqueous NaHCO$_3$) is added. The aqueous layer is extracted with an organic solvent (such as DCM or DCM/MeOH (9:1)]). The combined organic layers may be optionally washed with brine, dried over Na$_2$SO$_4$ or MgSO$_4$, then decanted or filtered, prior to concentrating under reduced pressure. The crude material is purified by chromatography, trituration with an appropriate solvent, or crystallization from one or more solvents to give the target compound. Alternatively, the impure target compound is dissolved in a suitable solvent (such as MeOH or EtOH) and HCl (for example, 1.25 M HCl in MeOH or 1M HCl in Et$_2$O) is added. If the product precipitates it is directly filtered and dried or, if necessary, is purified further by trituration with an appropriate solvent or crystallization from one or more solvents to give the target compound.

Illustration of General Procedure M

Example #M.1.1

6-[6-(4-Fluorophenyl)-imidazo[2,1-b]thiazol-5-yl]-1-pyrrolidin-2-ylmethyl-1H-benzoimidazol-2-ylamine

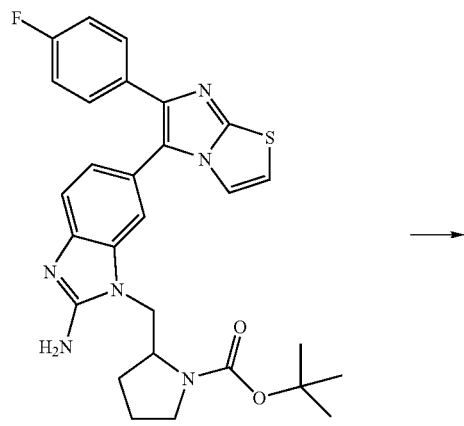

→

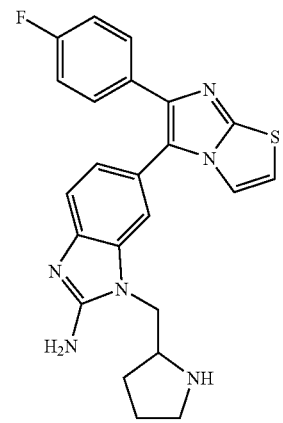

To a solution of 2-{2-amino-6-[6-(4-fluorophenyl)-imidazo[2,1-b]thiazol-5-yl]benzimidazol-1-ylmethyl}pyrrolidine-1-carboxylic acid tert-butyl ester (0.12 g, 0.22 mmol; Example #G.1.16) in DCM (2.7 mL) was added TFA (0.30 mL). After about 18 h, the reaction was concentrated under reduced pressure then saturated aqueous NaHCO$_3$ was added and extracted with DCM/MeOH (9:1, 3×30 mL). The combined organic layers were washed with brine, dried over Na$_2$SO$_4$, decanted, and concentrated. The crude material was purified by silica gel chromatography using DCM/MeOH/NH$_4$OH (stepwise gradient 980:18:2 to 950:45:5). After concentration of the column fractions, the residue was dissolved in DCM and heptane was added until a precipitate formed. The mixture was then concentrated under reduced pressure to give the title compound (0.065 g, 67%): LC/MS (Table 1, Method b) R$_f$ =1.47 min; MS m/z: 433.1 (M+H)$^+$.

TABLE M.1

Examples prepared from Boc-protected amines and TFA using General Procedure M

| Boc-protected amine | Product | Example # | R$_f$ min (method) | m/z ESI+ (M + H)$^+$ |
|---|---|---|---|---|
| 3-{2-Amino-6-[6-(4-fluorophenyl)-imidazo[2,1-b]thiazol-5-yl]-benzimidazol-1-ylmethyl}-azetidine-1-carboxylic acid tert-butyl ester [prepared using A from 6-(4-fluorophenyl)-imidazo[2,1-b]thiazole [WO2004110990A2, Example 2, Step 1] and NIS, C from Preparation #B.1, and D from 3-aminomethyl-1-N-Boc-azetidine [Astatech], E, G] | 1-Azetidin-3-ylmethyl-6-[6-(4-fluorophenyl)-imidazo[2,1-b]thiazol-5-yl]-1H-benzimidazol-2-ylamine | M.1.2 | 1.35 (b) | 419.2 |

General Procedure M.1: Acidic Cleavage of a Boc-Protected Amine

To a solution of Boc-protected amine (preferably 1 equiv) in an organic solvent (such as DCM, dioxane or MeOH) is added TFA or HCl (2-20 equiv, preferably 10-20 equiv). The reaction mixture is stirred at about 0-100° C. (preferably about 20-60° C.). After about 1-24 h (preferably about 1-4 h), the reaction is concentrated under reduced pressure then an aqueous base (such as saturated aqueous $NaHCO_3$) is added. The aqueous layer is extracted with an organic solvent (such as DCM or DCM/MeOH (9:1)). The combined organic layers may be optionally washed with brine, dried over $Na_2SO_4$ or $MgSO_4$, then decanted or filtered, prior to concentrating under reduced pressure. The crude material is purified by chromatography, trituration with an appropriate solvent, or crystallization from one or more solvents to give the target compound. Alternatively, the impure target compound is dissolved in a suitable solvent (such as MeOH or EtOH) and HCl (for example, 1.25 M HCl in MeOH or 1M HCl in $Et_2O$) is added. If the product precipitates it is directly filtered and dried or, if necessary, is purified further by trituration with an appropriate solvent or crystallization from one or more solvents to give the target compound.

Illustration of General Procedure M.1

Example #M.1.1.1

6-(4-Fluorophenyl)-5-(3-(piperidin-3-yl)-[1,2,4]triazolo[4,3a]pyridin-6-yl)imidazo[2,1-b]oxazole

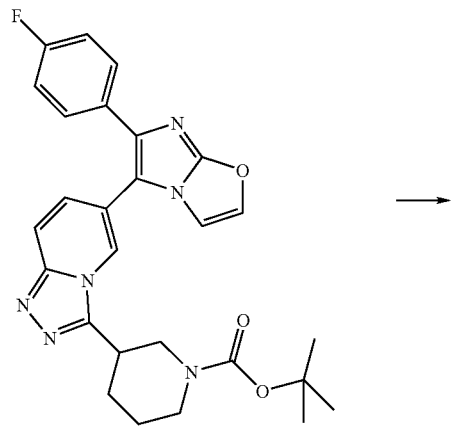

→

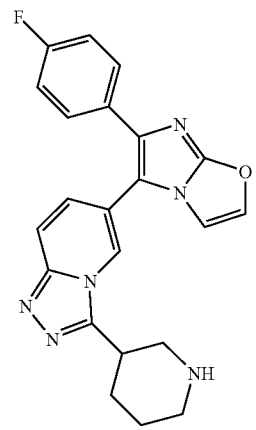

To a round bottom flask containing tert-butyl 3-(6-(6-(4-fluorophenyl)imidazo[2,1-b]oxazol-5-yl)-[1,2,4]triazolo[4,3-a]pyridin-3-yl)piperidine-1-carboxylate (0.364 g, 0.724 mmol; Example #K.1.1.1) was added 1,4-dioxane (5 mL) and 6.0 N HCl (1.21 mL, 7.24 mmol). The reaction mixture was stirred at ambient temperature for about 2 h and then at about 60° C. for about 1 h. The reaction mixture was diluted with DCM (50 mL) and washed with 1.0 N NaOH (50 mL), dried with $MgSO_4$, filtered and concentrated in vacuo. The crude solid was purified by flash chromatography (silica gel; DCM/MeOH gradient from 1:0 to 19:1) to title compound (0.221 g, 76%) as a white solid. LC/MS (Table 1, Method a) $R_t$, =1.64 min; MS 403.2 m/z $(M+H)^+$.

TABLE M.1.1

Examples prepared from Boc-protected amines and TFA using General Procedure M.1

| Boc-protected amine | Product | Example # | $R_t$ min (method) | m/z ESI+ $(M + H)^+$ |
|---|---|---|---|---|
| tert-Butyl-3-(6-(6-(4-fluorophenyl)imidazo[2,1-b]oxazol-5-yl-[1,2,4]triazolo[4,3-a]pyridin-3-yl)azetidine-1-carboxylate [Example #K.1.1.14] | 5-(3-(Azetidin-3-yl)-[1,2,4]triazolo[4,3-a]pyridin-6-yl)-6-(4-fluorophenyl)imidazo[2,1-b]oxazole | M.1.1.2 | 1.53 (a) | 375.2 |
| tert-Butyl 3-(6-(6-(4-fluorophenyl)imidazo[2,1-b]oxazol-5-yl)-[1,2,4]triazolo[4,3-a]pyridin-3-yl)pyrrolidine-1-carboxylate [Example #K.1.1.19] | 6-(4-Fluorophenyl)-5-(3-(pyrrolidin-3-yl)-[1,2,4]triazolo[4,3-a]pyridin-6-yl)imidazo[2,1-b]oxazole | M.1.1.3 | 1.58 (a) | 389.2 |

TABLE M.1.1-continued

Examples prepared from Boc-protected amines and TFA using General Procedure M.1

| Boc-protected amine | Product | Example # | $R_t$ min (method) | m/z ESI+ (M + H)$^+$ |
|---|---|---|---|---|
| tert-Butyl (trans)-4-(6-(6-(4-fluorophenyl)imidazo[2,1-b]oxazol-5-yl)-[1,2,4]triazolo[4,3-a]pyridin-3-yl)cyclohexylcarbamate [Example #K.1.1.35] | (trans)-4-(6-(6-(4-Fluorophenyl)imidazo[2,1-b]oxazol-5-yl)-[1,2,4]triazolo[4,3-a]pyridin-3-yl)cyclohexanamine | M.1.1.4 | 1.68 (a) | 417.2 |
| tert-Butyl (cis)-4-(6-(6-(4-fluorophenyl)imidazo[2,1-b]oxazol-5-yl)-[1,2,4]triazolo[4,3-a]pyridin-3-yl)cyclohexylcarbamate [Example #K.1.1.34] | (cis)-4-(6-(6-(4-Fluorophenyl)imidazo[2,1-b]oxazol-5-yl)-[1,2,4]triazolo[4,3-a]pyridin-3-yl)cyclohexanamine | M.1.1.5 | 1.75 (a) | 417.2 |

TABLE M.1.2

Examples prepared from Boc-protected amines and HCl using General Procedure M.1

| Boc-protected amine | Product | Example # | $R_t$ min (method) | m/z ESI+ (M + H)$^+$ |
|---|---|---|---|---|
| tert-Butyl 4-(6-(6-(4-fluorophenyl)imidazo[2,1-b]oxazol-5-yl)-[1,2,4]triazolo[4,3-a]pyridin-3-yl)piperidine-1-carboxylate [Example #K.1.1.6) | 6-(4-Fluorophenyl)-5-(3-(piperidin-4-yl)-[1,2,4]triazolo[4,3-a]pyridin-6-yl)imidazo[2,1-b]oxazole | M.1.2.1 | 1.58 (a) | 403.2 |
| tert-Butyl 4-((6-(6-(4-fluorophenyl)imidazo[2,1-b]oxazol-5-yl)-[1,2,4]triazolo[4,3-a]pyridin-3-yl)methyl)piperidine-1-carboxylate [Example #K.1.1.11] | 6-(4-Fluorophenyl)-5-(3-(piperidin-4-ylmethyl)-[1,2,4]triazolo[4,3-a]pyridin-6-yl)imidazo[2,1-b]oxazole | M.1.2.2 | 1.61 (a) | 417.2 |

General Procedure N: Halogenation of a Ketone with Bromine

To a flask containing a ketone (preferably 1 equiv) in a suitable organic solvent (such as DCM, ACN, or HOAc, preferably DCM) is added bromine (0.9-1.5 equiv, preferably 0.99 equiv) neat or as a solution in the aforementioned organic solvent (preferably as a solution in organic solvent) over a period of about 5 min to 2 h (preferably about 1 h) at about 0-40° C. (preferably about 23° C.). Optionally, a few drops of HBr in HOAc may be added to the reaction mixture. Once the bromine is completely added, the reaction mixture is stirred for about 15 min-4 h (preferably about 1 h) at about 0-40° C. (preferably 20-30° C.). Cold water is added and the mixture is stirred for about 5-30 min (preferably about 15 min) at ambient temperature. The layers are separated and the organic solution is optionally washed with water and/or brine and is dried over Na$_2$SO$_4$ or MgSO$_4$, then decanted or filtered, and the solvent is removed under reduced pressure to give the target compound. The crude product can be used without additional purification. Optionally, the crude material can be purified by crystallization or trituration from an appropriate solvent or solvents to give the target compound.

Illustration of General Procedure N

Example #N.1

2-Bromo-1-(2,4,5-trifluorophenyl)ethanone

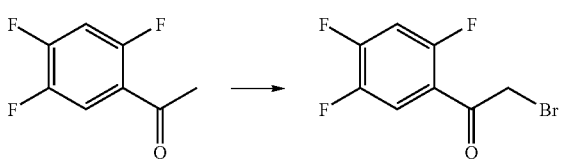

A 1 L 3-neck round bottom flask was charged with 2',4',5'-trifluorophenylacetophenone (49.7 g, 285 mmol) and DCM (350 mL). The flask was equipped with a 250 mL dropping funnel that contained a solution of bromine (14.6 mL, 283 mmol) in DCM (125 mL). This solution was added to the reaction flask over about 1 h at about 23° C. Once addition of the solution was complete, the reaction mixture was stirred for about 1 h at ambient temperature. Ice water was added to the reaction flask and the mixture was stirred for about 15 min. The layers were separated and the organic solution was then washed with water and brine, dried over MgSO$_4$, filtered, and the solvent was removed under reduced pressure to give the title compound as a pale yellow solid (70.3 g, 97%): LC/MS (Table 1, Method d) R$_t$=2.20 min; MS m/z 251.0 (M+H)$^+$.

General Procedure O: Cyclization to Form an Imidazo[1,2-b]oxazole

To a flask containing a bromoketone (1-2 equiv, preferably 1.5 equiv) in an organic solvent or solvents (such as THF, ACN, DCM, dioxane, or THF/ACN, preferably THF/ACN) is added an optionally substituted oxazole-2-amine (preferably 1 equiv). The mixture is stirred at about 0-70° C. (preferably about 23° C.) for about 2-30 h (preferably about 20 h). The reaction mixture is cooled to about −78-0° C. (preferably about −10° C.) for about 5-30 min (preferably about 15 min) and the solid is collected by vacuum filtration, washed with additional organic solvent (such as THF, ACN, DCM, or 1,4-dioxane, preferably ACN), and dried under vacuum. To this intermediate (preferably 1 equiv) is added an organic solvent (for example, toluene). A solution of TiCl$_4$ (1-5 equiv, preferably 2.5 equiv, in an organic solvent (for example, toluene) is added over about 15 min-1 h (preferably about 30 min) at about −10-23° C. (preferably about 0° C.). The resulting mixture is stirred at about −10-23° C. (preferably about 0° C.) for about 30 min-1 h (preferably about 30 min), followed by heating to about 70-110° C. (preferably about 100° C.) for about 30 min-5 h (preferably about 3 h). The mixture is cooled and the organic solvent is optionally decanted off. Ice water is added to the reaction flask with stirring. The resulting thick suspension is stirred at ambient temperature for about 1-12 h (preferably about 1 h) followed by the addition of a base (for example, Na$_2$CO$_3$) and an organic solvent (such as EtOAc or DCM). The resulting mixture is stirred at ambient temperature for about 30 min-2 h (preferably about 1 h) and then optionally filtered through Celite®. The layers are separated and the organic solution is dried over Na$_2$SO$_4$ or MgSO$_4$, filtered, and concentrated under reduced pressure to give the target compound. Optionally, the product can be purified by crystallization or trituration from an appropriate solvent or solvents, or by chromatography to give the target compound.

Illustration of General Procedure O

Preparation #O.1:
6-(2,4,5-Trifluorophenyl)imidazo[2,1-b]oxazole

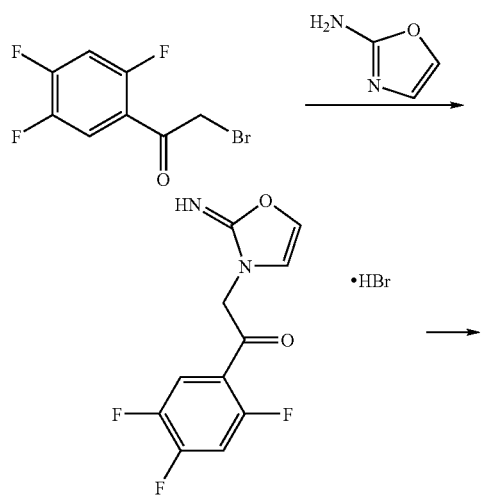

-continued

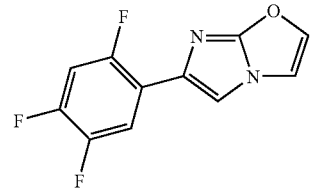

A round bottom flask was charged with 2-bromo-1-(2,4,5-trifluorophenyl)ethanone (50.0 g, 198 mmol; Example #N.1), oxazole-2-amine (11.1 g, 132 mmol; GL Synthesis), THF (200 mL), and ACN (330 mL). The resulting mixture was stirred at about 23° C. for about 20 h. The suspension was cooled to about −10° C. for about 15 min and the solid was collected by vacuum filtration, washed with additional ACN (150 mL), and dried under vacuum to give 2-(2-iminooxazol-3(2H)-yl)-1-(2,4,5-trifluorophenyl)ethanone hydrobromide (35.1 g, 79%) as a white solid. A portion of this material (20.0 g, 59.3 mmol) was suspended in toluene (140 mL) and the suspension was cooled to about 0° C. To the flask was added a 1.0 M solution of TiCl$_4$ in toluene (154 mL) over about 30 min. The mixture was stirred at about 0° C. for about 30 min and was then heated to about 100° C. for about 3 h. The mixture was cooled to ambient temperature, the toluene was decanted off, and ice was added with stirring to the remaining residue. The mixture was adjusted to about pH 8 with the addition of solid Na$_2$CO$_3$, followed by the addition of EtOAc. The mixture was stirred for about 1 h and then passed through a pad of Celite®. The layers were separated and the organic solution was dried over MgSO$_4$, filtered, and concentrated to dryness under reduced pressure to give the title compound as a white solid (11.7 g, 83%): LC/MS (Table 1, Method d) R$_t$=2.11 min; MS m/z 239.1 (M+H)$^+$.

General Procedure P: Amide Bond Formation

Formation of the amide bond can occur in any of three following ways: 1) To a solution or suspension of a carboxylic acid (1-5 eq) or an amine (1-5 equiv) in a suitable solvent (such as DCM, DCE, THF or 1,4-dioxane, preferably DCM) is added a base (such as TEA, DIEA, pyridine, preferably TEA, 1-20 equiv, preferably 1-20 equiv), and a peptide coupling reagent (such as BOP-Cl, IBCF, HATU, EDCI, preferably EDCI, 1-10 equiv, preferably 1-10 equiv). 2) To a solution or suspension of a carboxylic acid in a suitable solvent (such as such as DCM, DCE, THF or 1,4-dioxane, preferably DCM), is added thionyl chloride or oxalyl chloride (preferably oxalyl chloride) (1-5 equiv, preferably 3 equiv), and if using oxalyl chloride, DMF (0-1 equiv) is added and then the reaction is stirred for about 5-60 min to form an acid chloride. Alternatively, if the acid chloride is commercially available then the commercial material is used (1-2 equiv, preferably 1.2 equiv). Then a base (such as TEA, DIEA, pyridine, 1-20 equiv) and an amine (1-20 equiv, preferably 10 equiv) is added to the solution or suspension of acid chloride. 3) To a solution or suspension of an amine (such as dimethylamine or methylamine) and an anhydride (1-5 equiv, preferably 1-5 equiv; such as acetic anhydride) in a suitable solvent (such as DCM, DCE, THF or 1,4-dioxane, preferably DCM), is added a base (such as TEA, DIEA or pyridine, preferably TEA, 1-5 equiv, preferably 3 equiv). After either procedure 1, 2 or 3, the reaction mixture is then stirred at about ambient temperature until the reaction is complete (as determined by LC/MS or HPLC or TLC). The reaction mixture is then purified in any of the following three ways: 1.) The reaction mixture is diluted with water or saturated aqueous NaHCO$_3$ solution. The layers are separated and washed with additional water or saturated aqueous NaHCO$_3$ solution. The organic layer is then dried over a suitable drying agent (such as MgSO₄ or Na₂SO₄), filtered, and evaporated to dryness. The material is optionally purified by trituration with a suitable solvent (such as Et₂O, heptane, EtOAc, DCM, or MeOH) to give the target compound. 2.) The crude reaction mixture is filtered through a pad of silica gel, washed with a suitable solvent (such as DCM, MeOH or EtOAc), and concentrated to dryness to give the target compound. 3.) The crude reaction mixture is directly loaded onto a pre-packed silica gel column and purified through a gradient elution using a suitable solvent system (such as heptane/EtOAc or DCM/MeOH) and then optionally further purified by RP-HPLC to give target compound.

Illustration of General Procedure P

Example P.1.1

1-(3-(6-(6-(4-Fluorophenyl)imidazo[2,1-b]oxazol-5-yl)-[1,2,4]triazolo[4,3-a]pyridin-3-yl)pyrrolidin-1-yl)ethanone

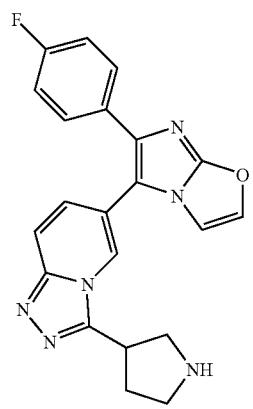

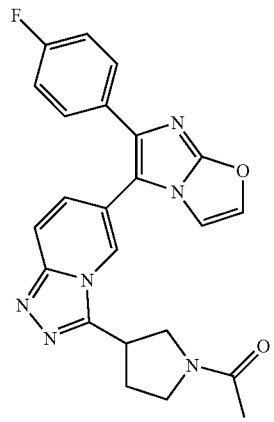

To a suspension of 6-(4-fluorophenyl)-5-(3-(pyrrolidin-3-yl)-[1,2,4]triazolo[4,3-a]pyridin-6-yl)imidazo[2,1-b]oxazole (0.100 g, 0.26 mmol; Example #M.1.1.3) in DCM (5 mL) was added TEA (0.04 mL, 0.26 mmol) and acetyl chloride (0.02 mL, 0.26 mmol). The reaction mixture was stirred at ambient temperature for about 16 h. The crude reaction mixture was purified by flash chromatography (silica gel; DCM/MeOH gradient from 99:1 to 90:10) to afford the title compound (0.02 g, 17%). LC/MS (Table 1, Method a) $R_t$=1.79 min; MS m/z: 431.1 (M+H)⁺.

TABLE P.1

Examples prepared from 6-(4-fluorophenyl)-5-(3-(pyrrolidin-3-yl)-[1,2,4]triazolo[4,3-a]pyridin-6-yl)imidazo[2,1-b]oxazole [Example #M1.1.3] using General Procedure P

| Acylating Agent | Product | Example # | $R_t$ min (method) | m/z ESI+ (M + H)⁺ |
|---|---|---|---|---|
| Pivaloyl chloride | 1-(3-(6-(6-(4-Fluorophenyl)imidazo[2,1-b]oxazol-5-yl)-[1,2,4]triazolo[4,3-a]pyridin-3-yl)pyrrolidin-1-yl)-2,2-dimethylpropan-1-one | P.1.2 | 2.13 (a) | 473.2 |
| 3,3-Dimethylbutanoyl chloride | 1-(3-(6-(6-(4-Fluorophenyl)imidazo[2,1-b]oxazol-5-yl)-[1,2,4]triazolo[4,3-a]pyridin-3-yl)pyrrolidin-1-yl)-3,3-dimethylbutan-1-one | P.1.3 | 2.22 (a) | 487.2 |

TABLE P.2

Examples prepared from 5-(3-(azetidin-3-yl)-[1,2,4]triazolo[4,3-a]pyridine-6-yl)-6-(4-fluorophenyl)imidazo[2,1-b]oxazole [Example #M.1.1.2] using General Procedure P

| Acylating Agent | Product | Example # | $R_t$ min (method) | m/z ESI+ (M + H)+ |
|---|---|---|---|---|
| Acetic anhydride | 1-(3-(6-(6-(4-Fluorophenyl)imidazo[2,1-b]oxazol-5-yl)-[1,2,4]triazolo[4,3-a]pyridin-3-yl)azetidin-1-yl)ethanone | P.2.1 | 1.73 (a) | 417.2 |

TABLE P.3

Examples prepared from (1R,2R)-2-(6-(6-(4-fluorophenyl)imidazo[2,1-b]oxazol-5-yl)-[1,2,4]triazolo[4,3-a]pyridin-3-yl)cyclopropanecarboxylic acid [Preparation #5] using General Procedure P

| Amine | Product | Example # | $R_t$ min (method) | m/z ESI+ (M + H)+ |
|---|---|---|---|---|
| Dimethylamine | (1R,2R)-2-(6-(6-(4-Fluorophenyl)imidazo[2,1-b]oxazol-5-yl)-[1,2,4]triazolo[4,3-a]pyridin-3-yl)-N,N-dimethylcyclopropanecarboxamide | P.3.1 | 1.86 (a) | 431.2 |

TABLE P.4

Examples prepared from acetyl chloride using General Procedure P

| Amine | Product | Example # | $R_t$ min (method) | m/z ESI+ (M + H)+ |
|---|---|---|---|---|
| (cis)-4-(6-(6-(4-Fluorophenyl)imidazo[2,1-b]oxazol-5-yl)-[1,2,4]triazolo[4,3-a]pyridin-3-yl)cyclohexanamine [Example #M.1.1.5] | N-((cis)-4-(6-(6-(4-Fluorophenyl)imidazo[2,1-b]oxazol-5-yl)-[1,2,4]triazolo[4,3-a]pyridin-3-yl)cyclohexyl)acetamide | P.4.1 | 1.84 (a) | 459.2 |
| (trans)-4-(6-(6-(4-Fluorophenyl)imidazo[2,1-b]oxazol-5-yl)-[1,2,4]triazolo[4,3-a]pyridin-3-yl)cyclohexanamine [Example #M.1.1.4] | N-((trans)-4-(6-(6-(4-Fluorophenyl)imidazo[2,1-b]oxazol-5-yl)-[1,2,4]triazolo[4,3-a]pyridin-3-yl)cyclohexyl)acetamide | P.4.2 | 1.87 (a) | 459.2 |
| 6-(4-Fluorophenyl)-5-(3-(piperidin-4-yl)-[1,2,4]triazolo[4,3-a]pyridin-6-yl)imidazo[2,1-b]oxazole [Example #M.1.2.1] | 1-(4-(6-(6-(4-Fluorophenyl)imidazo[2,1-b]oxazol-5-yl)-[1,2,4]triazolo[4,3-a]pyridin-3-yl)piperidin-1-yl)ethanone | P.4.3 | 1.82 (a) | 445.1 |
| 6-(4-Fluorophenyl)-5-(3-(piperidin-3-yl)-[1,2,4]triazolo[4,3-a]pyridin-6-yl)imidazo[2,1-b]oxazole [Example #M.1.1.1] | 1-(3-(6-(6-(4-Fluorophenyl)imidazo[2,1-b]oxazol-5-yl)-[1,2,4]triazolo[4,3-a]pyridin-3-yl)piperidin-1-yl)ethanone | P.4.4 | 1.86 (a) | 445.2 |

TABLE P.5

Examples prepared from 6-(4-fluorophenyl)-5-(3-(piperidin-4-yl)-[1,2,4]triazolo[4,3-a]pyridin-6-yl)imidazo[2,1-b]oxazole [Example #M.1.2.1] using General Procedure P

| Acid Chloride | Product | Example # | $R_t$ min (method) | m/z ESI+ (M + H)+ |
|---|---|---|---|---|
| 3,3-Dimethylbutanoyl chloride | 1-(4-(6-(6-(4-Fluorophenyl)imidazo[2,1-b]oxazol-5-yl)-[1,2,4]triazolo[4,3-a]pyridin-3-yl)piperidin-1-yl)-3,3-dimethylbutan-1-one | P.5.1 | 2.26 (a) | 501.2 |

TABLE P.5-continued

Examples prepared from 6-(4-fluorophenyl)-5-(3-(piperidin-4-yl)-[1,2,4]triazolo[4,3-a]pyridin-6-yl)imidazo[2,1-b]oxazole [Example #M.1.2.1] using General Procedure P

| Acid Chloride | Product | Example # | R$_t$ min (method) | m/z ESI+ (M + H)+ |
|---|---|---|---|---|
| Pivaloyl chloride | 1-(4-(6-(6-(4-Fluorophenyl)imidazo[2,1-b]oxazol-5-yl)-[1,2,4]triazolo[4,3-a]pyridin-3-yl)piperidin-1-yl)-2,2-dimethylpropan-1-one | P.5.2 | 2.19 (a) | 487.2 |

TABLE P.6

Examples prepared from 6-(4-fluorophenyl)-5-(3-(piperidin-4-ylmethyl)-[1,2,4]triazolo[4,3-a]pyridin-6-yl)imidazo[2,1-b]oxazole [Example #M.1.2.2] using General Procedure P

| Acid Chloride | Product | Example # | R$_t$ min (method) | m/z ESI+ (M + H)+ |
|---|---|---|---|---|
| Pivaloyl chloride | 1-(4-((6-(6-(4-Fluorophenyl)imidazo[2,1-b]oxazol-5-yl)-[1,2,4]triazolo[4,3-a]pyridin-3-yl)methyl)piperidin-1-yl)-2,2-dimethylpropan-1-one | P.6.1 | 2.23 (a) | 501.2 |
| 3,3-Dimethylbutanoyl chloride | 1-(4-((6-(6-(4-Fluorophenyl)imidazo[2,1-b]oxazol-5-yl)-[1,2,4]triazolo[4,3-a]pyridin-3-yl)methyl)piperidin-1-yl)-3,3-dimethylbutan-1-one | P.6.2 | 2.29 (a) | 515.2 |

General Procedure Q: Reductive Amination with Formaldehyde

To a solution of an amine (preferably 1 equiv) in formic acid is added a solution (37% in water containing 10-15% MeOH) of formaldehyde (10-100 equiv). The mixture is stirred at about 20-150° C. (preferably about 100° C.). After about 1-8 h (preferably about 1 h), the reaction is cooled to ambient temperature and then the residue is neutralized using a basic aqueous solution (such as saturated aqueous Na$_2$CO$_3$, saturated aqueous NaHCO$_3$ or 2 N NaOH, preferably saturated aqueous NaHCO$_3$) and is partitioned between the aqueous base and an organic solvent (such as DCM or EtOAc, preferably DCM). The organic extract is dried over Na$_2$SO$_4$ or MgSO$_4$ and then filtered prior to concentrating under reduced pressure. The crude product is purified by crystallization or trituration from an appropriate solvent or solvents, or by chromatography to give the target compound.

Illustration of General Procedure Q

Example #Q.1.1

6-(4-Fluorophenyl)-5-(3-(1-methylpiperidin-4-yl)-[1,2,4]triazolo[4,3<]pyridin-6-yl)imidazo[2,1-b]oxazole

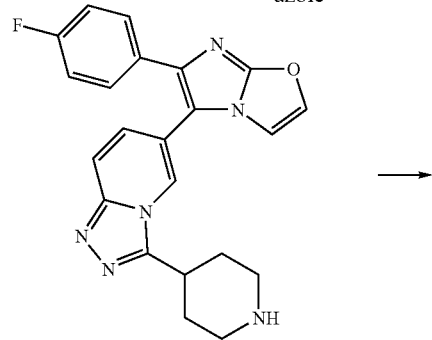

→

-continued

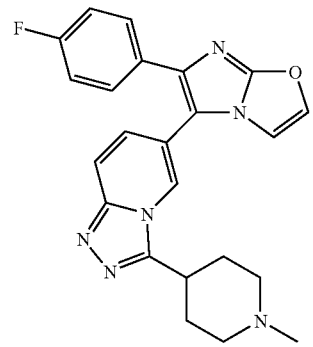

A 25 mL flask was charged with 6-(4-fluorophenyl)-5-(3-(piperidin-4-yl)-[1,2,4]triazolo[4,3-a]pyridin-6-yl)imidazo[2,1-b]oxazole (0.150 g, 0.373 mmol; Example #M.1.2.1) in formic acid (2 mL) to give an orange solution. A solution (37% in water containing 10-15% MeOH) of formaldehyde (2.0 mL, 27 mmol) was added and the mixture was stirred at about 100° C. After about 1 h, the mixture was cooled to ambient temperature and saturated aqueous NaHCO$_3$ was added and was extracted with DCM (2×10 mL). The combined organic layers were washed with brine, dried over MgSO$_4$, decanted, and concentrated. The crude material was purified by silica gel chromatography using DCM/MeOH (stepwise gradient 100:0 to 95:5) to afford the title compound (0.013 g, 9%): LC/MS (Table 1, Method a) R$_t$=1.59 min; MS m/z: 417.2 (M+H)+.

TABLE Q.1

Examples prepared with formaldehyde using General Procedure R

| Amine | Product | Example # | R$_t$ min (method) | m/z ESI+ (M + H)⁺ |
|---|---|---|---|---|
| (cis)-4-(6-(6-(4-Fluorophenyl)imidazo[2,1-b]oxazol-5-yl)-[1,2,4]triazolo[4,3-a]pyridin-3-yl)cyclohexanamine [Example #M.1.1.5] | (cis)-4-(6-(6-(4-Fluorophenyl)imidazo[2,1-b]oxazol-5-yl)-[1,2,4]triazolo[4,3-a]pyridin-3-yl)-N,N-dimethylcyclohexanamine | Q.1.2 | 1.43 (a) | 445.2 |
| (trans)-4-(6-(6-(4-Fluorophenyl)imidazo[2,1-b]oxazol-5-yl)-[1,2,4]triazolo[4,3-a]pyridin-3-yl)cyclohexanamine [Example #M.1.1.4] | (trans)-4-(6-(6-(4-Fluorophenyl)imidazo[2,1-b]oxazol-5-yl)-[1,2,4]triazolo[4,3-a]pyridin-3-yl)-N,N-dimethylcyclohexanamine | Q.1.3 | 1.82 (a) | 445.2 |

Example #1

6-[6-(4-Fluorophenyl)-imidazo[2,1-b]oxazol-5-yl]-2-pyridin-4-yl-1H-benzimidazole Step A: 6-[6-(4-Fluorophenyl)-imidazo[2,1-b]oxazol-5-yl]-2-pyridin-4-yl-H-benzoimidazole 3-oxide

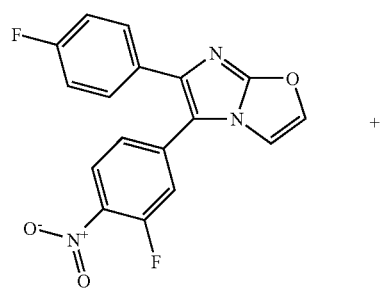

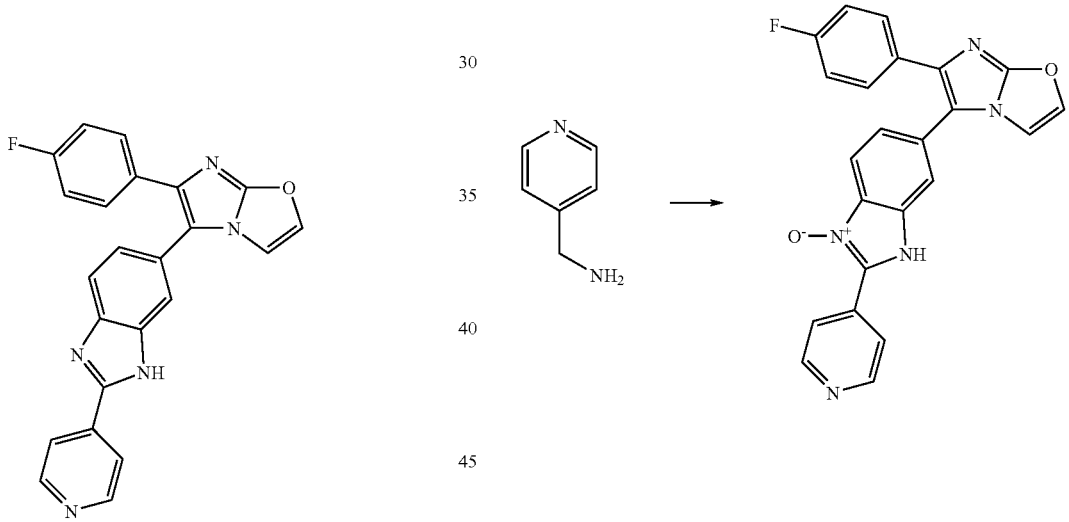

To a suspension of 5-(3-fluoro-4-nitrophenyl)-6-(4-fluorophenyl)-imidazo[2,1-b]oxazole (0.40 g, 1.1 mmol; Preparation #C.1) in ACN (3.0 mL) was added TEA (0.32 mL, 2.3 mmol) and 1-pyridin-4-ylmethanamine (0.14 mL, 1.4 mmol). The reaction was heated at about 80° C. for about 4 h then cooled to about 4° C. Since no precipitate formed, heptane was added followed by cold ACN (ca. 4° C.). The resulting solid was filtered, washing with cold ACN (ca. 4° C.) and heptane, and dried in vacuum oven at about 55-65° C. to give title compound (0.19 g, 37%). A second crop formed in the filtrate which was then filtered, washing with ACN, and dried in vacuum oven at about 55-65° C. to give title compound (0.088 g, 17%): LC/MS (Table 1, Method b) R$_t$ =1.85 min; MS m/z: 412.1 (M+H)⁺.

133

Step B: 6-[6-(4-Fluorophenyl)-imidazo[2,1-b]oxazol-5-yl]-2-pyridin-4-yl-1H-benzimidazole

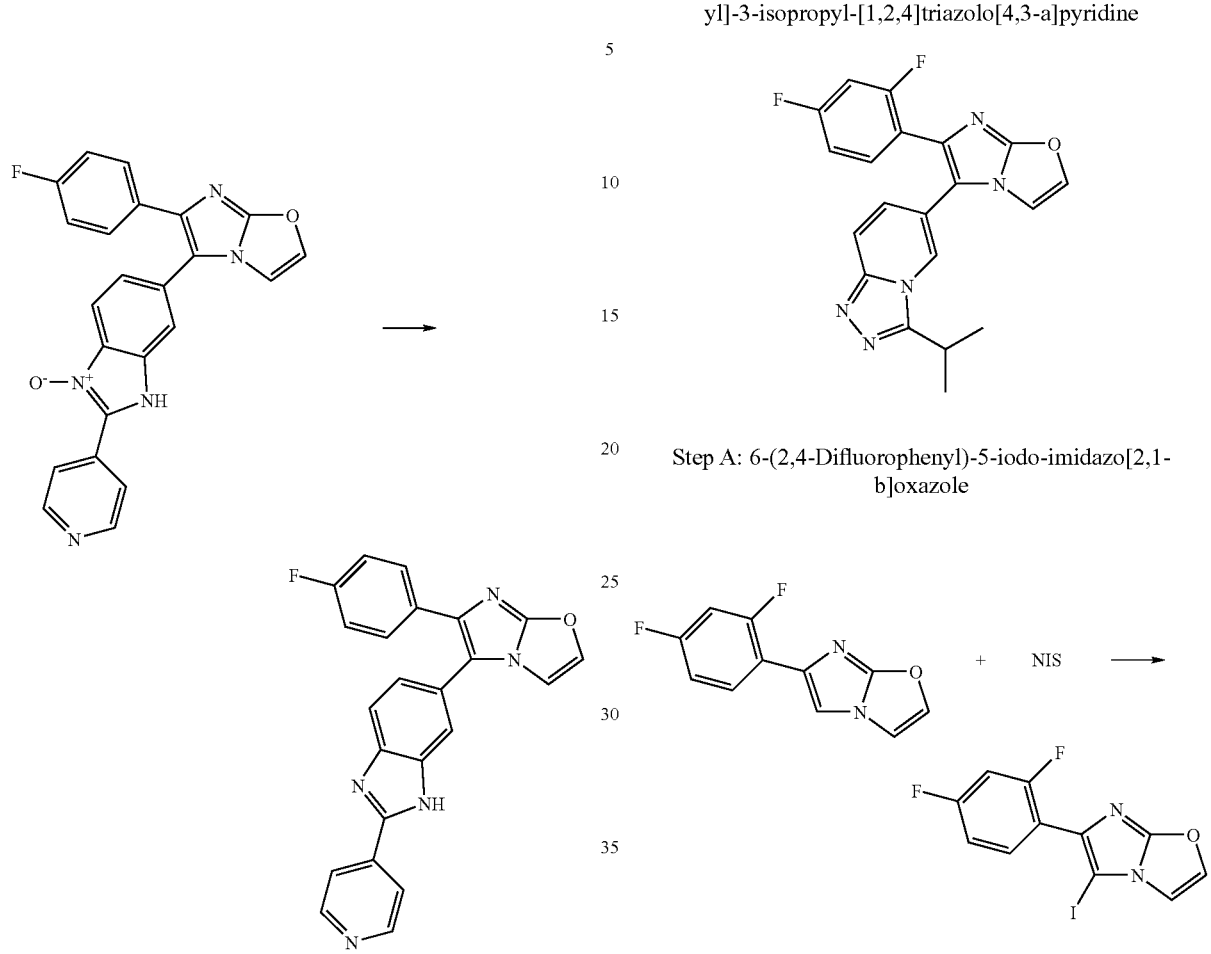

A mixture of 6-[6-(4-fluorophenyl)-imidazo[2,1-b]oxazol-5-yl]-2-pyridin-4-yl-1H-benzoimidazole 3-oxide (0.26 g, 0.56 mmol), tin(II) chloride dihydrate (0.64 g, 2.8 mmol) and EtOH (5.5 mL) was heated at about 70° C. for about 18 h. The reaction was poured over ice then the pH was adjusted to 8 with saturated aqueous NaHCO₃ and filtered to remove tin salts. The filter cake was stirred with EtOAc (3×30 mL) then filtered. Each organic filtrate was then used to extract the initial aqueous filtrate. The combined organic layers were washed with brine, dried over Na₂SO₄, decanted, and concentrated. To the crude material was added 6 M HCl in water (0.94 mL; VWR). The reaction was cooled to about 0° C. and then NaNO₂ (0.058 g, 0.85 mmol) in water (0.53 mL) was added dropwise. After about 2 h, no reaction was seen by LC-MS. The reaction was filtered, washing with water, and dried in the vacuum oven at 55-65° C. to give the title compound (0.15 g, 64%): LC/MS (Table 1, Method b) $R_t$ =1.82 min; MS m/z: 396.2 (M+H)⁺.

134

Example #2

6-[6-(2,4-Difluorophenyl)-imidazo[2,1-b]oxazol-5-yl]-3-isopropyl-[1,2,4]triazolo[4,3-a]pyridine

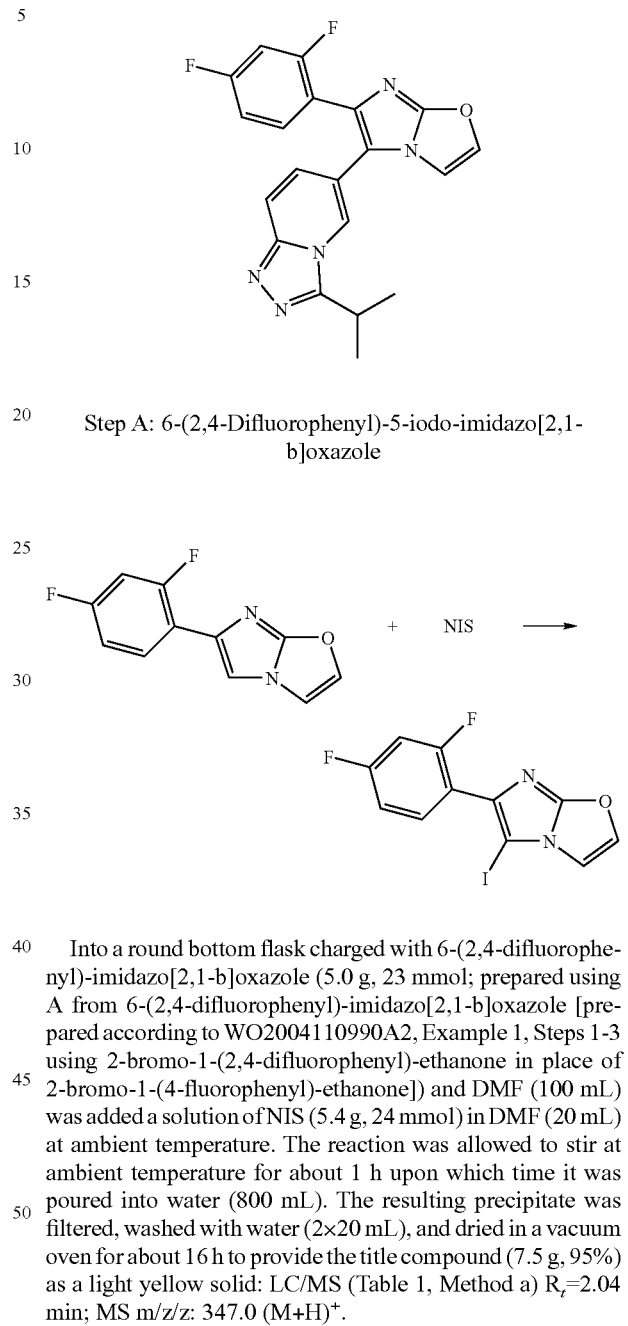

Step A: 6-(2,4-Difluorophenyl)-5-iodo-imidazo[2,1-b]oxazole

Into a round bottom flask charged with 6-(2,4-difluorophenyl)-imidazo[2,1-b]oxazole (5.0 g, 23 mmol; prepared using A from 6-(2,4-difluorophenyl)-imidazo[2,1-b]oxazole [prepared according to WO2004110990A2, Example 1, Steps 1-3 using 2-bromo-1-(2,4-difluorophenyl)-ethanone in place of 2-bromo-1-(4-fluorophenyl)-ethanone]) and DMF (100 mL) was added a solution of NIS (5.4 g, 24 mmol) in DMF (20 mL) at ambient temperature. The reaction was allowed to stir at ambient temperature for about 1 h upon which time it was poured into water (800 mL). The resulting precipitate was filtered, washed with water (2×20 mL), and dried in a vacuum oven for about 16 h to provide the title compound (7.5 g, 95%) as a light yellow solid: LC/MS (Table 1, Method a) $R_t$=2.04 min; MS m/z: 347.0 (M+H)⁺.

Step B: {5-[6-(2,4-Difluorophenyl)-imidazo[2,1-b]oxazol-5-yl]-pyridin-2-yl}-hydrazine

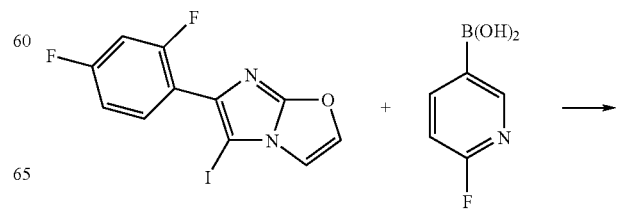

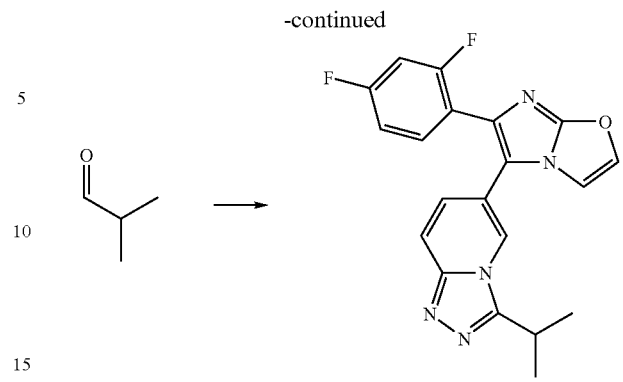

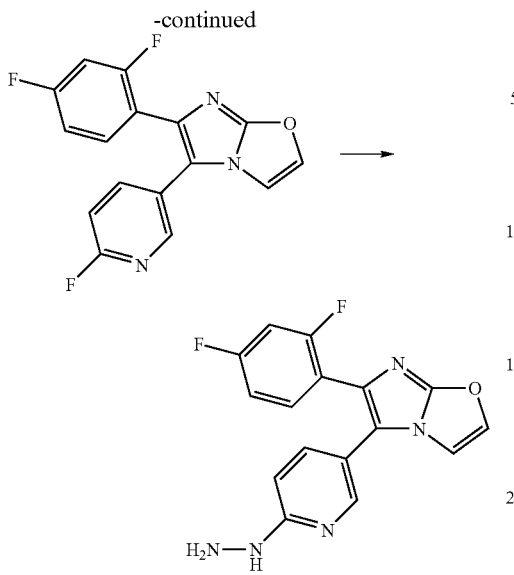

A mixture of 6-(2,4-difluorophenyl)-5-iodo-imidazo[2,1-b]oxazole (5 g, 14.5 mmol), 2-fluoropyridine-5-boronic acid (3.1 g, 22 mmol; Asymchem), $Cs_2CO_3$ (12 g, 36 mmol), and trans-dichloro[bis(triphenylphosphine)]palladium (II) (1.1 g, 1.5 mmol) was dissolved in 1,4-dioxane (100 mL) and water (10 mL) at ambient temperature. The reaction was vacuum purged with $N_2$ three times followed by heating to about 80° C. for about 2 h. The reaction was allowed to cool to ambient temperature upon which time it was concentrated under reduced pressure. The resulting oil was dissolved in DCM, filtered through a pad of silica gel and the silica gel was washed DCM (3×10 mL). The filtrate was concentrated under reduced pressure to provide a yellow solid. This solid was dissolved in n-PrOH (50 mL) followed by the addition of hydrazine hydrate (5.0 mL, 160 mmol) and the reaction was heated at about 100° C. for about 16 h. After this time the reaction was concentrated, and the resulting solid was triturated with $Et_2O$ and filtered. The filter cake was washed with water and dried in a vacuum oven for about 16 h to provide the title compound (2.98 g, 63% for 2 steps) as an off-white solid: LC/MS (Table 1, Method a) $R_t$=1.62 min; MS m/z: 342.1 $(M+H)^+$.

Step C: 6-[6-(2,4-Difluorophenyl)-imidazo[2,1-b]oxazol-5-yl]-3-isopropyl-[1,2,4]triazolo[4,3-a]pyridine

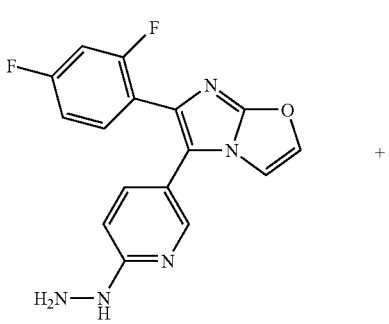

+

In a round bottom flask {5-[6-(2,4-difluorophenyl)-imidazo[2,1-b]oxazol-5-yl]-pyridin-2-yl}-hydrazine (0.35 g, 1.1 mmol) and 2-methylpropionaldehyde (0.1 mL, 1.1 mmol) was dissolved in MeOH (5 mL) followed by heating to about 60° C. for about 1 h. The reaction was allowed to cool to ambient temperature and then iodobenzene diacetate (0.35 g, 1.1 mmol) was added followed by stirring for about 1 h. The reaction was then purified directly by flash chromatography using DCM/MeOH (90:10) as eluent followed by titration with $Et_2O$ to provide the title compound (0.075 g, 18%) as an off-white solid: LC/MS (Table 1, Method a) $R_t$ =2.12 min; MS m/z: 380.2 $(M+H)^+$.

Example #3

(6-(6-(4-Fluorophenyl)imidazo[2,1-b]oxazol-5-yl)-[1,2,4]triazolo[4,3-]pyridin-3-yl)methanol

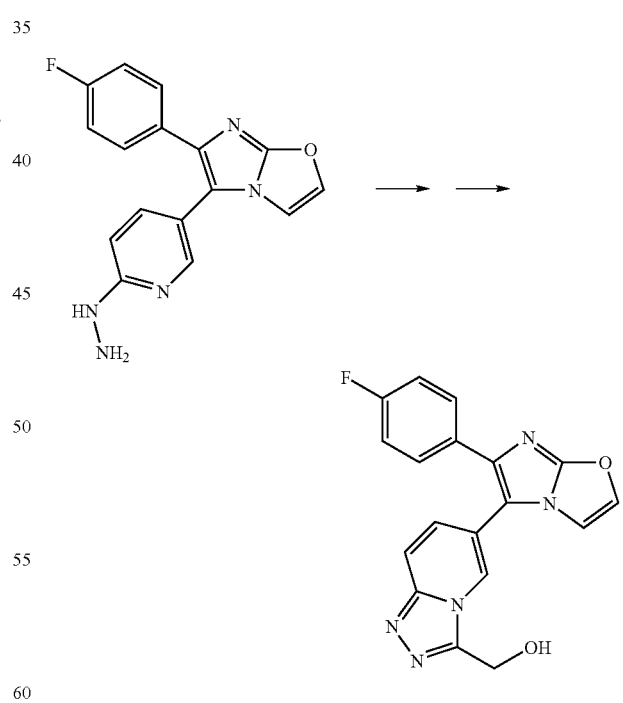

The 6-(4-fluorophenyl)-5-(6-hydrazinylpyridin-3-yl)imidazo[2,1-b]oxazole (0.250 g, 0.808 mmol; prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine) and 2-(tert-butyldimethylsilyloxy)acetaldehyde (0.141 g, 0.808 mmol) were heated in MeOH (6 mL) for about 1.0 h at about 60° C. The MeOH was evaporated then DCM (6 mL) was added followed by iodobenzene diacetate (0.260 g, 0.808 mmol). The reaction was stirred for about 15 min and then diluted with DCM. The mixture was extracted with saturated aqueous NaHCO₃ and then the organic layer was separated and dried over MgSO₄, filtered and evaporated. The residue was dissolved in THF (3 mL) and then TBAF (1M in THF, 0.889 mL, 0.889 mmol) was added. The mixture was stirred for about 15 min at ambient temperature then EtOAc (20 mL) was added. The mixture was extracted with saturated aqueous NaHCO₃ then the organic layer was separated, dried over MgSO₄, filtered, and evaporated. The residue was purified by flash chromatography on 10 g silica gel with 9:1 DCM/MeOH as an eluent. The fractions containing product were evaporated and the residue was triturated with Et₂O (4 mL). The solid was collected by filtration and then dried under vacuum for 2 d at 60° C. to provide the title compound (0.109 g, 38.6%) as a light yellow solid: LC/MS (Table 1, Method a) R$_f$=1.75 min; MS m/z: 350.1 (M+H)⁺.

Example #4

2-(6-(6-(4-Fluorophenyl)imidazo[2,1-b]oxazol-5-yl)-[1,2,4]triazolo[4,3-a]pyridin-3-yl)propan-2-ol

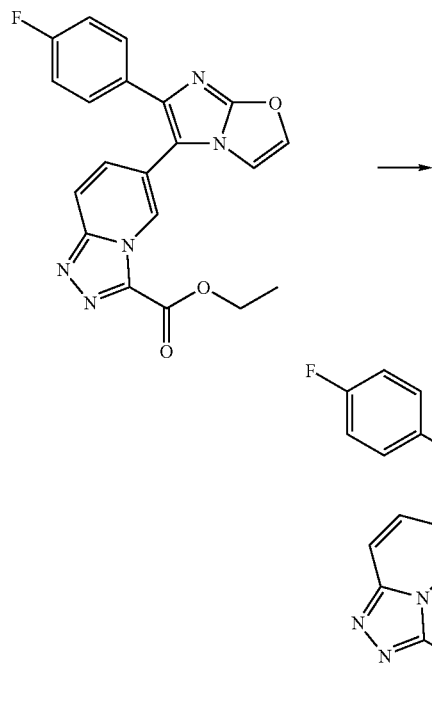

The ethyl 6-(6-(4-fluorophenyl)imidazo[2,1-b]oxazol-5-yl)-[1,2,4]triazolo[4,3-a]pyridine-3-carboxylate (0.250 g, 0.639 mmol; prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine, K.1 with ethyl 2-oxoacetate) was suspended in THF (2.5 mL) then cooled to about −78° C. Methylmagnesium bromide (1.4 M in THF, 1.0 mL, 1.40 mmol) was added and then the mixture was warmed to ambient temperature. Additional methylmagnesium bromide (0.20 mL; 0.28 mmol) was added and then the mixture was stirred for about 15 min. Saturated aqueous ammonium chloride solution (1-2 mL) was added and then the mixture was stirred overnight. The reaction was diluted with DCM and then the layers were separated. The organic solution was dried over MgSO₄ and then filtered. The filtrate was evaporated then purified by flash chromatography on 10 g silica gel with 95:5 DCM/MeOH as an eluent to give a residue that was triturated with Et₂O/heptane to give the title compound (0.010 g, 4.1% yield): LC/MS (Table 1, Method a) R$_f$=1.89 min; MS m/z: 378.1 (M+H)⁺.

Example #5

5-(6-(2,4-Difluorophenyl)imidazo[2,1-b]oxazol-5-yl)-3-isopropylbenzo[d]isoxazole Step A:
4-Bromo-2-(1-hydroxy-2-methylpropyl)phenol

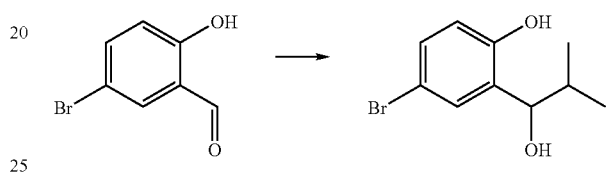

The 5-bromo-2-hydroxybenzaldehyde (4.00 g, 19.9 mmol) in Et₂O (40.0 mL) and THF (10.0 mL) was added dropwise to the isopropylmagnesium chloride (2 M in Et₂O, 29.8 mL, 59.7 mmol) at ambient temperature. The reaction was stirred for about 15 min then MeOH (5 mL) was added followed by saturated aqueous NH₄Cl and 1 N HCl. The reaction was extracted with EtOAc and then the combined organic layers were extracted with brine, dried over MgSO₄, filtered, and evaporated to give the title compound as an oil (5.96 g, >100% yield). NMR showed some EtOAc but it was used as is the next step: ¹H NMR (DMSO-d₆, δ) 0.87 (3H, d), 1.03 (3H, d), 2.06 (1H, m), 2.77 (1H, s), 4.49 (1H, d), 6.78 (1H, d), 7.02 (1H, s), 7.25 (1H, dd), 8.11 (1H, s)

Step B:
1-(5-Bromo-2-hydroxyphenyl)-2-methylpropan-1-one

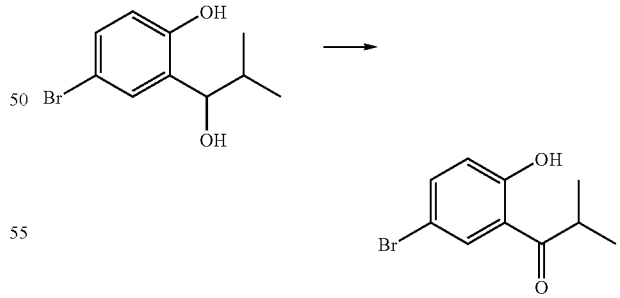

4-Bromo-2-(1-hydroxy-2-methylpropyl)phenol (4.88 g, 19.9 mmol) was dissolved in DCM (50 mL) then manganese dioxide (2.44 g, 23.8 mmol) was added. After stirring for about 2 h at ambient temperature another portion of manganese dioxide (2.44 g, 23.8 mmol) was added then the mixture was heated to about 40° C. After about 2 d the mixture was filtered then evaporated and the residue purified by flash chromatography on silica gel with 9:1 Heptane/EtOAc as an eluent to give the title compound (0.82 g, 17%): LC/MS (Table 1, Method a) $R_t$ =3.38 min; MS m/z: 241.1 (M−H)⁻.

Step C: 5-Bromo-3-isopropylbenzo[d]isoxazole

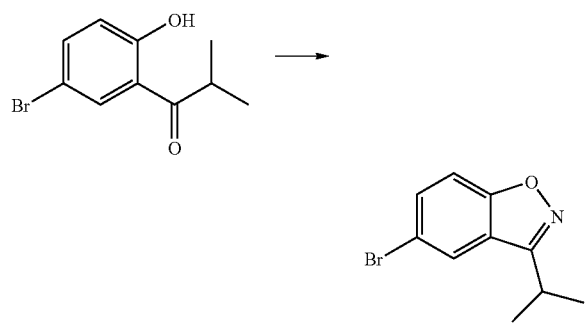

1-(5-Bromo-2-hydroxyphenyl)-2-methylpropan-1-one (0.82 g, 3.37 mmol) was dissolved in EtOH (10 mL) then hydroxylamine (50% solution in water, 0.267 g, 4.05 mmol) was added followed by HOAc (1 drop). The mixture was heated to about 80° C. for about 2 h. The mixture was cooled then evaporated under reduced pressure to give an oil. Acetic anhydride (2 mL, 20 mmol) was added and the mixture was stirred for about 45 min at ambient temperature. The mixture was concentrated under reduced pressure then pyridine (7 mL) was added and then the mixture was heated to about 145° C. for about 3 h. The mixture was cooled, treated with 1 N HCl, and extracted with EtOAc. The organic extract was dried over MgSO₄, filtered and evaporated to a residue that was then dissolved in DME (4 mL). Cesium carbonate (1.09 g, 3.35 mmol) was added and the mixture was heated at about 150° C. for about 30 min in the microwave. The mixture was evaporated and then purified by flash chromatography with 9:1 heptane/EtOAc to give the title compound (0.12 g, 15%): LC/MS (Table 1, Method a) $R_t$=3.33 min; MS m/z: 340.1 (M+H)⁺.

Step D: 5-(6-(2,4-Difluorophenyl)imidazo[2,1-b]oxazol-5-yl)-3-isopropylbenzo[d]isoxazole

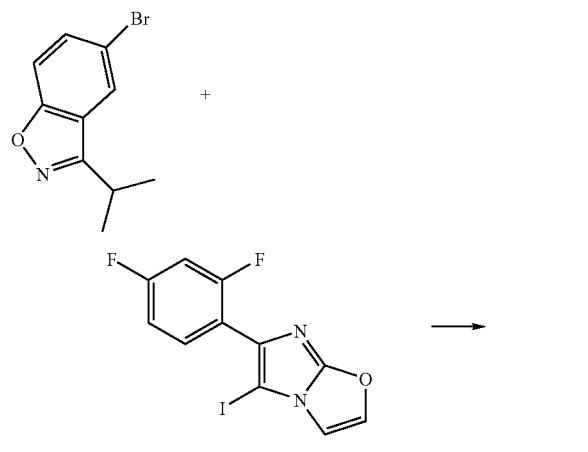

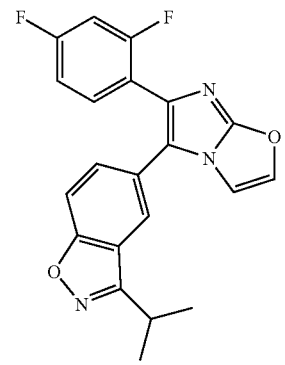

5-Bromo-3-isopropylbenzo[d]isoxazole (0.120 g, 0.500 mmol), bis(pinacolato)diboron (0.130 g, 0.512 mmol), potassium acetate (0.098 g, 0.99 mmol) and PdCl₂(dppf) (0.033 g, 0.045 mmol) in DMF (3 mL) was heated to about 90° C. for about 2 h then cooled, evaporated, triturated with DCM then filtered. The filtrate was concentrated under reduced pressure to give a dark oil which was dissolved in 1,4-dioxane (3 mL) and water (0.5 mL). Cesium carbonate (0.405 g, 1.24 mmol), PdCl₂(PPh₃)₂ (0.035 g, 0.050 mmol) and 6-(2,4-difluorophenyl)-5-iodoimidazo[2,1-b]oxazole (0.173 g, 0.500 mmol; Example #2, step A) were added and the mixture was heated to about 90° C. oil bath for about 16 h. The solvents were evaporated and the material was purified by reverse phase chromatography (Table 1, Method c). Evaporation of the fractions with the desired product resulted in a precipitate which was collected by filtration to give the title compound (0.012 g, 6.33% yield) as a tan solid: LC/MS (Table 1, Method a) $R_t$ =3.08 min; MS m/z: 380.1 (M+H)⁺.

Example #6

4-Fluoro-3-(6-(6-(4-fluorophenyl)imidazo[2,1-b]oxazol-5-yl)-[1,2,4]triazolo[4,3-a]pyridin-3-yl)benzoic acid

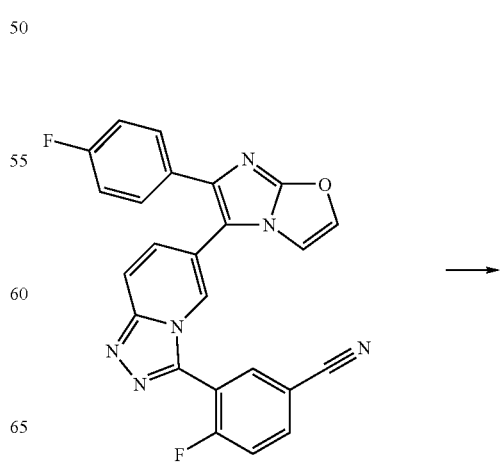

-continued

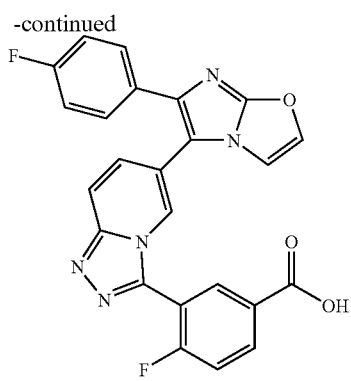

To a suspension of 4-fluoro-3-{6-[6-(4-fluorophenyl)-imidazo[2,1-b]oxazol-5-yl]-[1,2,4]triazolo[4,3-a]pyridin-3-yl}-benzonitrile (0.15 g, 0.34 mmol; Example #K.1.19) in water (1 mL) and then was added NH₄OH (28-30% in water, 2.0 mL, 51 mmol) and 1M NaOH (1 mL, 1.0 mmol). The reaction mixture was stirred at about 65° C. for about 8 h. Ammonia (0.5 M in 1,4-dioxane, 10 mL) was added and the reaction mixture was stirred about 72 h at about 65° C. The organic solvent was removed under reduced pressure and aqueous layer was buffered with ammonium acetate aqueous solution. The crude material was purified by reverse phase preparative chromatography (Table 1, Method e). The resulting material was purified by trituration with hot MeOH to afford the title compound (0.038 g, 23%) LC/MS (Table 1, Method a) R$_t$ = 1.84 min; MS m/z: 458.1 (M+H)⁺.

Example #7

2-(6-(6-(4-Fluorophenyl)imidazo[2,1-b]oxazol-5-yl)-[1,2,4]triazolo[4,3-a]pyridin-3-yl)ethanol

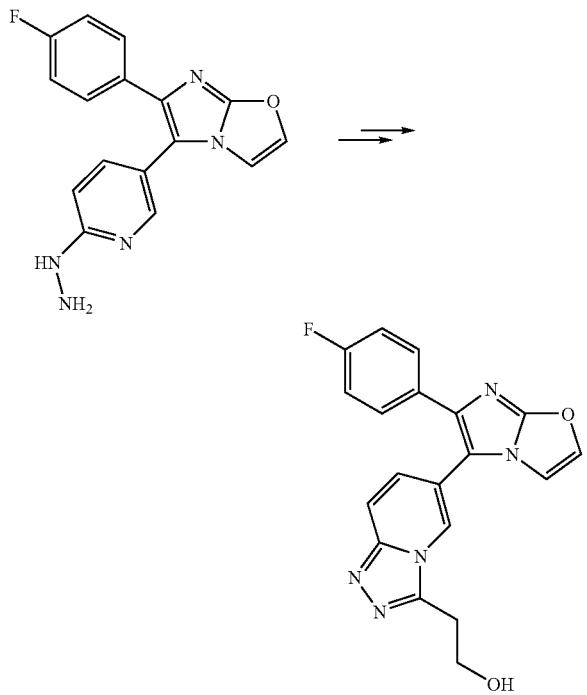

The 6-(2,4-difluorophenyl)-5-(6-hydrazinylpyridin-3-yl)imidazo[2,1-b]oxazole (0.20 g, 0.65 mmol; prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine) and 3-(tert-butyldimethylsilyloxy)propanal (0.12 g, 0.65 mmol; Toronto) were dissolved in MeOH (5.0 mL) and heated to about 65° C. for about 1 h. The MeOH was evaporated then DCM (5 mL) was added followed by iodobenzene diacetate (0.21 g, 0.65 mmol). The reaction was stirred for about 16 h and then evaporated. The resulting solid was dissolved in 1M TBAF in THF (5 mL). The reaction was allowed to stir for about 30 min. The THF was evaporated and the crude material was purified by reverse phase HPLC (Table 1, Method f). The fractions containing product were concentrated under reduced pressure and the resulting precipitate was filtered and dried under vacuum for about 16 h at about 60° C. to provide the title compound (0.033 g, 14%) as a white solid: LC/MS (Table 1, Method a) R$_t$=1.76 min; MS m/z: 364.1 (M+H)⁺.

Example #8

5-([1,2,4]Triazolo[4,3-a]pyridin-6-yl)-6-(4-fluorophenyl)imidazo[2,1-b]oxazole

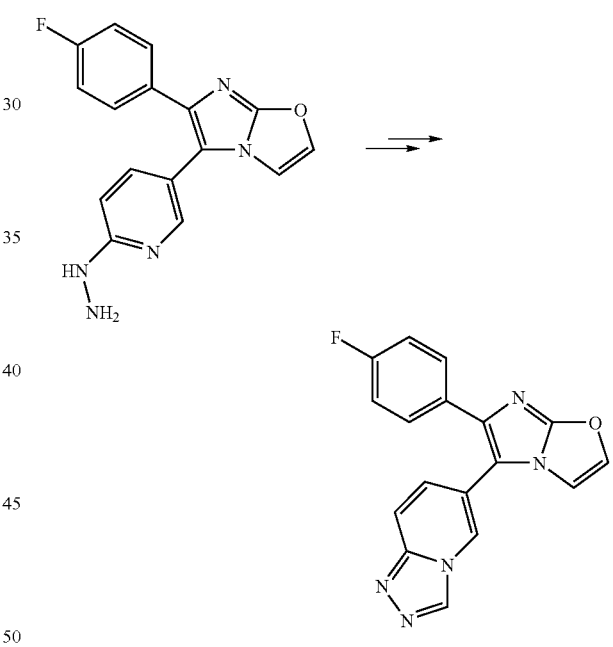

The 6-(2,4-difluorophenyl)-5-(6-hydrazinylpyridin-3-yl)imidazo[2,1-b]oxazole (0.20 g, 0.65 mmol; prepared using A from 6-(4-fluorophenyl)-imidazo[2,1-b]oxazole [prepared according to WO2004110990A2, Example 1, Steps 1-3] with NIS, C with 2-fluoropyridine-5-boronic acid [Asymchem], D with hydrazine) and ethyl 2-oxoacetate (0.65 mL, 9.7 mmol) were dissolved in MeOH (5.0 mL) and heated to about 65° C. for about 1 h. The MeOH was evaporated and then DCM (5 mL) was added followed by iodobenzene diacetate (0.53 g, 1.6 mmol). The reaction was stirred for about 15 min then the DCM was evaporated and the resulting solid was triturated with Et₂O. The solid was dissolved in 1,4-dioxane (10 mL) and LiOH (0.060 g, 2.4 mmol) dissolved in water (2 mL) was added drop-wise followed by heating to about 50° C. for about 30 min. The 1,4-dioxane was evaporated and the pH was adjusted to about 1 with 1N HCl. The resulting precipitate was filtered and washed with water (about 10 mL) and

Example #9

(trans)-4-(6-(6-(4-Fluorophenyl)imidazo[2,1-b]oxazol-5-yl)-[1,2,4]triazolo[4,3-a]pyridin-3-yl)-N-methylcyclohexanamine

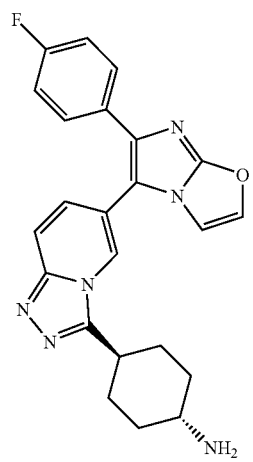

To a 100 mL round-bottom flask was added tert-butyl (trans)-4-(6-(6-(4-fluorophenyl)imidazo[2,1-b]oxazol-5-yl)-[1,2,4]triazolo[4,3-a]pyridin-3-yl)cyclohexylcarbamate (4.00 g, 7.74 mmol; Example #K.1.1.35) and MeI (0.533 mL, 8.52 mmol) which were then dissolved in THF (10 mL). NaH (0.619 g, 15.5 mmol) was added. The reaction was allowed to stir for about 16 h at ambient temperature after which time TFA (5 mL) was added. The reaction was allowed to stir at ambient temperature for about 2 h after which time the reaction was quenched with aqueous NaHCO$_3$ and the organic layer was separated. The aqueous layer was washed with DCM and the combined organic layers were dried over MgSO$_4$, filtered, and concentrated in vacuo. The crude material was purified by silica gel chromatography using EtOAc/ MeOH (gradient, 1:0 to 9:1) to provide the title compound. (0.032 g, 1.0%): LC/MS (Table 1, Method a) R$_t$ =1.6 min; MS m/z: 431.2 (M+H)$^+$.

Example #10

3-(6-(6-(4-Fluorophenyl)imidazo[2,1-b]oxazol-5-yl)-[1,2,4]triazolo[4,3-a]pyridin-3-yl)-2,2-dimethylpropanoic acid

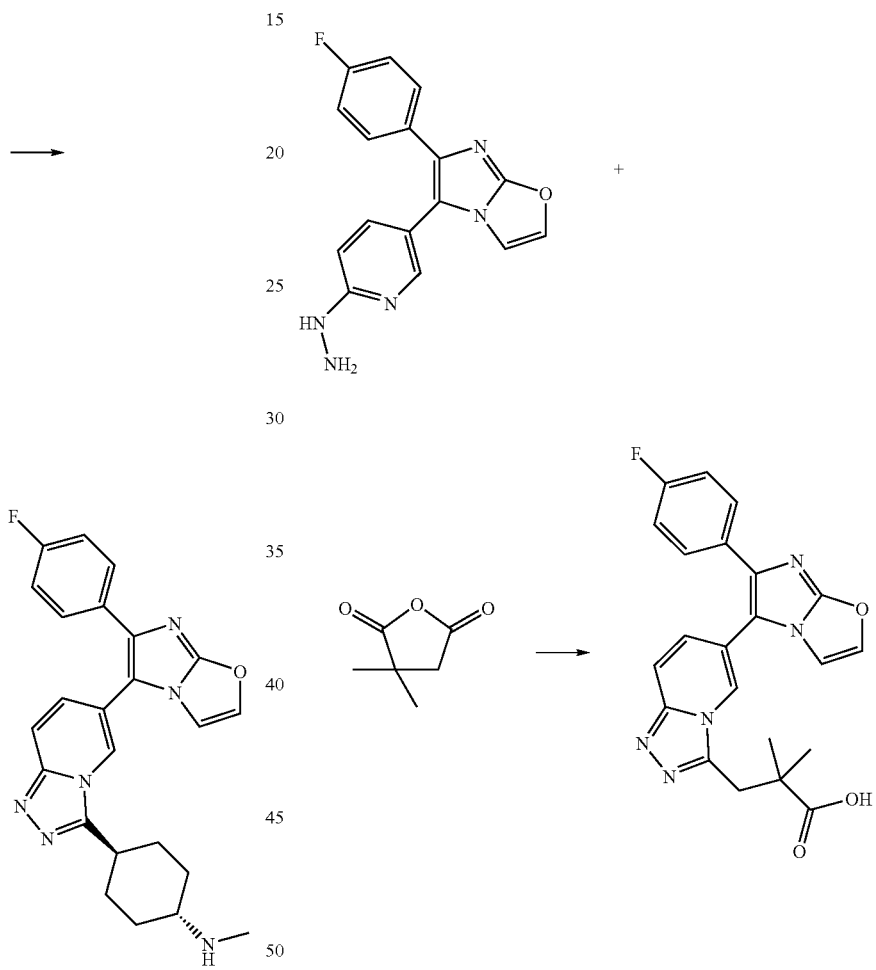

In a 100 mL round-bottom flask 6-(4-fluorophenyl)-5-(6-hydrazinylpyridin-3-yl)imidazo[2,1-b]oxazole (0.20 g, 0.65 mmol; prepared using A from 6-(4-fluorophenyl)-imidazo[2,1-b]oxazole [prepared according to WO2004110990A2, Example 1, Steps 1-3] with NIS, C using 2-fluoropyridine-5-boronic acid [Asymchem], D using hydrazine) and 3,3-dimethyldihydrofuran-2,5-dione (0.091 g, 0.71 mmol) were dissolved in 1,4-dioxane (5 mL) and the mixture was heated to about 100° C. After about 2 h the reaction was cooled to ambient temperature and concentrated in vacuo. The crude material was dissolved in DCM and crystallized upon the addition of Et$_2$O. The resulting solid was filtered and dried under vacuum to provide the title compound as a white solid (0.22 g, 81%): LC/MS (Table 1, Method a) R$_t$ =1.86 min; MS m/z: 420.2 (M+H)$^+$.

Example #11

4-(6-(6-(4-Fluorophenyl)imidazo[2,1-b]oxazol-5-yl)-[1,2,4]triazolo[4,3-a]pyridin-3-yl)-2-methylbutan-2-ol

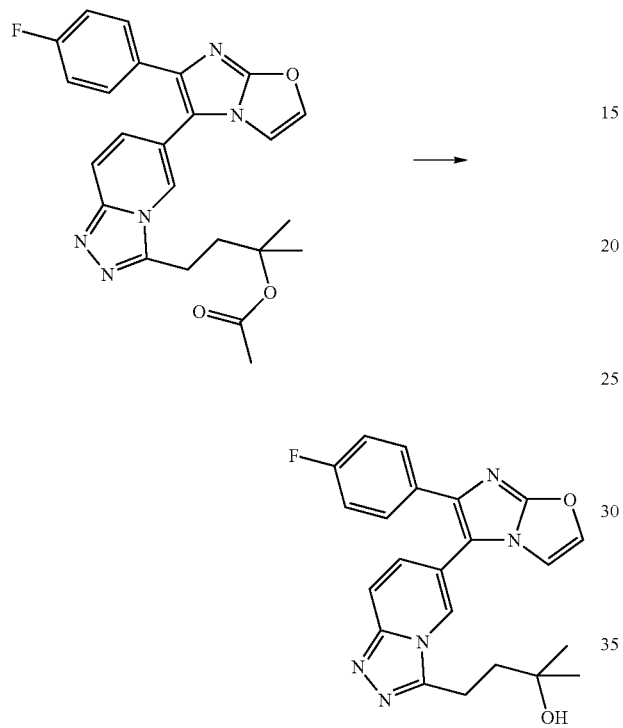

A 25 mL flask was charged with 4-(6-(6-(4-fluorophenyl)imidazo[2,1-b]oxazol-5-yl)-[1,2,4]triazolo[4,3-a]pyridin-3-yl)-2-methylbutan-2-yl acetate (0.196 g, 0.438 mmol; Example #K.1.1.7) in 1,4-dioxane (2 mL) to give a yellow solution. To the solution was added 5.0 M aqueous HCl (0.44 mL, 2.2 mmol) and the mixture was stirred at ambient temperature. After about 16 h, aqueous NaOH was added to the mixture and a precipitate formed. The precipitate was collected via filtration and was rinsed with water. The material was dried in a vacuum oven to furnish the title compound as an off-white solid (0.036 g, 21%): LC/MS (Table 1, Method a) $R_t$=1.89 min; MS m/z/z: 406.2 (M+H)$^+$.

Example #12

3-(6-(6-(2,4-Difluorophenyl)imidazo[2,1-b]oxazol-5-yl)-[1,2,4]triazolo[4,3-a]pyridin-3-yl)-2,2-dimethylpropan-1-ol

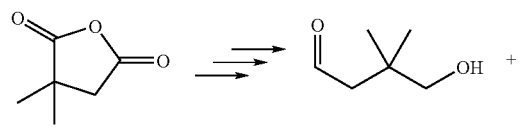

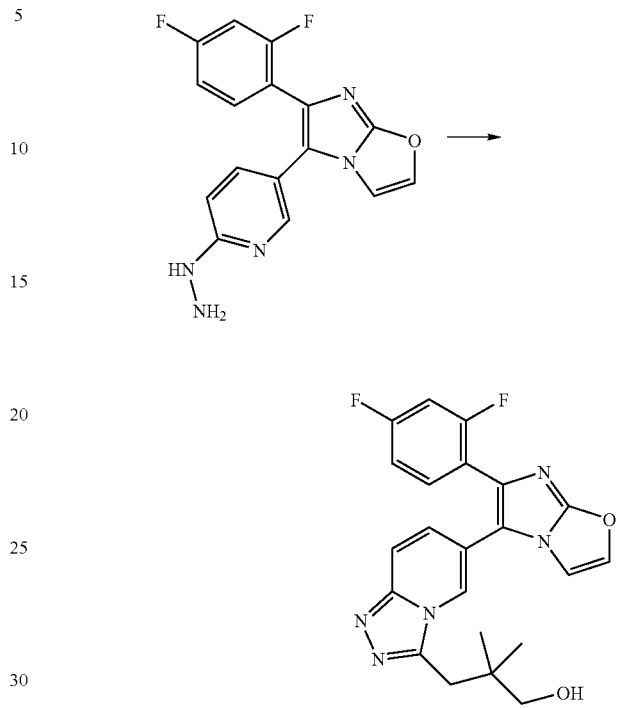

To a 50 mL round-bottom flask was added 3,3-dimethyldihydrofuran-2,5-dione (1.0 g, 7.80 mmol) in THF (25 mL) to give a colorless solution. This solution was cooled to about −78° C. followed by the addition of LAH (1.48 g, 39.0 mmol) in 3 batches. The reaction was warmed to ambient temperature and allowed to stir for about 2 h. 1N NaOH (about 10 mL) and EtOAc (about 10 mL) were added and the reaction was allowed to stir for about 1 h. The reaction was filtered though Celite® and the organic layer was separated, dried over MgSO$_4$ and concentrated under reduced pressure to give a clear colorless oil. To this oil a solution of Dess-Martin periodinane (3.1 g, 7.3 mmol) in DCM (5 mL) was added dropwise and the reaction was allowed to stir for about 1 h. The reaction was then concentrated under reduced pressure, suspended in Et$_2$O, filtered through a short plug of silica gel and subsequently concentrated under reduced pressure. To the resulting oil was added 5-[6-(2,4-difluorophenyl)-imidazo[2,1-b]oxazol-5-yl]-pyridin-2-yl-hydrazine (0.25 g, 0.76 mmol; prepared using C from Example #2, step A with 2-fluoropyridine-5-boronic acid [Asymchem], D with hydrazine) and MeOH (5 mL) followed by heating to about 60° C. for about 1 h. Then the reaction was cooled to ambient temperature and iodobenzene diacetate (0.246 g, 0.764 mmol) was added and the reaction was allowed to stir for about 1 h. The reaction was then concentrated under reduced pressure and purified by silica gel chromatography (40 g of SiO$_2$, gradient from 0% to 10% MeOH in EtOAc) to provide the title compound as a white solid (0.01 g, 3%): LC/MS (Table 1, Method a) R=1.93 min; MS m/z: 424.2 (M+H)$^+$.

What is claimed is:

1. A compound of formula (I)

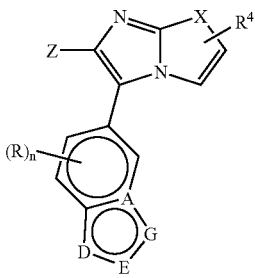

Formula (I)

pharmaceutically acceptable salts thereof, or pro-drugs thereof, wherein

X is O or S;
A is C or N;
D is O, N or $NR^b$;
E is N or $CR^a$;
G is N, $NR^b$ or $CR^c$;
Z is selected from the optionally substituted group consisting of phenyl, naphthyl, azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indolinyl, indazolyl, isoindolinyl, isoxazolyl, isothiazolyl, oxadiazolyl, oxazolyl, purinyl, pyranyl, pyrazinyl, pyrazolyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl or tropanyl;
R for each occurrence is independently H, F, Cl, or ($C_1$-$C_4$)alkyl;
$R^a$ is selected from the group consisting of H, $NR^2R^3$, pyridinyl and ($C_1$-$C_6$)alkyl;
$R^b$ is selected from the group consisting of H, —S(O)$_2$—($C_1$-$C_4$)alkyl, optionally substituted ($C_1$-$C_6$)alkyl, optionally substituted ($C_3$-$C_6$)cycloalkyl, optionally substituted ($C_1$-$C_6$)alkyl-$R^1$, optionally substituted aryl, optionally substituted heterocyclyl and optionally substituted heteroaryl;
$R^c$ is H or $R^c$ is selected from the group consisting of, $NR^2R^3$, optionally substituted —C(O)—NH—($C_1$-$C_4$)alkyl, —CO$_2$—($C_1$-$C_3$)alkyl, —($C_3$-$C_4$)alkylamino, optionally substituted ($C_1$-$C_6$)alkyl, optionally substituted ($C_3$-$C_6$)cycloalkyl, optionally substituted ($C_3$-$C_6$)cycloalkenyl, —($C_1$-$C_6$)alkyl-$R^1$, optionally substituted phenyl, optionally substituted heterocyclyl and optionally substituted heteroaryl;
wherein $R^c$ is optionally substituted by one or more substituents selected from the group consisting of CF$_3$, CN, halo, optionally substituted ($C_1$-$C_3$)alkyl, optionally substituted ($C_1$-$C_3$)alkoxy, —C(O)—NH-optionally substituted ($C_1$-$C_3$)alkyl, —C(O)—NH-optionally substituted ($C_1$-$C_6$)alkyl-optionally substituted amino, —C(O)—OCH$_3$, —NH—C(O)-optionally substituted ($C_1$-$C_3$)alkyl, OH, COOH, $NR^2R^3$, —C(O)—NH-optionally substituted ($C_1$-$C_5$)alkyl; —C(O)—NH-optionally substituted ($C_3$-$C_6$)cycloalkyl, —C(O)—NH-optionally substituted ($C_1$-$C_6$)alkyl-optionally substituted ($C_3$-$C_6$)cycloalkyl, —NH—C(O)—O-optionally substituted ($C_1$-$C_4$)alkyl, NH$_2$, N(H)CH$_3$, N(CH$_3$)$_2$ and —O—C(O)-optionally substituted ($C_1$-$C_3$)alkyl;

$R^1$ is selected from the optionally substituted group consisting of amino, phenyl, heteroaryl, heterocyclyl and ($C_3$-$C_6$)cycloalkyl;
$R^2$ and $R^3$ are independently selected from H and optionally substituted ($C_1$-$C_4$)alkyl;
$R^4$ is H, halo, CN, SO$_2$, CONH—($C_1$-$C_6$)alkyl, —CO—N(CH$_3$)$_2$, —CO—N(H)-optionally substituted ($C_1$-$C_6$)alkyl, —CO—N(H)-optionally substituted ($C_1$-$C_6$)alkyl-$NR^2R^3$, —NHCO—($C_1$-$C_6$)alkyl, SO$_2$—($C_1$-$C_6$)alkyl, CO—($C_1$-$C_6$)alkyl, CO$_2$—($C_1$-$C_3$)alkyl or optionally substituted ($C_1$-$C_6$) alkyl; and
n is 1, 2 or 3;
provided that the compound is not
1-methyl-6-[6-(6-methyl-pyridin-2-yl)]-imidazo[2,1-b]thiazol-5-yl-1H-benzotriazole;
2-methyl-5-[6-(6-methyl-pyridin-2-yl)]-imidazo[2,1-b]thiazol-5-yl-1H-benzotriazole;
2-methyl-5-[3-methyl-6-(6-methyl-pyridin-2-yl)]-imidazo[2,1-b]thiazol-5-yl-1H-benzotriazole; or
2-methyl-5-[2-methyl-6-(6-methyl-pyridin-2-yl)]-imidazo[2,1-b]thiazol-5-yl-1H-benzotriazole.

2. The compound of claim 1 wherein
X is O or S;
A is C or N;
D is N or $NR^b$;
E is N or $CR^a$;
G is N, $NR^b$ or $CR^c$;
Z is selected from the optionally substituted group consisting of phenyl, naphthyl, azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indolinyl, indazolyl, isoindolinyl, isoxazolyl, isothiazolyl, oxadiazolyl, oxazolyl, purinyl, pyranyl, pyrazinyl, pyrazolyl, pyrimidinyl, pyrrolyl, triazolyl, thiazolyl, thiophenyl, tetrahydroindolyl, tetrazolyl, thiadiazolyl, thienyl, thiomorpholinyl or tropanyl;
R for each occurrence is independently selected from the group consisting of H, F, Cl, or ($C_1$-$C_4$)alkyl;
$R^a$ is selected from the group consisting of H, $NR^2R^3$, pyridinyl and ($C_1$-$C_6$)alkyl;
$R^b$ is selected from the group consisting of H, —S(O)$_2$—($C_1$-$C_4$)alkyl, optionally substituted ($C_1$-$C_6$)alkyl, optionally substituted ($C_3$-$C_6$)cycloalkyl, optionally substituted ($C_1$-$C_6$)alkyl-$R^1$, optionally substituted aryl, optionally substituted heterocyclyl and optionally substituted heteroaryl;
$R^c$ is selected from the group consisting of H, $NR^2R^3$, optionally substituted —C(O)—NH—($C_1$-$C_4$)alkyl, —CO$_2$—($C_1$-$C_3$)alkyl, optionally substituted ($C_1$-$C_6$) alkyl, optionally substituted ($C_3$-$C_6$)cycloalkyl, —($C_1$-$C_6$)alkyl-$R^1$, optionally substituted phenyl, optionally substituted heterocyclyl and optionally substituted heteroaryl;
$R^1$ is selected from the optionally substituted group consisting of amino, phenyl, heteroaryl, heterocyclyl and ($C_3$-$C_6$)cycloalkyl;
$R^2$ and $R^3$ are independently selected from H and ($C_1$-$C_4$) alkyl;
$R^4$ is H, halo, CN, SO$_2$NH$_2$, CONH—($C_1$-$C_6$)alkyl, NHCO—($C_1$-$C_6$)alkyl, SO$_2$—($C_1$-$C_6$)alkyl, CO—($C_1$-$C_6$)alkyl, CO$_2$—($C_1$-$C_3$)alkyl or optionally substituted ($C_1$-$C_6$) alkyl; and
n is 1, 2 or 3.

3. The compound of claim 2 wherein Z is optionally substituted phenyl.

4. The compound of claim 3 wherein D is N.

5. The compound of claim 4 wherein E is N.

6. The compound of claim 5 wherein A is N.

7. The compound of claim 6 wherein

G is $CR^c$; and $R^c$ is $NH_2$ or is selected from the optionally substituted group consisting of —C(O)—NH—($C_1$-$C_4$)alkyl, phenyl, heteroaryl, heterocyclyl, ($C_1$-$C_4$)alkyl, ($C_3$-$C_4$)cycloalkyl, —($C_3$-$C_4$)alkylamino and —$CO_2$—($C_1$-$C_4$)alkyl.

8. The compound of claim 7 wherein Z is phenyl substituted with one or more substituents each independently selected from $CF_3$ and halogen.

9. The compound of claim 8 wherein Z is phenyl substituted with one or more F;

$R^c$ is selected from the optionally substituted group consisting of phenyl, imidazolyl, ($C_1$-$C_4$)alkyl, ($C_3$-$C_4$)cycloalkyl and heterocyclyl;

n is 1; and

R is H.

10. The compound of claim 9 wherein X is O and $R^c$ is selected from the optionally substituted group consisting of phenyl, ($C_1$-$C_4$)alkyl and ($C_3$-$C_4$)cycloalkyl.

11. The compound of claim 10 wherein $R^c$ is optionally substituted by one or more substituents selected from the group consisting of $CF_3$, CN, halo, optionally substituted ($C_1$-$C_3$)alkyl, optionally substituted ($C_1$-$C_3$)alkoxy, —C(O)—NH-optionally substituted ($C_1$-$C_3$)alkyl, —C(O)—NH-optionally substituted ($C_1$-$C_6$)alkyl-optionally substituted amino, —C(O)—$OCH_3$ and —NH—C(O)-optionally substituted ($C_1$-$C_3$)alkyl.

12. The compound of claim 11 wherein the compound is

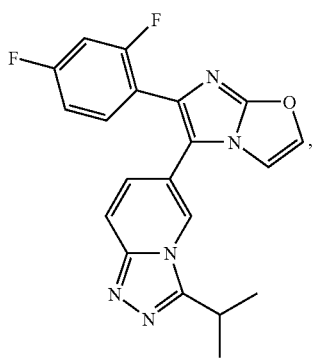

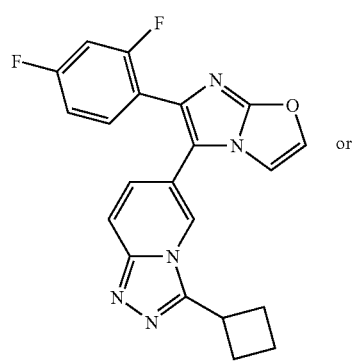

or

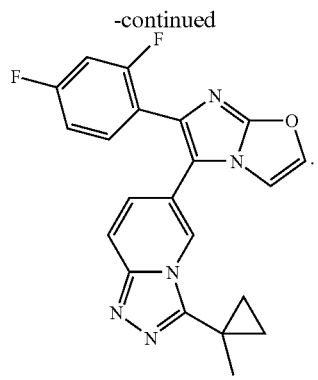

13. The compound of claim 5 wherein A is C.

14. The compound of claim 13 wherein

G is $NR^b$; and $R^b$ is H or is selected from the optionally substituted group consisting of phenyl, ($C_1$-$C_6$)alkyl, ($C_3$-$C_6$)cycloalkyl and ($C_1$-$C_6$)alkyl-$R^1$.

15. The compound of claim 14 wherein $R^1$ is ($C_3$-$C_6$)cycloalkyl or phenyl.

16. The compound of claim 15 wherein Z is phenyl substituted with one or more F;

$R^b$ is selected from the optionally substituted group consisting of phenyl, ($C_1$-$C_6$)alkyl, —$CH_2$-cyclopropyl;

X is O;

n is 1; and

R is H.

17. The compound of claim 16 wherein the compound is

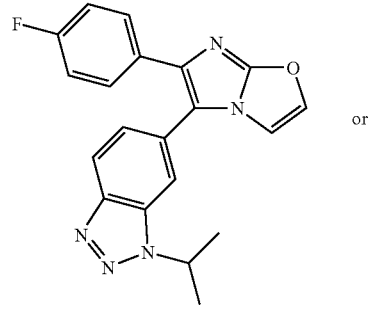

or

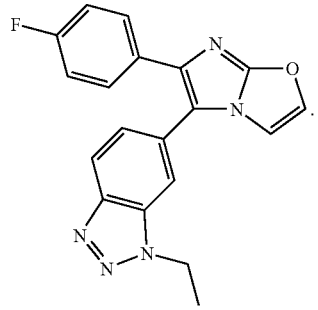

18. The compound of claim 3 wherein E is $CR^a$.

19. The compound of claim 18 wherein G is $NR^b$.

20. The compound of claim 19 wherein $R^a$ is $NH_2$, ($C_1$-$C_4$)alkyl, heteroaryl or —NH—$S(O)_2$-phenyl;

$R^b$ is H or a bond or is selected from the optionally substituted group consisting of ($C_1$-$C_5$)alkyl, —($C_1$-$C_5$)alkyl-$R^1$, ($C_3$-$C_6$)cycloalkyl and aryl; and A is C.

21. The compound of claim 20 wherein
$R^a$ is $NH_2$, $CH_3$, pyridinyl or —NH—S(O)$_2$-phenyl;
$R^b$ is a bond or is selected from the optionally substituted group consisting of (C$_1$-C$_5$)alkyl, —CH$_2$-azetidinyl, —CH$_2$-cyclohexyl, —CH$_2$-cyclopropyl, —CH$_2$-pyridinyl, —CH$_2$-tetrahydropyranyl, —CH$_2$-pyrrolidinyl, —CH$_2$-pyrrolyl, benzyl, cyclopropyl, cyclohexyl, and phenyl;
R is H;
n is 1; and
Z is phenyl substituted with F.

22. The compound of claim 21 wherein the compound is

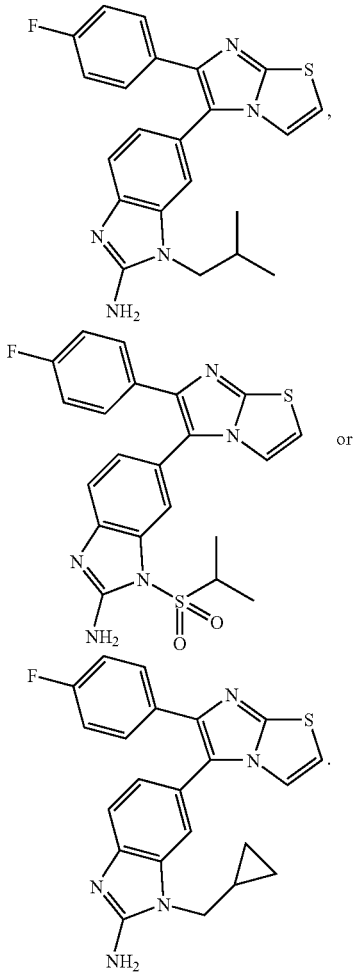

23. The compound of claim 3 wherein D is O, E is N, A is C and G is CR$^c$;
$R^c$ is NH$_2$ or $R^c$ is selected from the optionally substituted group consisting of —C(O)—NH—(C$_1$-C$_4$)alkyl, phenyl, heteroaryl, heterocyclyl, (C$_1$-C$_4$)alkyl, (C$_3$-C$_4$)cycloalkyl, —(C$_3$-C$_4$)alkylamino and —CO$_2$—(C$_1$-C$_4$)alkyl;
n is 1;
R is H; and
Z is phenyl substituted with one or more F.

24. A method of treating a condition in a patient comprising administering a therapeutically effective amount of a compound of claim 1 or a physiologically acceptable salt thereof to a patient, wherein said condition is selected from the group consisting of rheumatoid arthritis, osteoarthritis, chronic obstructive pulmonary disease, psoriasis, psoriatic arthritis, inflammatory bowel disease, Crohn's disease, lupus, multiple sclerosis, juvenile chronic arthritis, Lyme arthritis, reactive arthritis, septic arthritis, systemic onset juvenile rheumatoid arthritis, juvenile rheumatoid arthritis, rheumatoid arthritis associated interstitial lung disease, ankylosing spondylitis associated lung disease, gouty arthritis, psoriasis type 1, psoriasis type 2, rheumatoid spondylitis, polymyalgia rheumatica, polyarticular JRA, septic arthritis, and spondylitis ankylosans.

25. A pharmaceutical composition comprising a compound of Formula (I)

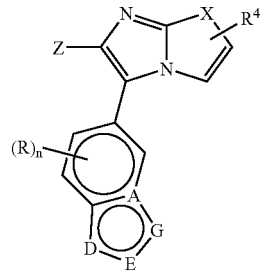

Formula (I)

and a pharmaceutically acceptable carrier or excipient, wherein
X is O or S;
A is C or N;
D is O, N or NR$^b$;
E is N or CR$^a$;
G is N, NR$^b$ or CR$^c$;
Z is selected from the optionally substituted group consisting of phenyl, naphthyl azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indolinyl, indazolyl, isoindolinyl, isoxazolyl, isothiazolyl, oxadiazolyl, oxazolyl, purinyl, pyranyl, pyrazinyl, pyrazolyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl or tropanyl;
R for each occurrence is independently H, F, Cl, or (C$_1$-C$_4$)alkyl;
$R^a$ is selected from the group consisting of H, NR$^2$R$^3$, pyridinyl and (C$_1$-C$_6$)alkyl;
$R^b$ is selected from the group consisting of H, —S(O)$_2$—(C$_1$-C$_4$)alkyl, optionally substituted (C$_1$-C$_6$)alkyl, optionally substituted (C$_3$-C$_6$)cycloalkyl, optionally substituted (C$_1$-C$_6$)alkyl-R$^1$, optionally substituted aryl, optionally substituted heterocyclyl and optionally substituted heteroaryl;
$R^c$ is selected from the group consisting of H, NR$^2$R$^3$, optionally substituted —C(O)—NH—(C$_1$-C$_4$)alkyl, —CO$_2$—(C$_1$-C$_3$)alkyl, optionally substituted (C$_1$-C$_6$)alkyl, optionally substituted (C$_3$-C$_6$)cycloalkyl, optionally substituted (C$_3$-C$_6$)cycloalkenyl, —(C$_1$-C$_6$)alkyl-R$^1$, optionally substituted phenyl, optionally substituted heterocyclyl and optionally substituted heteroaryl;
$R^1$ is selected from the optionally substituted group consisting of amino, phenyl, heteroaryl, heterocyclyl and (C$_3$-C$_6$)cycloalkyl;
$R^2$ and $R^3$ are independently selected from H and (C$_1$-C$_4$)alkyl;
$R^4$ is H, halo, CN, SO$_2$, CONH—(C$_1$-C$_6$)alkyl, —CO—N(CH$_3$)$_2$, —CO—N(H)-optionally substituted (C$_1$-C$_6$)alkyl, —CO—N(H)-optionally substituted (C$_1$-C$_6$)alkyl-NR$^2$R$^3$, —NHCO—(C$_1$-C$_6$)alkyl, SO$_2$—(C$_1$-C$_6$)alkyl, CO—(C$_1$-C$_6$)alkyl, CO$_2$—(C$_1$-C$_3$)alkyl or optionally substituted (C$_1$-C$_6$) alkyl; and
n is 1, 2 or 3.

* * * * *

UNITED STATES PATENT AND TRADEMARK OFFICE
CERTIFICATE OF CORRECTION

PATENT NO. : 7,790,741 B2
APPLICATION NO. : 11/973147
DATED : September 7, 2010
INVENTOR(S) : Calderwood et al.

It is certified that error appears in the above-identified patent and that said Letters Patent is hereby corrected as shown below:

Claim 2, Column 148 line 34.

"pyrrolo[2,3-d]pyrimidinyl, pyrazolo[3,4-d]pyrimidinyl, quinolinyl, quinazolinyl," is missing following the phrase "pyrimidinyl, pyrrolyl," and should be corrected.

Therefore, "pyrimidinyl, pyrrolyl, triazolyl, thiazolyl, thiophenyl, tetrahydroindolyl, tetrazolyl, thiadiazolyl, thienyl, thiomorpholinyl or tropanyl;" should read --pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrahydroindolyl, tetrazolyl, thiadiazolyl, thienyl, thiomorpholinyl or tropanyl;--.

Claim 12, Column 149 line 55.

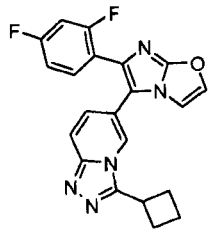

The structure " " is incorrect because it contains an extra fluorine atom on the phenyl ring and should be corrected.

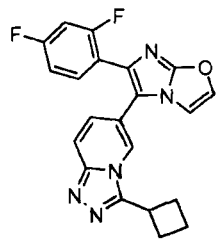 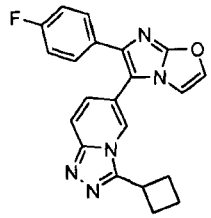

Therefore "    " should read --    --.

Signed and Sealed this

Thirtieth Day of November, 2010

David J. Kappos
*Director of the United States Patent and Trademark Office*

Claim 12, Column 150 line 1.
The structure " 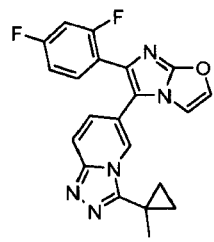 " is incorrect because it contains an extra fluorine atom on the phenyl ring and should be corrected.
Therefore, " 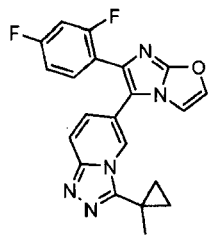 " should read -- 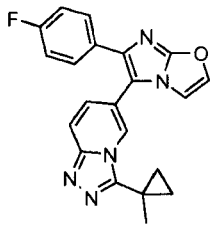 --.